US009962452B2

(12) United States Patent
Sun

(10) Patent No.: US 9,962,452 B2
(45) Date of Patent: May 8, 2018

(54) SOLUBLE COMPLEXES OF DRUG ANALOGS AND ALBUMIN

(71) Applicant: Zhuhai Beihai Biotech Co., Ltd., Zhuhai (CN)

(72) Inventor: Qun Sun, Princeton, NJ (US)

(73) Assignee: Zhuhai Beihai Biotech Co., Ltd., Zhuhai (CN)

( * ) Notice: Subject to any disclaimer, the term of this patent is extended or adjusted under 35 U.S.C. 154(b) by 0 days. days.

(21) Appl. No.: 14/765,773

(22) PCT Filed: Jan. 31, 2014

(86) PCT No.: PCT/US2014/014079
§ 371 (c)(1),
(2) Date: Aug. 4, 2015

(87) PCT Pub. No.: WO2014/121033
PCT Pub. Date: Aug. 7, 2014

(65) Prior Publication Data
US 2015/0366984 A1    Dec. 24, 2015

Related U.S. Application Data

(60) Provisional application No. 61/760,573, filed on Feb. 4, 2013.

(51) Int. Cl.
*A61K 31/337* (2006.01)
*A61K 47/48* (2006.01)
*A61K 31/4745* (2006.01)

(52) U.S. Cl.
CPC ...... *A61K 47/48284* (2013.01); *A61K 31/337* (2013.01); *A61K 31/4745* (2013.01)

(58) Field of Classification Search
CPC ............ A61K 47/48284; A61K 31/337; A61K 31/4745
See application file for complete search history.

(56) References Cited

U.S. PATENT DOCUMENTS

| | | | |
|---|---|---|---|
| 5,604,213 A | 2/1997 | Barrie et al. | |
| 5,635,517 A | 6/1997 | Muller et al. | |
| 7,445,764 B1 | 11/2008 | Kratz | |
| 7,452,900 B2* | 11/2008 | Marzi | C07D 491/22 514/283 |
| 7,498,340 B2* | 3/2009 | Marzi | C07D 491/22 514/283 |
| 7,576,104 B2 | 8/2009 | Robarge et al. | |
| 7,772,254 B2 | 8/2010 | Sun | |
| 7,820,788 B2 | 10/2010 | Desai et al. | |
| 7,923,536 B2 | 4/2011 | Desai et al. | |
| 8,076,474 B2 | 12/2011 | Hunt | |
| 8,138,229 B2 | 3/2012 | Desai et al. | |
| 8,338,588 B2 | 12/2012 | Hunt | |
| 8,748,610 B2 | 6/2014 | Sun | |
| 8,853,260 B2 | 10/2014 | Desai et al. | |
| 8,911,775 B2* | 12/2014 | Lee | A61K 9/1075 424/450 |
| 8,927,694 B2* | 1/2015 | McDonagh | C07K 14/765 530/350 |
| 8,927,725 B2 | 1/2015 | Greig et al. | |
| 9,150,585 B2* | 10/2015 | Sun | C07D 491/22 |
| 2009/0253651 A1* | 10/2009 | Norbedo | C08B 37/0072 514/54 |
| 2011/0021567 A1 | 1/2011 | Devarakonda et al. | |
| 2012/0177743 A1 | 7/2012 | Desai et al. | |
| 2012/0283292 A1 | 11/2012 | Milne et al. | |
| 2014/0024807 A1 | 1/2014 | Salamone et al. | |
| 2014/0135356 A1 | 5/2014 | Sun | |
| 2015/0290332 A1* | 10/2015 | Kim | A61K 31/704 530/363 |
| 2015/0291562 A1 | 10/2015 | Crew et al. | |
| 2016/0145314 A1* | 5/2016 | Li | C07K 14/4746 424/85.6 |
| 2017/0216443 A1 | 8/2017 | Sun | |

FOREIGN PATENT DOCUMENTS

| | | |
|---|---|---|
| CN | 1863790 | 11/2006 |
| EP | 2007386 | 8/2012 |
| WO | WO2003066595 | 8/2003 |
| WO | WO2005030753 | 4/2005 |
| WO | WO2008133973 | 11/2008 |
| WO | WO2009023539 | 2/2009 |
| WO | 2009074678 | * 6/2009 |
| WO | WO2009126920 | 10/2009 |
| WO | WO2010092342 | 8/2010 |
| WO | WO2011085000 | 7/2011 |

OTHER PUBLICATIONS

Trynda-Lemiesz, J Inorg Biochem, vol. 77, 141-146, 1999.*
Li, Intern J of Nanomedicine, 2011, vol. 6, 397-405.*
Chen, J Mol Graph and Modelling, vol. 33, 35-43, 2012.*
Zsila, Bioinformatics, vol. 27(13), 1806-1819, 2011.*
Lopez-Gomez, CLin Transl Oncol, vol. 14, 641-658, 2012.*
Ge, CA158:253017, abstract only of Small, vol. 8(23), 35-1961. 73-3578, 2012.*
Zhang, Polym Chem, 2012, 3, 1958.*
Yu, CA 158:662530, abstract only of Fenxi Shiyanshi, 2012, vol. 31(1), 42-46.*
Zu, International J of Nanomedicine, 2013, vol (8), 1207-1222.*
"Multiple Myeloma: Treatment Options," Cancer.Net [online] Sep. 2014 [retrieved on Sep. 23, 2014]. Retrieved from the Internet: <URL: http://www.cancer.net/cancer-types/multiple-myeloma/treatment-options>, 7 pages.

(Continued)

*Primary Examiner* — D Margaret M Seaman
(74) *Attorney, Agent, or Firm* — Fish & Richardson P.C.

(57) ABSTRACT

The present invention provides novel, non-covalently bound complexes of serum albumin and analogs of poorly soluble drugs, such as camptothecin. The novel complexes are significantly more water-soluble than the camptothecin analogs and are useful as prodrug forms of the camptothecin analogs for the treatment of mammalian cell proliferative diseases, such as cancer.

16 Claims, 2 Drawing Sheets

(56) References Cited

OTHER PUBLICATIONS

"Myelodysplastic Syndromes Treatment (PDQ®)," Cancer.gov [online] Jun. 11, 2014 [retrieved on Sep. 24, 2014]. Retrieved from the Internet: <URL: http://www.cancer.gov/cancertopics/pdq/treatment/myelodysplastic/page1/AllPages/Print>, 17 pages.
"POMALYST® (pomalidomide) capsules, for oral use," [prescribing information], Feb. 2013, 13 pages.
"REVLIMID [lenalidomide] capsules, for oral use," [prescribing information], Jun. 2013, 33 pages.
"Revlimid® (lenalidomide) capsules Data sheet," 22 pages, Apr. 2013.
"ZYTIGA® (abiraterone acetate) Tablets," [prescribing information], Dec. 2012, 9 pages.
Akhtar et al., "Cytochrome b(5) modulation of 17{alpha} hydroxylase and 17-20 lyase (CYP17) activities in steroidogenesis," *J Endocrinol.*, 187(2):267-274, Nov. 2005.
Birder et al., "Altered urinary bladder function in mice lacking the vanilloid receptor TRPV1," *Nat. Neurosci.*, 5(9):856-860, Sep. 2002.
Bley, "Recent developments in transient receptor potential vanilloid receptor 1 agonist-based therapies," Exp. Opin Investig Drugs., 13(11):1445-1456, Nov. 2004.
Bosse et al., "Phase I comparability of recombinant human albumin and human serum albumin," *J.Clin Pharmacol.*, 45(1):57-67, Jan. 2005.
Briggs et al., "An adverse reaction to the administration of disoprofol (Diprivan)," *Anaesthesia*, 37(11):1099-1101, Nov. 1982.
Bruno et al., "Population pharmacokinetics/pharmacodynamics of docetaxel in phase II studies in patients with cancer," *J Clin Oncol.*, 16(1):187-196, Jan. 1998.
Carter and Ho, "Structure of serum albumin," *Adv Protein Chem.*, 45:153-203, 1994.
Caterina et al., "Impaired nociception and pain sensation in mice lacking the capsaicin receptor," *Science*, 288(5464):306-313, Apr. 2000.
Caterina et al., "The capsaicin receptor: a heat-activated ion channel in the pain pathway," *Nature*, 389(6653):816-824, Oct. 23, 1997.
Chen et al., "Human serum albumin from recombinant DNA technology: challenges and strategies," *Biochim Biophys Acta.*, 1830(12):5515-1525, Epub May 3, 2013.
Chen et al., "Removal of fatty acids from serum albumin by charcoal treatment," *J Biol Chem.*, 242(2):173-181, Jan. 25, 1967.
ClinicalTrials.gov Identifier: NCT00783367, "Combination Therapy Using Lenalidomide (Revlimid)—Low Dose Dexamethasone and Rituximab for Treatment of Rituximab-Resistant, Non-Aggressive B-Cell Lymphomas," ClinicalTrials.gov [online] xx [retrieved on Sep. 24, 2014]. Retrieved from the Internet: <URL: https://clinicaltrials.gov/ct2/show/NCT00783367?term=lenalidomide&rank=4>, 5 pages.
ClinicalTrials.gov Identifier: NCT01183663, "Lenalidomide in Combination With Bevacizumab, Sorafenib, Temsirolimus, or 5-Fluorouracil, Leucovorin, Oxaliplatin (FOLFOX)," ClinicalTrials.gov [online] Aug. 11, 2014 [retrieved on Sep. 24, 2014]. Retrieved from the Internet: <URL: https://clinicaltrials.gov/ct2/show/NCT01183663?term=lenalidomide&rank=9>, 5 pages.
ClinicalTrials.gov Identifier: NCT01358734, "A Study Being Conducted at Multiple Locations to Compare the Safety and Effectiveness of Three Different Treatment Regimens; 1) Lenalidomide, 2) Lenalidomide + Azacitidine, or 3) Azacitidine Alone in Newly Diagnosed Acute Myeloid Leukemia in Elderly Subjects ≥ 65 Years of Age," ClinicalTrials.gov [online] Jun. 30, 2014 [retrieved on Sep. 24, 2014]. Retrieved from the Internet: <URL: https://clinicaltrials.gov/ct2/show/NCT01358734?term=lenalidomide&rank=15>, 4 pages.
ClinicalTrials.gov Identifier: NCT01460940, "A Phase II Trial of Panobinostat and Lenalidomide in Patients With Relapsed or Refractory Hodgkin's Lymphoma," ClinicalTrials.gov [online] Jul. 15, 2013 [retrieved on Sep. 24, 2014]. Retrieved from the Internet: <URL: https://clinicaltrials.gov/ct2/show/NCT01460940?term=lenalidomide&rank=13>, 5 pages.
ClinicalTrials.gov Identifier: NCT01704781, "Vacc-4x + Lenalidomide vs. Vacc-4x +Placebo in HIV-1-infected Subjects on Antiretroviral Therapy (ART) (IMID)," ClinicalTrials.gov [online] Jul. 30, 2014[retrieved on Sep. 24, 2014]. Retrieved from the Internet: <URL: https://clinicaltrials.gov/ct2/show/NCT01704781?term=lenalidomide&rank=1>, 4 pages.
Cohn and Strong, "Preparation and properties of serum and plasma proteins; a system for the separation into fractions of the protein and lipoprotein components of biological tissues and fluids," *J Am Chem Soc.*, 68:459-475, Mar. 1946.
Curry et al., "Crystal structure of human serum albumin complexed with fatty acid reveals an asymmetric distribution of binding sites," *Nat Struct Biol.*, 5(9):827-835, Sep. 1998.
Davis et al., "Vanilloid receptor-1 is essential for inflammatory thermal hyperalgesia," *Nature*, 405(6783): 183-187, May 11, 2000.
Di Marzo et al., "Endovanilloid signaling in pain," *Curr. Opin. Neurobiol.*, 12(4):372-379, Aug. 2002.
EMEA, "Scientific Discussion," 42 pages, 2007.
Fehske et al., "The location of drug binding sites in human serum albumin," *Biochem Pharmacol.*, 30(7):687-692, Apr. 1, 1981.
Ferrajoli et al., "Combination therapy with lenalidomide and rituximab in patients with relapsed chronic lymphocytic leukemia (CCL)," Blood, (ASH Annual Meeting Abstracts) 114: Abstract 206, 2 pages, 2009.
Finlayson, "Albumin Products," *Seminars in Thrombosis and Hemostasis*, 6(2):85-120, 1980.
He et al., "Atomic structure and chemistry of human serum albumin," *Nature*, 358(6383):209-215, Jul. 16, 1992.
Hideshima et al., "A review of lenalidomide in combination with dexamethasone for the treatment of multiple myeloma," *Ther Clin Risk Manag.*, 4(1):129-136, Feb. 2008.
Janssen, "ZYTIGA® abiraterone acetate product information," Mar. 1, 2012, 12 pages.
Kasim et al., "Molecular properties of WHO essential drugs and provisional biopharmaceutical classification," *Mol Pharm.*, 1(1):85-96, Jan. 12, 2004.
Kotla et al., "Mechanism of action of lenalidomide in hematological malignancies," *J Hematol. Oncol.*, 2:36, Aug. 12, 2009.
Kragh-Hansen, "Structure and ligand binding properties of human serum albumin," *Dan Med Bull.*, 37(1):57-84, Feb. 1990.
Kratz, "Albumin as a drug carrier: design of prodrugs, drug conjugates and nanoparticles," *J Control Release.*, 132(3):171-183, Epub May 17, 2008.
Kularatne et al., "Synthesis and biological analysis of prostate-specific membrane antigen-targeted anticancer prodrugs," *J Med Chem.*, 53(21):7767-7777, Nov. 11, 2010.
Lin et al., "Stability of human serum albumin during bioprocessing: denaturation and aggregation during processing of albumin paste," *Pharm Res.*, 17(4):391-396, Apr. 2000.
Lipinski, "Drug-like properties and the causes of poor solubility and poor permeability," *J Pharmacol Toxicol Methods*, 44(1):235-249, Jul.-Aug. 2000.
Mezey et al., "Distribution of mRNA for vanilloid receptor subtype 1 (VR1), and VR1-like immunoreactivity, in the central nervous system of the rat and human," *Proc Natl Acad Sci U S A.*, 97(7):3655-3660, Mar. 28, 2000.
Piccart et al., "Docetaxel: an active new drug for treatment of advanced epithelial ovarian cancer," *J Natl Cancer Inst.*, 87(9):676-681, May 3, 1995.
Pomonis et al., "N-(4-Tertiarybutylphenyl)-4-(3-cholorphyridin-2-yl)tetrahydropyrazine-1(-2H)-carbox-amide (BCTC), a novel, orally effective vanilloid receptor 1 antagonist with analgesic properties: II. in vivo characterization in rat models of inflammatory and neuropathic pain," J Pharmacol Exp Ther., 306(1):387-393, Epub. Apr. 29, 2003.
Prijovich et al., "Stability of the new prodrug 9-aminocamptothecin glucuronide (9ACG) in the presence of human serum albumin," Biochem Pharmacol., 66(7):1181-1187, Oct. 1, 2003.
Rajkumar et al., "Combination therapy with lenalidomide plus dexamethasone (Rev/Dex) for newly diagnosed myeloma," *Blood*, 106(13):4050-4053, Epub Aug. 23, 2005.
Ratain, "Flushing oral oncology drugs down the toilet," *J Clin Oncol.*, 29(30):3958-3959, Epub Sep. 19, 2011.

(56) References Cited

OTHER PUBLICATIONS

Samor et al., "The role of polyamine architecture on the pharmacological activity of open lactone camptothecin-polyamine conjugates," *Bioconjug Chem.*, 19(11):2270-2279, Nov. 19, 2008.
Sartor et al., "Novel therapeutic strategies for metastatic prostate cancer in the post-docetaxel setting," *Oncologist.*, 16(11):1487-1497, Epub Nov. 2, 2011.
Schmid et al., "Development of albumin-binding camptothecin prodrugs using a Peptide positional scanning library," *Bioconjug Chem.*, 18(6):1786-1799, Epub Oct. 5, 2007.
Semeraro et al., "Trial Watch: Lenalidomide-based immunochemotherapy," 2(11):e26494. Epub Oct. 21, 2013.
Silverman and Holladay, *The Organic Chemistry of Drug Design and Drug Action*, Elsevier, pp. 29-32, 2004.
Sugio et al., "Crystal structure of human serum albumin at 2.5 A resolution," *Protein Eng.*, 12(6):439-446, Jun. 1999.
Todd et al., "Fast and flawed or scientifically sound: the argument for administering oral oncology drugs during fasting," *J Clin Oncol.*, 30(8):888-889, Epub Feb. 13, 2012.
Trudeau et al., "Docetaxel in patients with metastatic breast cancer: a phase II study of the National Cancer Institute of Canada-Clinical Trials Group," *J Clin Oncol.*, 14(2):422-428, Feb. 1996.
Tullis, "Albumin. 1. Background and use," *JAMA.*, 237(4):355-360, Jan. 24, 1977.
Vannucchi, "Management of myelofibrosis," Hematology Am Soc Hematol Educ Program., 2011:222-230, 2011.
Vorum, "Reversible ligand binding to human serum albumin. Theoretical and clinical aspects," *Dan Med Bull.*, 46(5):379-399, Nov. 1999.
Walker et al., "The VR1 antagonist capsazepine reverses mechanical hyperalgesia in models of inflammatory and neuropathic pain," *J. Pharm. Exp. Ther.*, 304(1): 56-62, Jan. 2003.
International Search Report and Written Opinion for PCT/US2014/14079 dated May 13, 2014, 8 pages.
International Preliminary Report on Patentability for PCT/US2014/014079, dated Aug. 13, 2015, 7 pages.
International Preliminary Report on Patentability of the International Application No. PCT/US2015/38077, dated Jan. 5, 2017, 7 pages.
International Search Report and Written Opinion of the International Application No. PCT/US2015/38077, dated Sep. 24, 2015, 15 pages.
International Preliminary Report on Patentability for PCT/US2015/056900, dated May 4, 2017, 7 pages.
International Search Report and Written Opinion for PCT/US2015/056900, dated Dec. 29, 2015. 13 pages.
Ryan et al., "Structural basis of binding of fluorescent, site-specific dansylated amino acids to human serum albumin," Journal of Structural Biology., 174:84-91, 2011.

\* cited by examiner

SOLUBLE COMPLEXES OF DRUG ANALOGS AND ALBUMIN

CROSS REFERENCE TO RELATED APPLICATION

This application claims the benefit of U.S. Provisional Application Ser. No. 61/760,573, filed Feb. 4, 2013. The disclosure of the prior application is considered part of and is incorporated by reference in the disclosure of this application.

FIELD OF THE INVENTION

The present invention relates to novel soluble complexes of drug analogs and albumin, their methods of preparation and pharmaceutical use.

BACKGROUND OF THE INVENTION

About 30% of drugs that appear on the World Health Organization (WHO) Essential Drug List were reported to be poorly water-soluble, based on the Biopharmaceutics Classification System (BCS). See Kasim, N. A., et al., Molecular properties of WHO essential drugs and provisional biopharmaceutical classification, Molecular Pharmaceutics, 2004, 1(1): p. 85-96. Over 40% of newly developed pharmaceutically active substances have solubility issues. See Lipinski, C. A., Drug-like properties and the causes of poor solubility and poor permeability, Journal of Pharmacological and Toxicological Methods, 2000, 44(1): p. 235-249. The poor dissolution and/or permeability of these drugs often result in low and highly variable bioavailability. A major obstacle of successfully commercializing these compounds is the difficulty of enhancing their dissolution rate and extent of dissolution.

For example, Camptothecin is a well-known, poorly soluble, alkaloid that was first isolated in 1966 from *Camptotheca acuminate*. Camptothecin shows strong cytotoxic activity and anti-tumor activity. Due to its poor water solubility (2.5 ug/mL), the first clinical trials in the early seventies were performed using CPT as the sodium salt of the hydroxycarboxylate form, with an open E-ring. However, severe and unpredictable side effects hindered further clinical development.

A renewed interest in CPT and CPT derivatives came with the elucidation of their mechanism of action, i.e. inhibition of the nuclear enzyme topoisomerase I. It was also discovered that the lactone ring of CPT is necessary for specific interaction with topoisomerase I and selective antitumor activity. Several derivatives of CPT with improved solubility and lactone ring stability have been synthesized, including irinotecan and topotecan (which have been FDA approved for clinical use in the therapy of colorectal, ovarian and lung cancer), as well as SN-38, 9-Aminocamptothecin, 9-Nitrocamptothecin, GI-147211, Exatecan and Karenitecin. See Table 1. The clinical application of these drugs is, however, limited by their toxic, dose-related side effects, such as myelosuppression, gastrointestinal disorders and stomatitis.

TABLE 1

Well-known CPT derivatives.

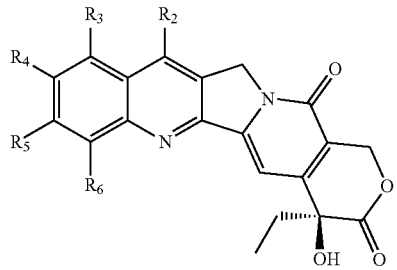

| Compound | $R_2$ | $R_3$ | $R_4$ | $R_5$ | $R_6$ |
|---|---|---|---|---|---|
| Camptothecin | —H | —H | —H | —H | —H |
| Topotecan | —H | —CH$_2$N(CH$_3$)$_2$ | —OH | —H | —H |
| Irinotecan | —CH$_2$CH$_3$ | —H | —O—C(=O)—N(piperidinyl-piperidine) | —H | —H |
| SN-38 | —CH$_2$CH$_3$ | —H | —OH | —H | —H |
| 9-Aminocamptothecin | —H | —NH$_2$ | —H | —H | —H |
| 9-Nitrocamptothecin | —H | —NO$_2$ | —H | —H | —H |
| GI-147211 | —CH$_2$—N(piperazinyl)—CH$_3$ | —H | —OCH$_2$CH$_2$O— | | —H |
| Exatecan | —CH(NH$_2$)—CH$_2$—CH$_2$— | | —CH$_3$ | —F | —H |
| Karenitecin | —H | —CH$_2$CH$_2$Si(CH$_3$)$_3$ | —H | —H | —H |

Furthermore, attempts have been made to selectively bind a biologically active, lactone form of a CPT derivative to HSA, in order to prevent HSA from preferentially binding and stabilizing the inactive carboxy form of the CPT derivative, thereby driving the lactone ring/open-ring carboxy blood equilibrium toward the active lactone ring form. However, these attempts have been only partially successful. For instance, in Z. M. Prijovich et al., *Biochem. Pharm.* 66 (2003): 1181-1187, 9-Aminocamptothecin glucuronide (9AGC) shows improved stability of the active lactone ring form in blood, reaching equilibrium in blood of about 20% lactone ring form and a blood half-life increased to about 50 minutes.

Accordingly, there is a clear and continuing need to create more soluble forms of poorly soluble drugs, such as camptothecin.

SUMMARY OF THE INVENTION

It is thus an object of the present invention to provide water-soluble formulations of poorly soluble drugs by forming a non-covalently bound complex of serum albumin with an analog of the drug containing a serum albumin binding moiety. It is a further object of the present invention to provide an aqueous formulation of a non-covalently bound complex of serum albumin with an analog of a poorly soluble drug containing a serum albumin binding moiety. It is another object of the present invention to provide an aqueous formulation of a non-covalently bound complex of serum albumin with an analog of a poorly soluble drug containing a serum albumin binding moiety, wherein the non-covalently bound complex has a solubility in aqueous solution of at least 5 mg/ml, is substantially free of solvents other than water and is optically clear without the need for filtration. It is another object of the invention to provide water-soluble formulations of poorly soluble camptothecin analogs containing a group that selectively binds serum albumin, by forming a non-covalently bound complex of the camptothecin analog with serum albumin. It is a further object of the invention to provide an aqueous formulation of a non-covalently bound complex of serum albumin with a poorly soluble camptothecin analog containing a group that selectively binds serum albumin. It is another object of the present invention to provide an aqueous formulation of a non-covalently bound complex of serum albumin with a poorly soluble camptothecin analog containing a group that selectively binds serum albumin, wherein the non-covalently bound complex has a solubility in aqueous solution of at least 5 mg/ml, is substantially free of solvents other than water and is optically clear without the need for filtration. It is a further object of the present invention to provide methods of treating mammalian cell proliferative disorders using these water-soluble formulations of a non-covalently bound complex of the camptothecin analog with serum albumin.

The present invention provides a non-covalently bound complex having a solubility in aqueous solution of at least 5 mg/ml, wherein the complex is formed of serum albumin and an analog of a drug, wherein the drug has at least one alcohol, thiol, primary amine or secondary amine group, and the analog of the drug comprises a linker-serum-albumin-binding-moiety substituted for the alcohol, thiol, primary amine or secondary amine group, wherein the linker-serum-albumin-binding-moiety comprises:

wherein

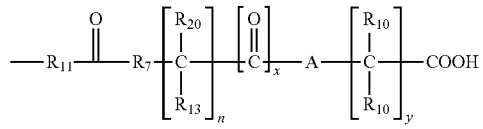

$R_{11}$ is: O, if the linker-serum-albumin-binding-moiety substitutes for an alcohol group on the drug,
S, if the linker-serum-albumin-binding-moiety substitutes for a thiol group on the drug,
NH, if the linker-serum-albumin-binding-moiety substitutes for primary amine group on the drug, or

if the linker-serum-albumin-binding-moiety substitutes for a secondary amine group on the drug;
$R_7$ is a covalent bond, if $R_{11}$ is S; otherwise, $R_7$ is selected from the group consisting of O, NH and a covalent bond;
A is

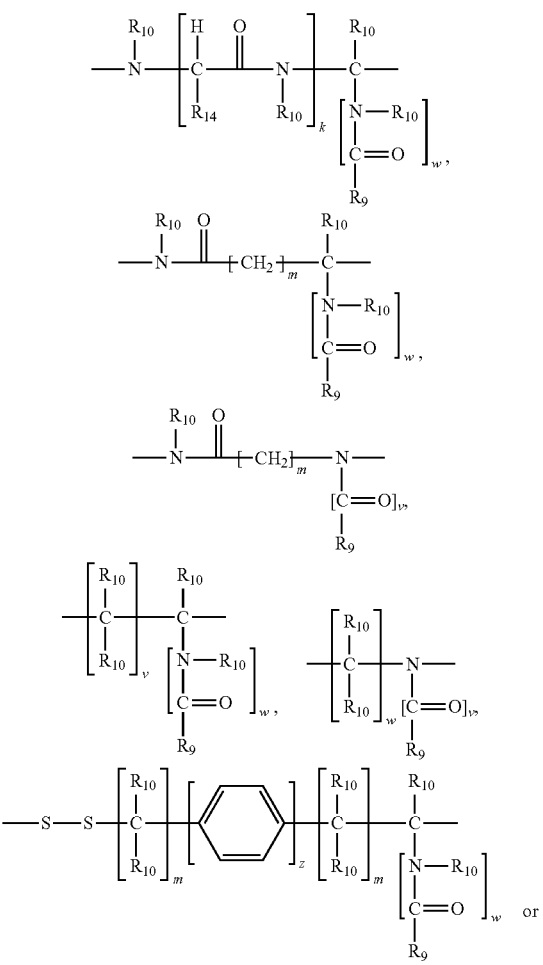

-continued

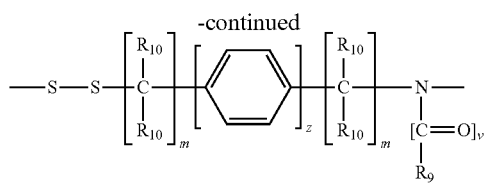

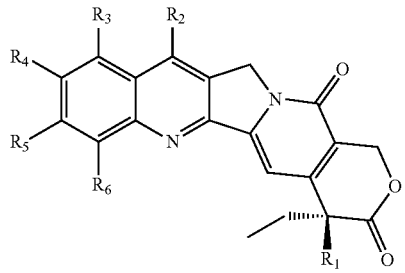

$R_9$ is an unbranched or branched alkyl, alkylene or alkyne of 2 to 30 carbon atoms optionally including one or more ring structures of 3 to 6 atoms when $R_9$ has at least 7 carbon atoms, including heteroatoms of oxygen in an integer number from 0 to one fifth the total number of carbon atoms in $R_9$, and optionally substituted with with up to three groups selected from the groups consisting of halo, nitro, amine, amide, hydroxyl, O-lower alkyl and carboxy; with the proviso that there be no covalent bonds between oxygen atoms in $R_9$;

$R_{10}$ is, independently in each instance, H or lower alkyl;

$R_{13}$ is, independently in each instance, H, OH, $NO_2$, $NH_2$, $NH_3^+$, SH or a branched or unbranched alkyl, alkylene or alkyne of 1 to 8 carbon atoms, wherein the alkyl, alkylene or alkyne is optionally substituted with one or two substituents selected from the group consisting of halo, OH, $NO_2$, $NH_2$, $NH_3^+$, SH and =O, and optionally includes up to two heteroatoms independently selected from O, S and N, with the proviso that no O, S or N atom in the alkyl, alkylene or alkyne is covalently bonded to any other O, S or N atom;

$R_{14}$ is, independently in each instance, H, OH, $NO_2$, $NH_2$, $NH_3^+$, SH or a branched or unbranched alkyl, alkylene or alkyne of 1 to 10 carbon atoms, wherein the alkyl, alkylene or alkyne optionally includes one or more ring structures of 3 to 9 atoms, is optionally substituted with one or two substituents selected from the group consisting of halo, OH, $NO_2$, $NH_2$, $NH_3^+$, SH and =O, and optionally includes up to two heteroatoms independently selected from O, S and N, with the proviso that no O, S or N atom in the alkyl, alkylene or alkyne is covalently bonded to any other O, S or N atom;

$R_{20}$ is, independently in each instance, H or lower alkyl and two $R_{20}$ may optionally together form a ring structure of up to 8 carbon atoms;

k is 0, 1 or 2;

m, independently in each instance, is 0, 1, 2 or 3;

n is an integer from 1 to 8;

v is 0 or 1;

w is 0 or 1;

x is 0 or 1, with the proviso that x is 0 when a di-sulfide bond is present in A;

y is 0, 1, 2 or 3; and z is 0 or 1, wherein the non-covalently bound complex has a molar ratio of the analog of the drug to serum albumin from about 1:1 to about 16:1.

The present invention provides a non-covalently bound complex of a camptothecin analog and serum albumin in a molar ratio from about 1:1 to about 16:1, wherein:

the complex has a solubility in aqueous solution of at least 5 mg/ml, and the camptothecin analog comprises a compound of Formula I:

wherein $R_1$ is OH or OX, wherein X comprises a group that selectively binds serum albumin;

$R_{2-6}$ are each, independently, H, halo, OH, $NO_2$ $NH_2$, lower alkyl, O-lower alkyl, NH-lower alkyl, N(lower alkyl)$_2$, lower alkyl-N(lower alkyl)$_2$, lower alkyl-Si (lower alkyl)$_3$,

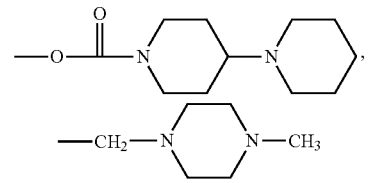

or comprises a group that selectively binds serum albumin;

wherein $R_4$ and $R_5$ optionally, together form —OCH$_2$CH$_2$O—, $R_2$ and $R_3$ optionally, together form

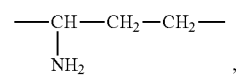

and at least one of $R_1$, $R_2$, $R_3$, $R_4$, $R_5$, and $R_6$ comprises a group that selectively binds serum albumin.

The present invention also provides therapeutic methods of administering the above non-covalently bound complex of a camptothecin analog of Formula I for the treatment of proliferative disorders, such as cancer. The present invention further provides therapeutic methods of administering the above non-covalently bound complex of a camptothecin analog of Formula I for the treatment of diseases responding to inhibition of Topoisomerase I, such as tumors, HIV infections and parasitic infections.

DETAILED DESCRIPTION

General Definitions

Figure 1:
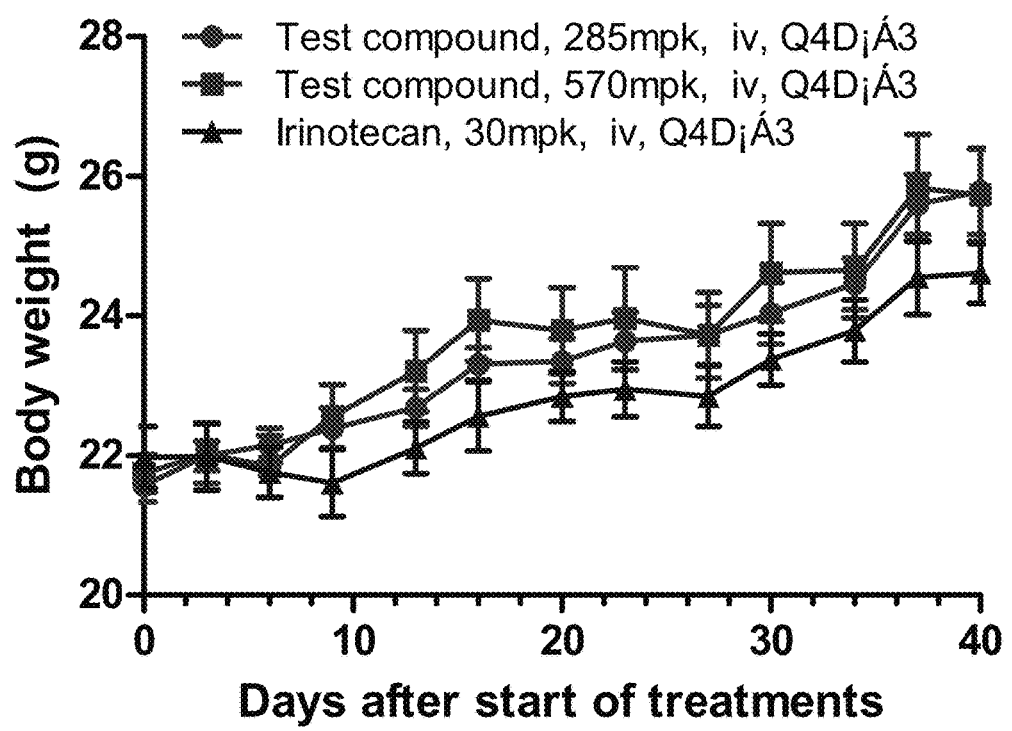
FIG. 1 is a line plot showing body weight changes of the mice treated with test compound and irinotecan in the different groups.

The following definitions refer to the various terms used above and throughout the disclosure.

The term "halo" refers to fluoro, chloro, bromo or iodo.

The term "alkyl" refers to a straight or branched chain alkyl group, having from 1-30 carbon atoms. Illustrative of the alkyl group include the methyl, ethyl, propyl, isopropyl, butyl, isobutyl, sec-butyl, t-butyl, pentyl, 3-methylbutyl, 2,2-dimethylpropyl, 1,1-dimethylpropyl, hexyl, 1-methylpentyl, 4-methylpentyl, heptyl, 1-methylhexyl, 2-methylhexyl, 5-methylhexyl, 3-ethylpentyl, octyl, 2-methylheptyl, 6-methylheptyl, 2-ethylhexyl, 2-ethyl-3-methylpentyl, 3-ethyl-2-methylpentyl, nonyl, 2-methyloctyl, 7-methyloctyl, 4-ethylheptyl, 3-ethyl-2-methylhexyl, 2-ethyl-1-methylhexyl, decyl, 2-methylnonyl, 8-methylnonyl, 5-ethyloctyl, 3-ethyl-2-methylheptyl, 3,3-diethylhexyl, undecyl, 2-methyldecyl, 9-methyldecyl, 4-ethylnonyl, 3,5-dimethylnonyl, 3-propyloctyl, 5-ethyl-4-methyloctyl, I-pentylhexyl, dodecyl, 1-methylundecyl, 10-methylundecyl, 3-ethyldecyl, 5-propylnonyl, 3,5-diethyloctyl, tridecyl, 11-methyldodecyl, 7-ethylundecyl, 4-propyldecyl, 5-ethyl-3-methyldecyl, 3-pentyloctyl, tetradecyl, 12-methyltridecyl, 8-ethyldodecyl, 6-propylundecyl, 4-butyldecyl, 2-pentylnonyl, pentadecyl, 13-methyltetradecyl, 10-ethyltridecyl, 7-propyldodecyl, 5-ethyl-3-methyldodecyl, 4-pentyldecyl, 1-hexylnonyl, hexadecyl, 14-methylpentadecyl, 6-ethyltetradecyl, 4-propyltridecyl, 2-butyldodecyl, heptadecyl, 15-methylhexadecyl, 7-ethylpentadecyl, 3-propyltetradecyl, 5-pentyldodecyl, octadecyl, 16-methylheptadecyl, 5-propylpentadecyl, nonadecyl, 17-methyloctadecyl, 4-ethylheptadecyl, icosyl, 18-methylnonadecyl, 3-ethyloctadecyl, henicosyl, docosinyl, tricosinyl, tetracosinyl and pentacosinyl groups.

The term "alkylene" represents an alkenyl group, having from 2 to 30 carbon atoms, and may be a straight or branched chain group. It may have 1 or more, preferably from 2 to 6, double bonds. Examples of such groups include the vinyl, alkyl, 1-propenyl, isopropenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 1-octenyl, 8-nonenyl, 1-nonenyl, 1-decenyl, 9-decenyl, 8-tridecenyl, cis-8-pentadecenyl, trans-8-pentadecenyl, 8-heptadecenyl, 8-heptadecenyl, 8,11-heptadecadienyl, 8,11,14-heptadecatrienyl, 4,7,11,14-nonadecatetraenyl and 2,6-dimethyl-8-(2,6,6-trimethyl-1-cyclohexen-1-yl)-1,3,5,7-nonatetraen-1-yl, cis-10-nonadecaenyl, 10,13-nonadecadienyl, cis-7,10,13-nonadecatrienyl, 5,8,11,14-nonadecatetraenyl, nonadecapentaenyl, henecosatetraenyl, henecosapentaenyl, henecosahexaenyl, myristyl, and eicosyl groups.

The term "alkyne" represents and alkynyl group, having from 2 to 30 carbon atoms, and may be a straight or branched chain group. In addition to one or more triple bonds, the alkyne group may have one or more double bonds.

When specifically stated, alkyl, alkylene or alkyne groups may include ring structures of 3 to 8 carbon atoms.

When an alkyl, alkylene or alkyne group is described as a "lower" alkyl, alkylene or alkyne group, it has a maximum of 6 carbon atoms.

When specifically stated, alkyl, alkylene or alkyne groups may include heteroatoms of oxygen, sulfur, nitrogen and/or silicon. Where specifically stated, alkyl, alkylene or alkyne groups may be substituted with halo, hydroxyl, nitro, amine, amide, sulfhydryl, O-lower alkyl and carboxy groups. Illustrative examples of the alkyl group substituted with oxygen or including a heteroatom of oxygen include methoxymethyl, ethoxymethyl, propoxymethyl, n-butoxymethyl, 2-methoxyethyl, 2-ethoxyethyl, 2-propoxyethyl, 3-methoxypropyl, 3-ethoxypropyl, 3-propoxypropyl, 4-methoxybutyl, 4-propoxybutyl, dimethoxymethyl, 2,2-dimethoxyethyl, diethoxymethyl, 2,2-diethoxyethyl, dipropoxymethyl and 2,2-dipropoxyethyl groups. Illustrative examples of the alkyl group substituted with sulfur are methylthiomethyl, ethylthiomethyl, propylthiomethyl, n-butylthiomethyl, 2-methylthiolethyl, 2-ethylthiolethyl, 2-propylthiolethyl, 3-methylthiopropyl, 3-ethylthiopropyl, 3-propylthiopropyl, 4-methylthiobutyl, and 4-propylthiobutyl groups. Illustrative examples of the alkyl group substituted with nitrogen are aminomethyl, dimethylaminomethyl, (N-acetyl)methylaminomethyl, diethylaminomethyl, dipropylaminomethyl, dibutylaminomethyl, dimethylaminoethyl, diethylaminoethyl, dipropylaminoethyl, and dibutylaminoethyl groups. Illustrative examples of the alkyl group substituted with silicon are trimethylsilyl, triethylsilyl, tributylsilyl, t-butyldimethylsilyl, t-butyldiethylsilyl and t-butyldiphenylsilyl.

The term "group of natural amino acid side chains" represents the set of chemical groups attached to the alpha carbon for each of the twenty naturally-occurring amino acids: Cysteine, Histidine, Isoleucine, Methionine, Serine, Valine, Alanine, Glycine, Leucine, Proline, Threonine, Phenylalanine, Arginine, Tyrosine, Tryptophan, Aspartic Acid, Asparagine, Glutamic Acid, Glutamine and Lysine.

A "pharmaceutically acceptable salt" includes a salt with an inorganic base, organic base, inorganic acid, organic acid, or basic or acidic amino acid. Salts of inorganic bases include, for example, alkali metals such as sodium or potassium; alkaline earth metals such as calcium and magnesium or aluminum; and ammonia. Salts of organic bases include, for example, trimethylamine, triethylamine, pyridine, picoline, ethanolamine, diethanolamine, and triethanolamine. Salts of inorganic acids include for example, hydrochloric acid, hydroboric acid, nitric acid, sulfuric acid, and phosphoric acid. Salts of organic acids include for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Salts of basic amino acids include, for example, arginine, lysine and ornithine. Acidic amino acids include, for example, aspartic acid and glutamic acid.

As used herein, the term "cancer" refers to all known forms of cancer including, solid forms of cancer (e.g., tumors), lymphomas, and leukemias.

As used herein, "anti-neoplastic agent" or "anti-cancer agent" or "anti-tumor agent" refer to an agent that reduces, prevents, mitigates, limits, and/or, delays the deleterious physiological manifestations, the growth or metastases of neoplasms, or by killing neoplastic cells directly by necrosis or apoptosis of neoplasms or any other mechanism.

As used herein, an "effective amount" or a "pharmaceutically-effective amount" in reference to the compounds or compositions of the instant invention refers to the amount sufficient to induce a desired biological, pharmacological, or therapeutic outcome in a subject. That result can be reduction, prevention, mitigation, delay, shortening the time to resolution of, alleviation of the signs or symptoms of, or exert a medically-beneficial effect upon the underlying pathophysiology or pathogenesis of an expected or observed side-effect, toxicity, disorder or condition, or any other desired alteration of a biological system. In cancer treatment, the result will generally include the reduction, prevention, mitigation, limitation, and/or, delay of the deleterious physiological manifestations, growth or metastases of neoplasms.

As used herein, "solubility in aqueous solution of at least X mg/ml" refers to a composition that forms an optically clear solution at room temperature in water, without need for filtration or additional, non-water, solvents.

As used herein, "substantially free of solvent", in reference to an aqueous solution, refers to an aqueous solution that contains less than 0.5%, by weight, of any non-water solvent.

As used herein, "a group that selectively binds to serum albumin" refers to a chemical group suitable for administration to a mammal, preferably human, which exhibits binding affinity for serum albumin. Examples of such groups that selectively bind to serum albumin include, but are not limited to, long chain fatty acids ($C_{16}$-$C_{20}$; including oleic, palmitic, linoleic, stearic, arachidonic, and palmitoleic); medium chain fatty acids ($C_6$-$C_{14}$; including caprylate or octanoate); phospholipids (lysolecithins, oleoyllysophosphatidic acid, phosphatidylcholine, phosphatidylethanolamine); eicosanoid derivatives (leukotrienes, thromboxanes, prostaglandins A, E, F, and I); steroid hormones (cholesterol, testosterone, pregnenolone, cortisol, androsterone, indol, progesterone, estrogen); vitamin D (both monohydroxyvitamin D and dihydroxyvitamin D); bile salts (lithocholate, chenodeoxycholate, deoxycholate, ursodeoxycholate, cholate, glycolitocholate, glycochenodeoxycholate, taurochenodoxycholate, glycodeoxycholate, glycocholate, taurocholate); bilirubins (bilirubin, biliverdin, xanthobilirubin, EZ-cyclobilirubin, 6-bilirubin); porphyrins (hematin, protoporphyrin); warfarin; salicylates, ibuprofen; prednisone; iophenoxate; sulfisoxazole; phenylbutazone; oxphenylbutazone; digitoxin; indomethacin; tolbutamide; furosemide; phenyloin; chlorpropamide; chlorthiazide; the penicillins (including oxacillin, benzylpenicillin); acetotrizoate; isulfobromophthalein; deacetylcolchicine; dansylamide; dansylglutamine; dansylsarcosine; indomethacin; phenylpropazone; azobenzene derivatives; sulfobromophthalein; triiodobenzoate; benzodiazepine (including diazepam); flufenamate; iopanoate; ethacrynate; panproxen; clofibrate; L-tryptophan; N-acetyl-L-tryptophan; 6-methyltryptophan; thyroxine; 3,5,3'-L-triiodothyronine; indole propionate; kynurenine; ethacrynate; panproxen; chlorophenoxyisobutyrate; 3' azido-3'-deoxythymidine; non-steroidal anti-inflammatory agents containing ionized carboxyl groups; gossypol; meso-2,3-dimercaptosuccinic acid; captopril; N2-mercaptoethyl-1,2-diaminopropane; disulfuramacetaminophen, dis-dichlorodiamineplatinum 9II; pyridoxal 5'-phosphate; aquocobalamin form of vitamin B12; folate; ascorbate (and its oxidation product dehydroascorbate); melatonin; α-melanotropin; gastrin; corticotropin and methotrexate. The group that selectively binds to serum albumin may bind to serum albumin at specific, defined sites, as detailed by crystallographic and displacement studies, and may also bind serum albumin at non-specific sites that have yet to be clearly defined. Binding between the group that selectively binds serum albumin and serum albumin occurs by non-covalent mechanisms. These groups "selectively" bind serum albumin in that when added to mammalian blood, they bind in greatest quantity to serum albumin over other blood proteins. One of skill in the art of pharmacology is well able to envision and use a wide variety of groups that selectively bind serum albumin due to their familiarity with the literature showing many pharmaceutical compounds which preferentially bind serum albumin in mammals. See, for example F. Katz, et al, Journal of Controlled Release, (2008) 132:171-183. One of skill in the art may also use the HSA-binding assay described below as a tool to evaluate the serum albumin binding capacity of any pharmaceutically acceptable chemical group.

In one particular embodiment of the invention, a non-covalently bound complex of a camptothecin analog and serum albumin in a molar ratio from about 1:1 to about 16:1 is provided, wherein:
the complex has a solubility in aqueous solution of at least 5 mg/ml, and
the camptothecin analog comprises a compound of Formula I:

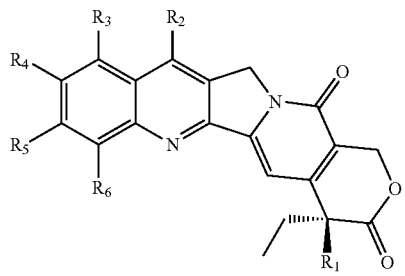

wherein
$R_1$ is OH or —OX, wherein X comprises a group that selectively binds serum albumin;
$R_{2-6}$ are each, independently, H, halo, OH, $NO_2$, $NH_2$, lower alkyl, O-lower alkyl, NH-lower alkyl, N(lower alkyl)$_2$, lower alkyl-N(lower alkyl)$_2$, lower alkyl-Si (lower alkyl)$_3$,

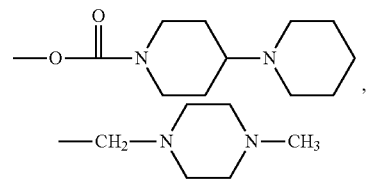

or
comprises a group that selectively binds serum albumin;
wherein $R_4$ and $R_5$ optionally, together form —OCH$_2$CH$_2$O—,
$R_2$ and $R_3$ optionally, together form —CH—CH$_2$—CH$_2$—

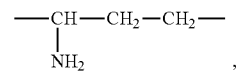

and
at least one of $R_1$, $R_2$, $R_3$, $R_4$, $R_5$, and $R_6$ comprises a group that selectively binds serum albumin.

In another particular embodiment of the invention, a non-covalently bound complex is provided, comprising:
serum albumin, and
an analog of a drug, wherein the drug has at least one alcohol, thiol, primary amine or secondary amine group, and the analog of the drug comprises a linker-serum-albumin-binding-moiety substituted for the alcohol, thiol, primary amine or secondary amine group, wherein the linker-serum-albumin-binding-moiety comprises:

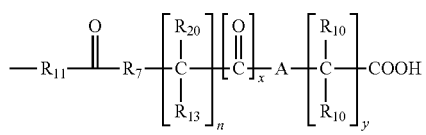

wherein
$R_{11}$ is: O, if the linker-serum-albumin-binding-moiety substitutes for an alcohol group on the drug,
S, if the linker-serum-albumin-binding-moiety substitutes for a thiol group on the drug, NH, if the linker-serum-albumin-binding-moiety substitutes for $$\begin{array}{c}\diagdown\\ \diagup\end{array}\!\!N,$$

primary amine group on the drug, or
if the linker-serum-albumin-binding-moiety substitutes for a secondary amine group on the drug;

$R_7$ is a covalent bond, if $R_{11}$ is S; otherwise, $R_7$ is selected from the group consisting of O, NH and a covalent bond;

A is $$-\!\!\!\overset{R_{10}}{\underset{|}{N}}\!\!-\!\!\left[\overset{H}{\underset{R_{14}}{\overset{|}{C}}}\!\!-\!\!\overset{O}{\overset{\|}{C}}\!\!-\!\!\overset{|}{\underset{R_{10}}{N}}\right]_k\!\!\left[\overset{R_{10}}{\underset{|}{C}}\!\!-\!\!\left[\overset{|}{\underset{C=O}{N-R_{10}}}\right]_w\right.$$

$$-\!\!\!\overset{R_{10}}{\underset{|}{N}}\!\!-\!\!\overset{O}{\overset{\|}{C}}\!\!+\!\!CH_2\!\!\mathord{\text{--}}_m\!\!-\!\!\overset{|}{C}\!\!-\!\!\left[\overset{|}{\underset{C=O}{N-R_{10}}}\right]_w \quad -\!\!\!\overset{R_{10}}{\underset{|}{N}}\!\!-\!\!\overset{O}{\overset{\|}{C}}\!\!+\!\!CH_2\!\!\mathord{\text{--}}_m\!\!-\!\!N\!\!-\!\!\left[C\!\!=\!\!O\right]_v$$

$$+\!\!\!\left[\overset{R_{10}}{\underset{R_{10}}{\overset{|}{C}}}\right]_v\!\!\left[\overset{R_{10}}{\underset{|}{C}}\!\!-\!\!\left[\overset{|}{\underset{C=O}{N-R_{10}}}\right]_w\right. \quad +\!\!\!\left[\overset{R_{10}}{\underset{R_{10}}{\overset{|}{C}}}\right]_w\!\!\left[\overset{|}{\underset{[C=O]_v}{N-}}\right]$$

$$-S\!\!-\!\!S\!\!-\!\!\left[\overset{R_{10}}{\underset{R_{10}}{\overset{|}{C}}}\right]_m\!\!\left[\!\!\!\begin{array}{c}\\ \diagdown\\ \diagup\end{array}\!\!\!\right]_z\!\!\left[\overset{R_{10}}{\underset{R_{10}}{\overset{|}{C}}}\right]_m\!\!\left[\overset{|}{\underset{C=O}{N-R_{10}}}\right]_w \text{ or}$$

$$-S\!\!-\!\!S\!\!-\!\!\left[\overset{R_{10}}{\underset{R_{10}}{\overset{|}{C}}}\right]_m\!\!\left[\!\!\!\begin{array}{c}\\ \diagdown\\ \diagup\end{array}\!\!\!\right]_z\!\!\left[\overset{R_{10}}{\underset{R_{10}}{\overset{|}{C}}}\right]_m\!\!\left[\overset{|}{\underset{[C=O]_v}{N-}}\right]$$

$R_9$ is an unbranched or branched alkyl, alkylene or alkyne of 2 to 30 carbon atoms optionally including one or more ring structures of 3 to 6 atoms when $R_9$ has at least 7 carbon atoms, including heteroatoms of oxygen in an integer number from 0 to one fifth the total number of carbon atoms in $R_9$, and optionally substituted with with up to three groups selected from the groups consisting of halo, nitro, amine, amide, hydroxyl, O-lower alkyl and carboxy; with the proviso that there be no covalent bonds between oxygen atoms in $R_9$;

$R_{10}$ is, independently in each instance, H or lower alkyl;

$R_{13}$ is, independently in each instance, H, OH, $NO_2$, $NH_2$, $NH_3^+$, SH or a branched or unbranched alkyl, alkylene or alkyne of 1 to 8 carbon atoms, wherein the alkyl, alkylene or alkyne is optionally substituted with one or two substituents selected from the group consisting of halo, OH, $NO_2$, $NH_2$, $NH_3^+$, SH and =O, and optionally includes up to two heteroatoms independently selected from O, S and N, with the proviso that no O, S or N atom in the alkyl, alkylene or alkyne is covalently bonded to any other O, S or N atom;

$R_{14}$ is, independently in each instance, H, OH, $NO_2$, $NH_2$, $NH_3^+$, SH or a branched or unbranched alkyl, alkylene or alkyne of 1 to 10 carbon atoms, wherein the alkyl, alkylene or alkyne optionally includes one or more ring structures of 3 to 9 atoms, is optionally substituted with one or two substituents selected from the group consisting of halo, OH, $NO_2$, $NH_2$, $NH_3^+$, SH and =O, and optionally includes up to two heteroatoms independently selected from O, S and N, with the proviso that no O, S or N atom in the alkyl, alkylene or alkyne is covalently bonded to any other O, S or N atom;

$R_{20}$ is, independently in each instance, H or lower alkyl and two $R_{20}$ may optionally together form a ring structure of up to 8 carbon atoms;

k is 0, 1 or 2;
m, independently in each instance, is 0, 1, 2 or 3;
n is an integer from 1 to 8;
v is 0 or 1;
w is 0 or 1;
x is 0 or 1, with the proviso that x is 0 when a di-sulfide bond is present in A;
y is 0, 1, 2 or 3; and
z is 0 or 1, wherein the non-covalently bound complex has a molar ratio of the analog of the drug to serum albumin from about 1:1 to about 16:1 and has a solubility in aqueous solution of at least 5 mg/ml.

In a particular embodiment of the invention, the non-covalently bound complex is defined as one of the other particular embodiments and the serum albumin is human serum albumin.

In another particular embodiment of the invention, the non-covalently bound complex is defined as one of the other particular embodiments, and is in a solid formulation.

In a further particular embodiment of the invention, the non-covalently bound complex is defined as one of the other particular embodiments, and is in an aqueous formulation.

In another particular embodiment of the invention, the non-covalently bound complex is defined as one of the other particular embodiments, and is in an aqueous formulation substantially free of solvents other than water.

In a further particular embodiment of the invention, the non-covalently bound complex is defined as one of the other particular embodiments, and is in an aqueous solution that contains less than 0.1%, by weight, of any non-water solvent.

In another particular embodiment of the invention, the non-covalently bound complex is defined as one of the other particular embodiments, and is in an aqueous solution that contains less than 0.01%, by weight, of any non-water solvent In another particular embodiment of the invention, the non-covalently bound complex is defined as one of the other particular embodiments, and is in an aqueous formulation free of solvents other than water.

In a further particular embodiment of the invention, the non-covalently bound complex is defined as one of the other particular embodiments, and the complex has a solubility in aqueous solution of at least 10 mg/ml, or in another particular embodiment, of at least 20 mg/ml.

In another particular embodiment of the invention, the non-covalently bound complex is defined as one of the other particular embodiments, and the molar ratio of camptothecin analog to human serum albumin is greater than 2:1, optionally greater than 4:1, optionally greater than 5:1, optionally greater than 6:1, and optionally greater than 8:1.

In a further particular embodiment of the invention, the non-covalently bound complex is defined as one of the other particular embodiments, and the 2 drug analog is a compound of Formula I:

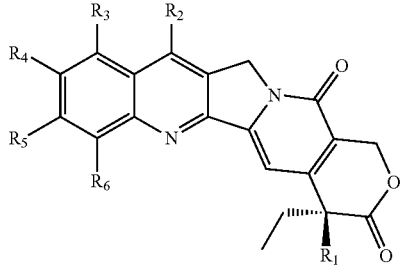

wherein
$R_1$ is OH or linker-serum-albumin-binding-moiety wherein $R_{11}$ is O;
$R_{2-6}$ are each, independently, H, halo, OH, $NO_2$, $NH_2$, lower alkyl, O-lower alkyl, NH-lower alkyl, N(lower alkyl)$_2$, lower alkyl-N(lower alkyl)$_2$, lower alkyl-Si(lower alkyl)$_3$,

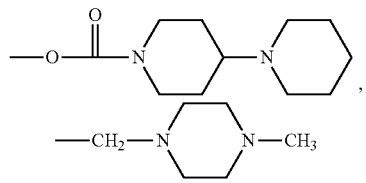

or linker-serum-albumin-binding-moiety;
wherein $R_4$ and $R_5$ optionally, together form $-OCH_2CH_2O-$,
$R_2$ and $R_3$ optionally, together form

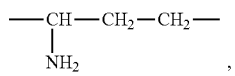

and
if $R_1$ is OH, then at least one of $R_{2-6}$ must be linker-serum-albumin-binding-moiety; and the linker-serum-albumin-binding-moiety is

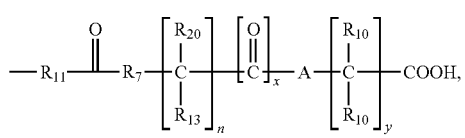

as defined above.

In another particular embodiment of the invention, the non-covalently bound complex is defined as one of the other particular embodiments, and the drug is selected from the group consisting of camptothecin, topotecan, irinotecan, SN-38, 9-aminocamptothecin, 9-nitrocamptothecin, GI-147211, Exatecan, and Karenitecin.

In a further particular embodiment of the invention, the non-covalently bound complex is defined as one of the other particular embodiments, and the drug analog is a compound of Formula I, wherein $R_2$ is $-CH_2CH_3$; $R_3$ is $-H$, $R_4$ is

$R_5$ is H; $R_6$ is H and $R_1$ is

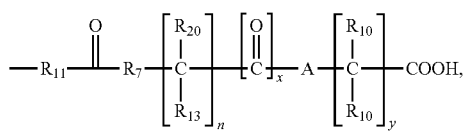

as defined above, wherein $R_{11}$ is O.

In another particular embodiment of the invention, the non-covalently bound complex is defined as one of the other particular embodiments, and the drug analog is a compound of Formula I, wherein $R_2$ is H; $R_3$ is

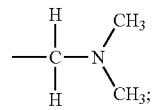

$R_4$ is $-OH$ or linker-HSA binding moiety; $R_5$ is H; $R_6$ is H; $R_1$ is $-OH$ or linker-HSA binding moiety; at least one of $R_1$ and $R_4$ must be linker-HSA binding moiety, wherein the linker-HSA binding moiety is

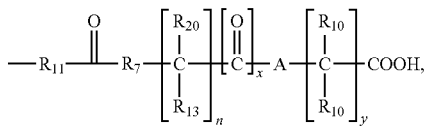

as defined above, wherein $R_{11}$ is O.

In a further particular embodiment of the invention, the non-covalently bound complex is defined as one of the other particular embodiments, and the drug analog is a compound of Formula I, wherein $R_2$ is $-CH_2CH_3$; $R_3$ is H; $R_4$ is $-OH$ or linker-HSA binding moiety; $R_5$ is H; $R_6$ is H; $R_1$ is $-OH$ or linker-HSA binding moiety; at least one of $R_1$ and $R_4$ must be linker-HSA binding moiety, wherein the linker-HSA binding moiety is

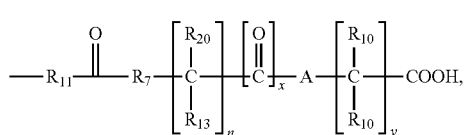

as defined above,
wherein $R_{11}$ is O.

In another particular embodiment of the invention, the non-covalently bound complex is defined as one of the other particular embodiments, and the linker-HSA binding moiety is:

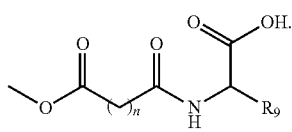

In a further particular embodiment of the invention, the non-covalently bound complex is defined as one of the other particular embodiments, and $R_9$ is an unbranched or branched alkyl, alkylene or alkyne of 3 to 30 carbon atoms optionally including one or more ring structures of 3 to 6 atoms.

In another particular embodiment of the invention, the non-covalently bound complex is defined as one of the other particular embodiments, and $R_9$ is an unbranched or branched alkyl, alkylene or alkyne of 4 to 24 carbon atoms optionally including one or more ring structures of 3 to 6 atoms.

In a further particular embodiment of the invention, the non-covalently bound complex is defined as one of the other particular embodiments, and $R_9$ is an unbranched or branched alkyl, alkylene or alkyne of 4 to 12 carbon atoms optionally including one or more ring structures of 3 to 6 atoms.

In a further particular embodiment of the invention, the non-covalently bound complex is defined as one of the other particular embodiments, and the drug analog is:

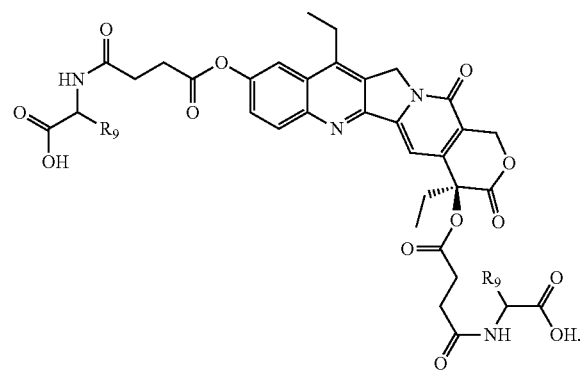

In another particular embodiment of the invention, the non-covalently bound complex is defined as one of the other particular embodiments, and the drug analog is:

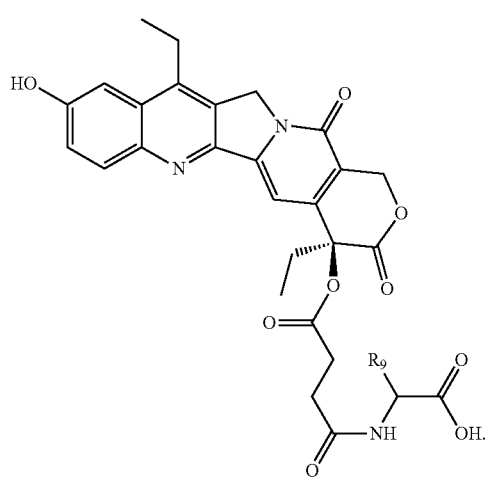

In a further particular embodiment of the invention, the non-covalently bound complex is defined as one of the other particular embodiments, and the drug analog is:

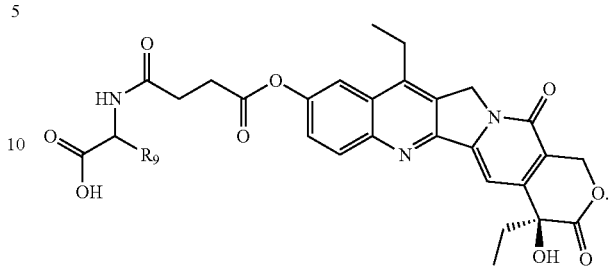

In another particular embodiment of the invention, the non-covalently bound complex is defined as one of the other particular embodiments, and the drug analog is:

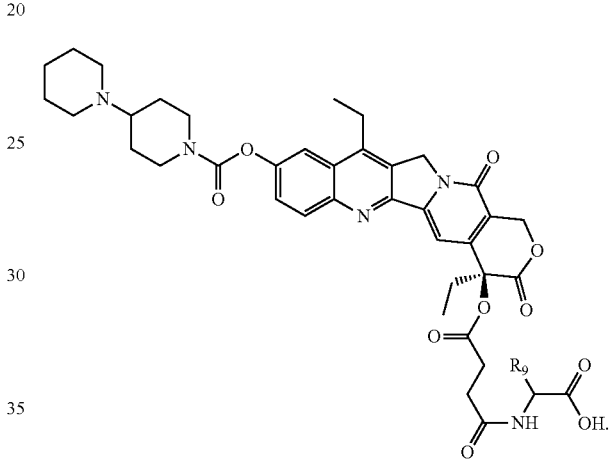

In another particular embodiment of the invention, the non-covalently bound complex is defined as one of the other particular embodiments, and the drug analog is:

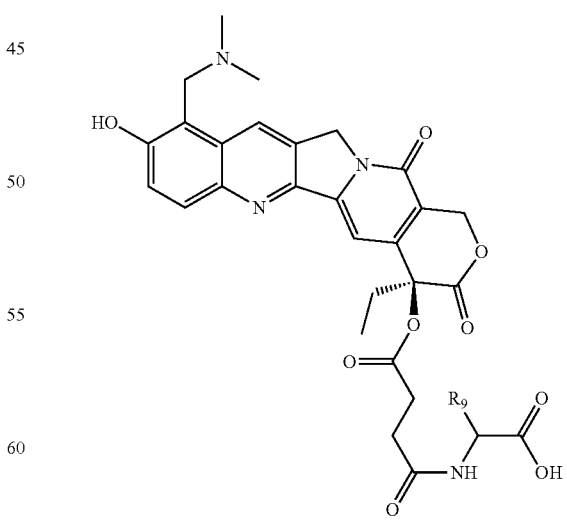

In another particular embodiment of the invention, the non-covalently bound complex is defined as one of the other particular embodiments, and the drug analog is:

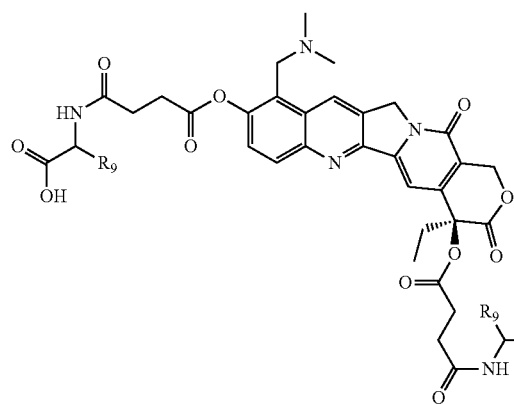

In another particular embodiment of the invention, the non-covalently bound complex is defined as one of the other particular embodiments, and the drug analog is:

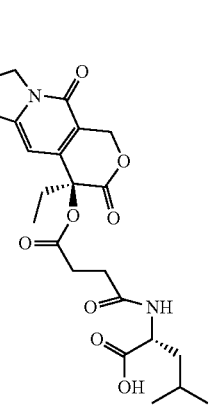

In another particular embodiment of the invention, the non-covalently bound complex is defined as one of the other particular embodiments, and the drug analog is:

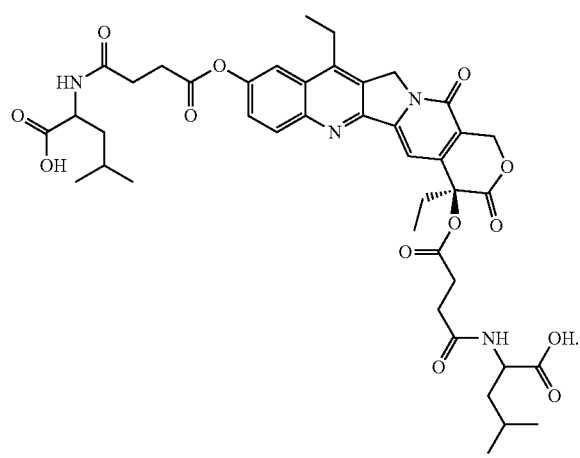 [SMILES: CCc1c2c(nc3ccc(OC(=O)CCC(=O)NC(CC(C)C)C(=O)O)cc13)-c1cc3c(c(=O)n1C2)COC(=O)[C@@]3(CC)OC(=O)CCC(=O)NC(CC(C)C)C(=O)O]

In a further particular embodiment of the invention, the non-covalently bound complex is defined as one of the other particular embodiments, and the drug analog is:

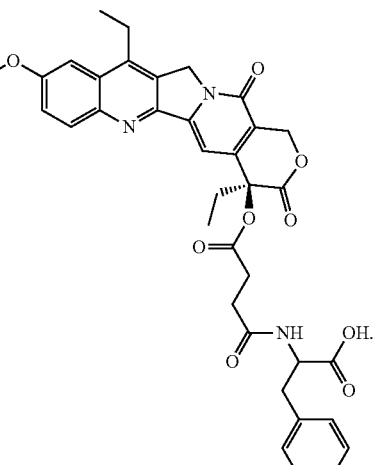

In another particular embodiment of the invention, the non-covalently bound complex is defined as one of the other particular embodiments, and the drug analog is:

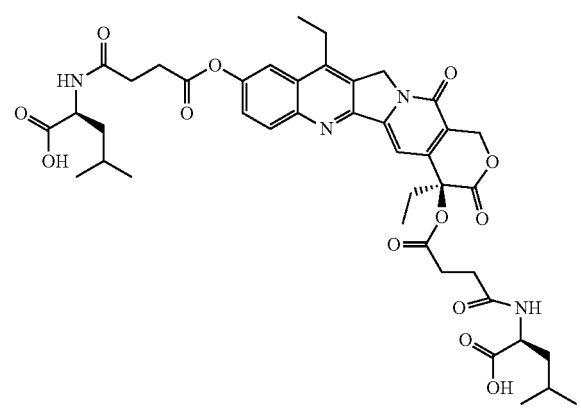 [SMILES: CCc1c2c(nc3ccc(OC(=O)CCC(=O)N[C@@H](CC(C)C)C(=O)O)cc13)-c1cc3c(c(=O)n1C2)COC(=O)[C@@]3(CC)OC(=O)CCC(=O)N[C@@H](CC(C)C)C(=O)O]

In a further particular embodiment of the invention, the non-covalently bound complex is defined as one of the other particular embodiments, and the drug analog is:

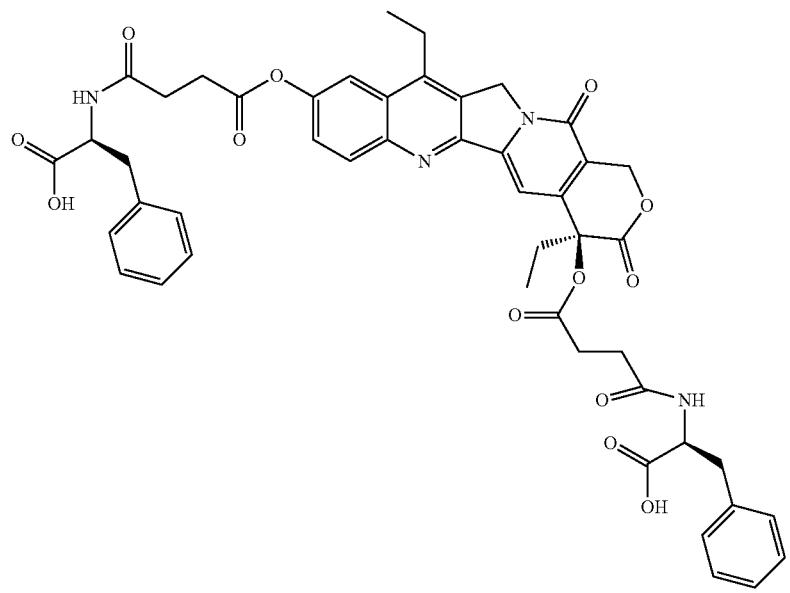 [SMILES: CCc1c2c(nc3ccc(OC(=O)CCC(=O)N[C@@H](Cc4ccccc4)C(=O)O)cc13)-c1cc3c(c(=O)n1C2)COC(=O)[C@@]3(CC)OC(=O)CCC(=O)N[C@@H](Cc1ccccc1)C(=O)O]
In a further particular embodiment of the invention, the non-covalently bound complex is defined as one of the other particular embodiments, and the drug analog is:
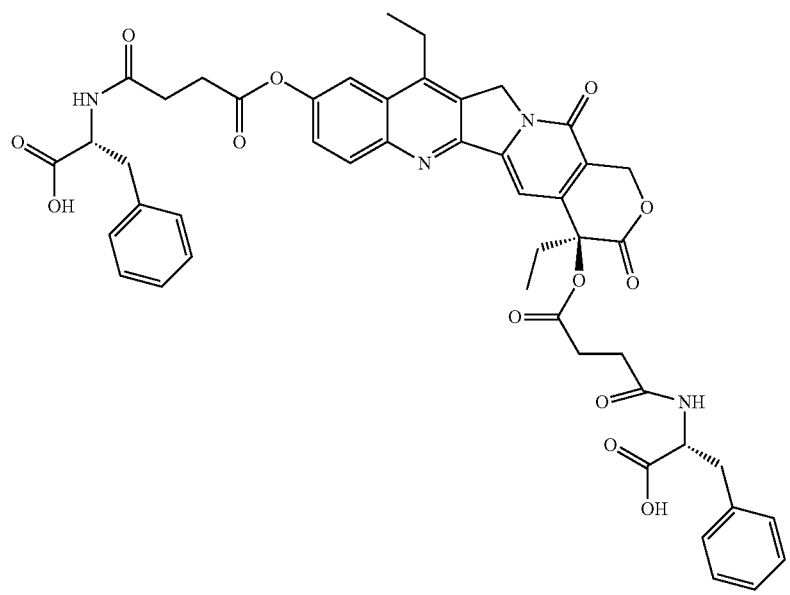 [SMILES: CCc1c2c(nc3ccc(OC(=O)CCC(=O)N[C@H](Cc4ccccc4)C(=O)O)cc13)-c1cc3c(c(=O)n1C2)COC(=O)[C@@]3(CC)OC(=O)CCC(=O)N[C@H](Cc1ccccc1)C(=O)O]
In another particular embodiment of the invention, the non-covalently bound complex is defined as one of the other particular embodiments, and the drug analog is:

21

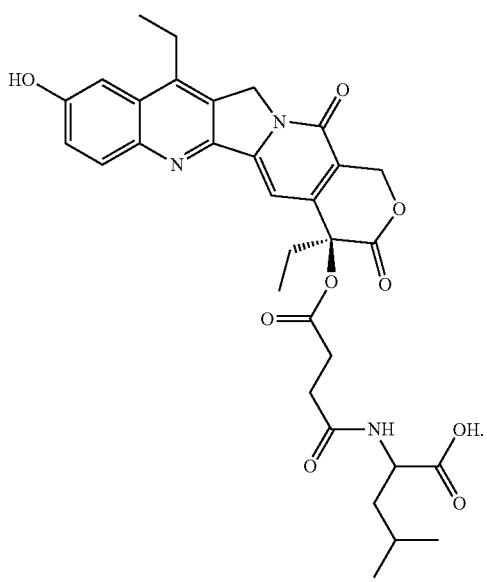 [SMILES: CCc1c2c(nc3ccc(O)cc13)-c1cc3c(c(=O)n1C2)COC(=O)[C@@]3(CC)OC(=O)CCC(=O)NC(CC(C)C)C(=O)O]

In a further particular embodiment of the invention, the non-covalently bound complex is defined as one of the other particular embodiments, and the drug analog is:

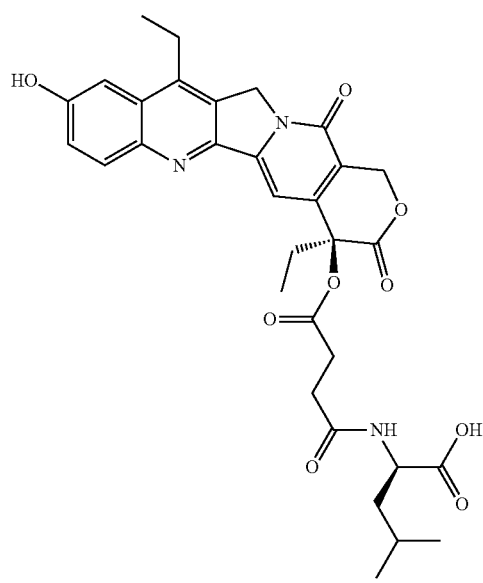 [SMILES: CCc1c2c(nc3ccc(O)cc13)-c1cc3c(c(=O)n1C2)COC(=O)[C@@]3(CC)OC(=O)CCC(=O)N[C@H](CC(C)C)C(=O)O]

In a further particular embodiment of the invention, the non-covalently bound complex is defined as one of the other particular embodiments, and the drug analog is:

22

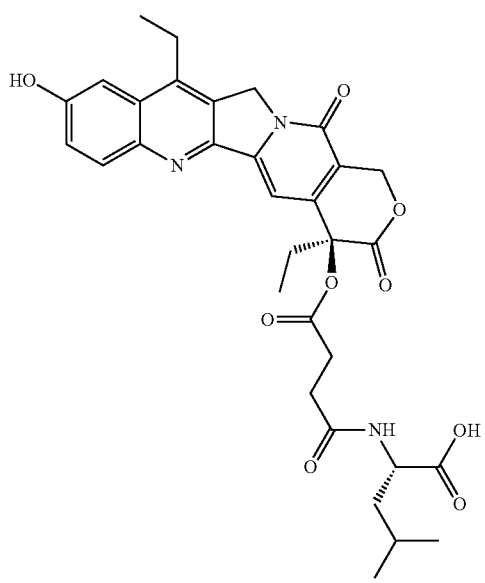 [SMILES: CCc1c2c(nc3ccc(O)cc13)-c1cc3c(c(=O)n1C2)COC(=O)[C@@]3(CC)OC(=O)CCC(=O)N[C@@H](CC(C)C)C(=O)O]

In a further particular embodiment of the invention, the non-covalently bound complex is defined as one of the other particular embodiments, and the drug analog is:

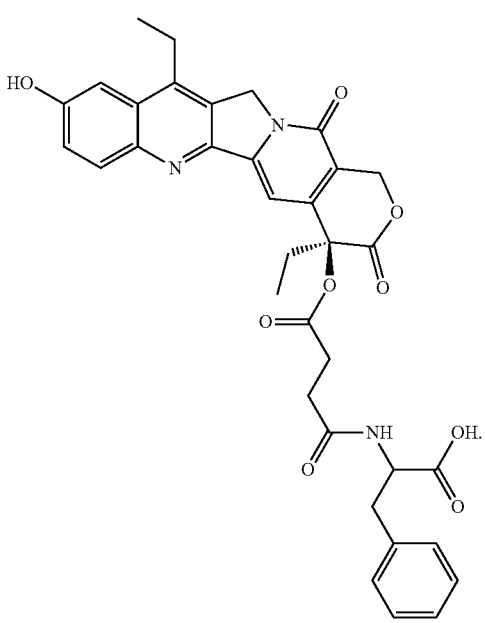 [SMILES: CCc1c2c(nc3ccc(O)cc13)-c1cc3c(c(=O)n1C2)COC(=O)[C@@]3(CC)OC(=O)CCC(=O)NC(Cc1ccccc1)C(=O)O]

In a further particular embodiment of the invention, the non-covalently bound complex is defined as one of the other particular embodiments, and the drug analog is:

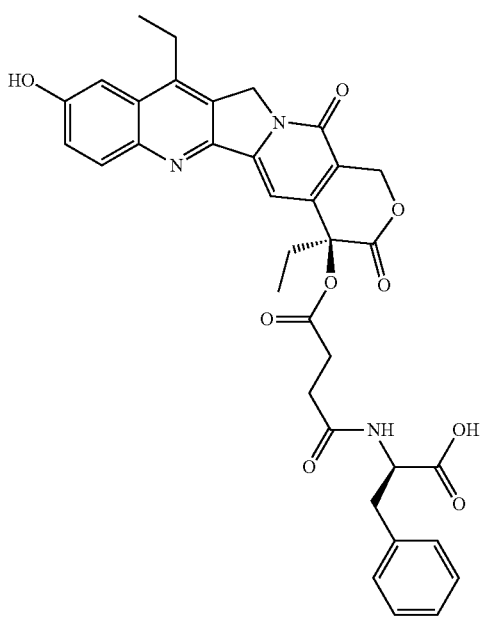 [SMILES: CCc1c2c(nc3ccc(O)cc13)-c1cc3c(c(=O)n1C2)COC(=O)[C@@]3(CC)OC(=O)CCC(=O)N[C@H](Cc1ccccc1)C(=O)O]

In a further particular embodiment of the invention, the non-covalently bound complex is defined as one of the other particular embodiments, and the drug analog is:

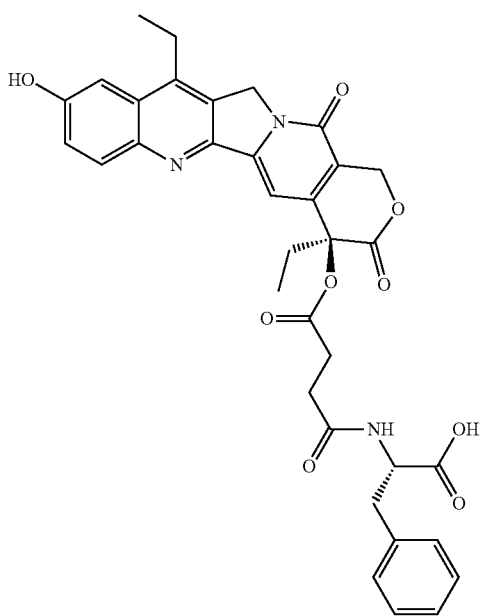 [SMILES: CCc1c2c(nc3ccc(O)cc13)-c1cc3c(c(=O)n1C2)COC(=O)[C@@]3(CC)OC(=O)CCC(=O)N[C@@H](Cc1ccccc1)C(=O)O]

In a further particular embodiment of the invention, a method is provided to treat cancer in a patient comprising administering a composition comprising a non-covalently bound complex as defined in one of the other particular embodiments to said patient in an effective amount to treat said cancer.

In another particular embodiment of the invention, the method of treating cancer is as defined in one of the other particular embodiments and the cancer is lung, breast, colon, prostate, melanoma, pancreas, stomach, liver, brain, kidney, uterus, cervix, ovaries, urinary tract, gastrointestinal or leukemia.

In a further particular embodiment of the invention, the method of treating cancer is as defined in one of the other particular embodiments and the cancer is solid tumor or blood borne tumor.

In another aspect of the invention, a method is provided to inhibit the enzyme topoisomerase I in an animal in need thereof, comprising administering to the animal an effective amount of a composition comprising one of the above particular embodiments of a non-covalently bound complex of a camptothecin analog and serum albumin. More particularly, the administration of the composition may be orally, parenterally, intramuscularly, transdermally, intravenously or by an airborne delivery system.

In a further aspect of the invention, a method is provided to treat cancer in a patient comprising administering a composition comprising one of the above particular embodiments of a non-covalently bound complex of a camptothecin analog and serum albumin to said patient in an effective amount to treat said cancer. More particularly, the cancer to be treated in this aspect of the invention may be a solid tumor or blood borne tumor, the cancer may be selected from lung cancer, breast cancer, colon cancer, prostate cancer, melanoma, pancreatic cancer, stomach cancer, liver cancer, brain cancer, kidney cancer, cancer of the uterus, cancer of the cervix, ovarian cancer, cancer of the urinary tract, gastrointestinal cancer and leukemia. More particularly, the administration of the composition may be orally, parenterally, intramuscularly, transdermally, intravenously or by an airborne delivery system.

Synthesis of camptothecin and camptothecin analogs, including Topotecan, Irinotecan, SN-38, 9-Aminocamptothecin, 9-Nitrocamptothecin, GI-147211, Exatecan and Karenitecin is well-documented in the literature and well-known to those of skill in the art of organic synthesis. Furthermore, camptothecin and several of the camptothecin analogs are commercially available. The following Schemes 1-4 are generic synthesis methods for making compounds of the present invention from camptothecin or camptothecin analogs. For conciseness, the Schemes are depicted for compounds of Formula I, wherein $R_7$ is a covalent bond. It is well within the ability of a skilled organic chemist to adapt these Schemes for synthesis of compounds of Formula I wherein $R_7$ is O or NH.

Scheme 1

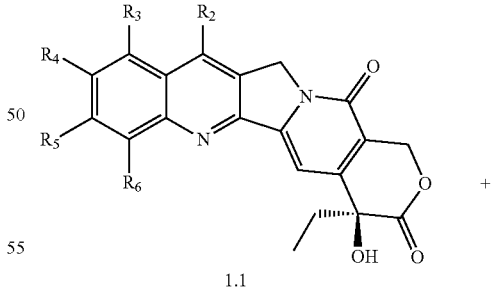

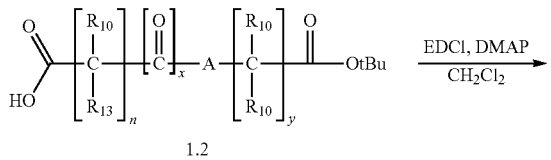

25
-continued
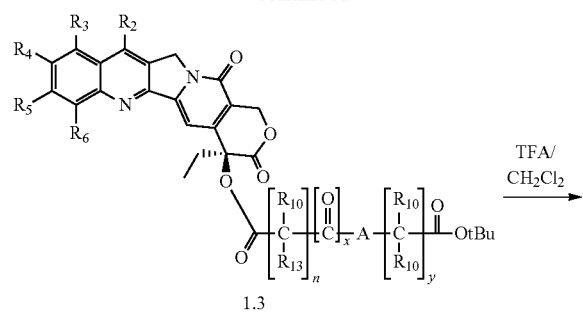
1.3
26
-continued
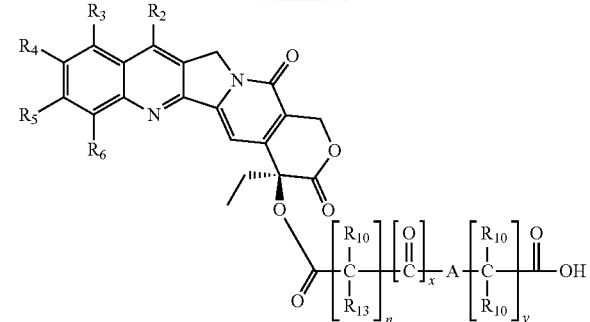
1.4
Scheme 2
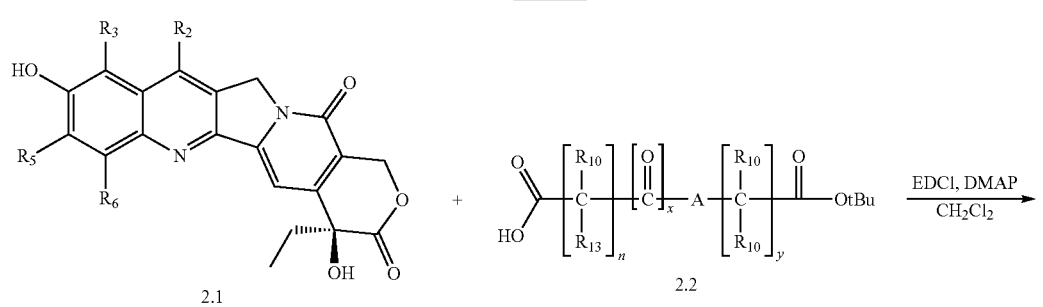
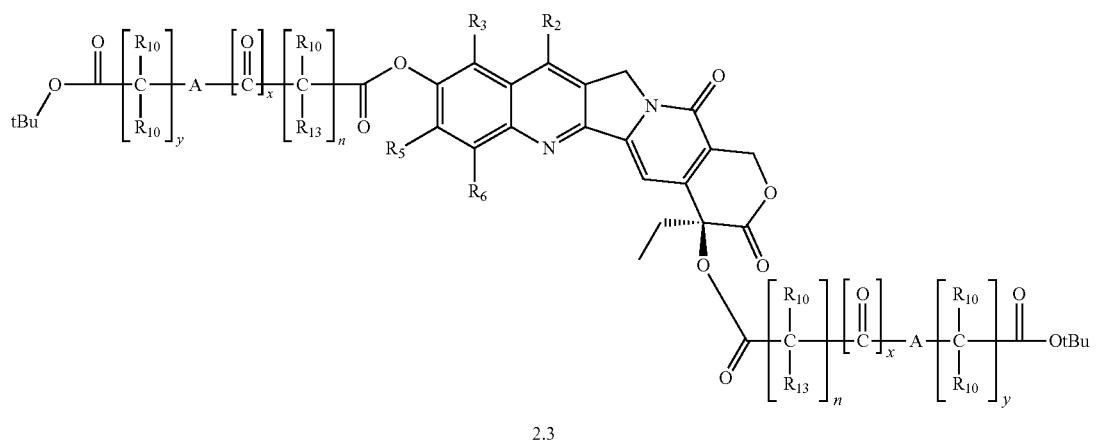
2.3
↓ TFA/CH₂Cl₂

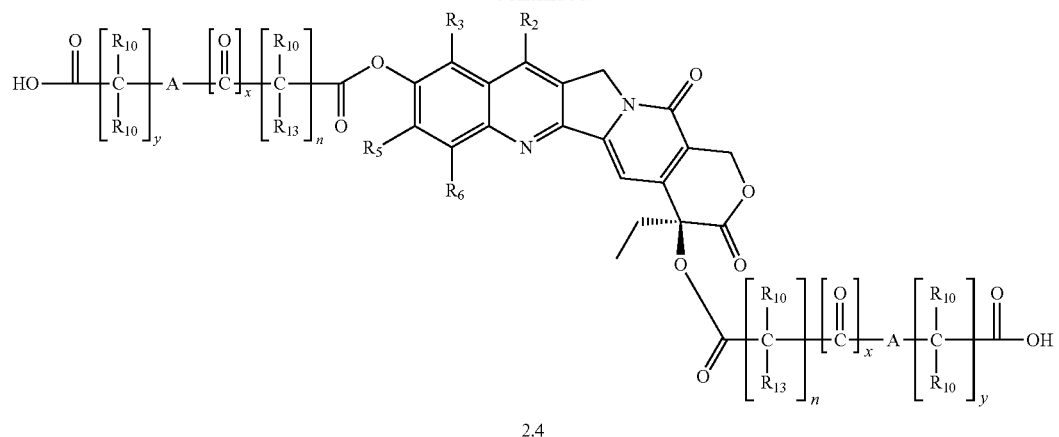
2.4
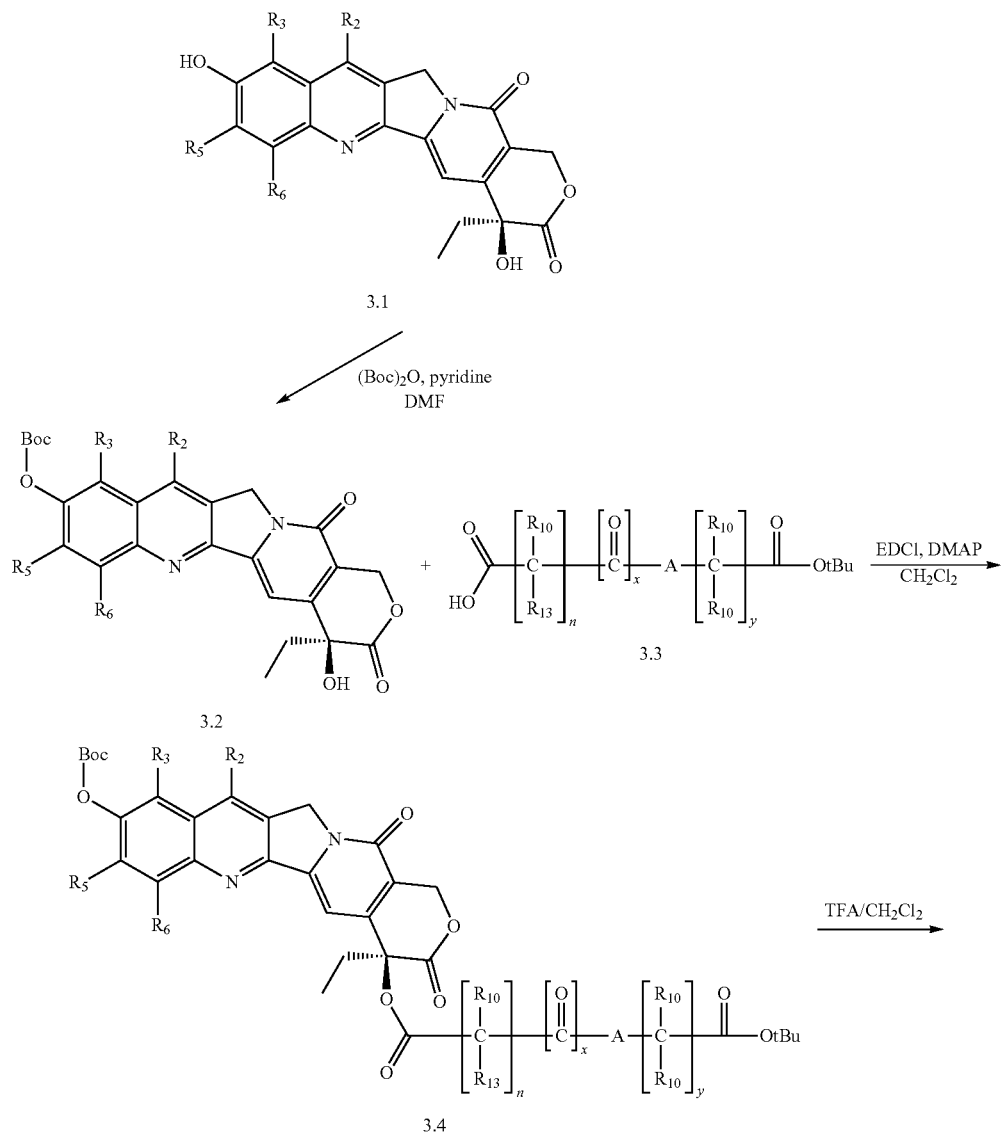

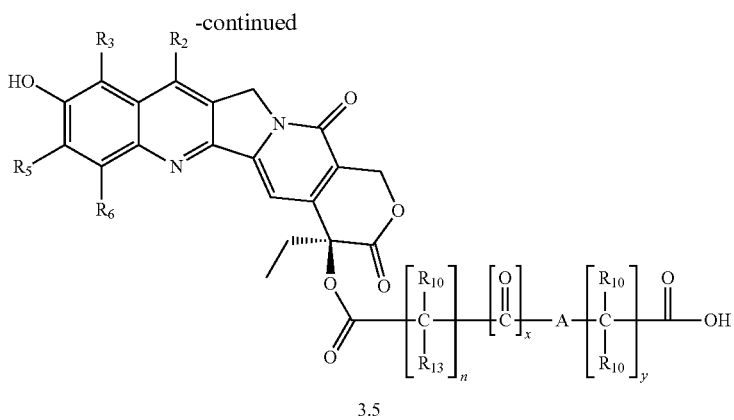

3.5

Scheme 4

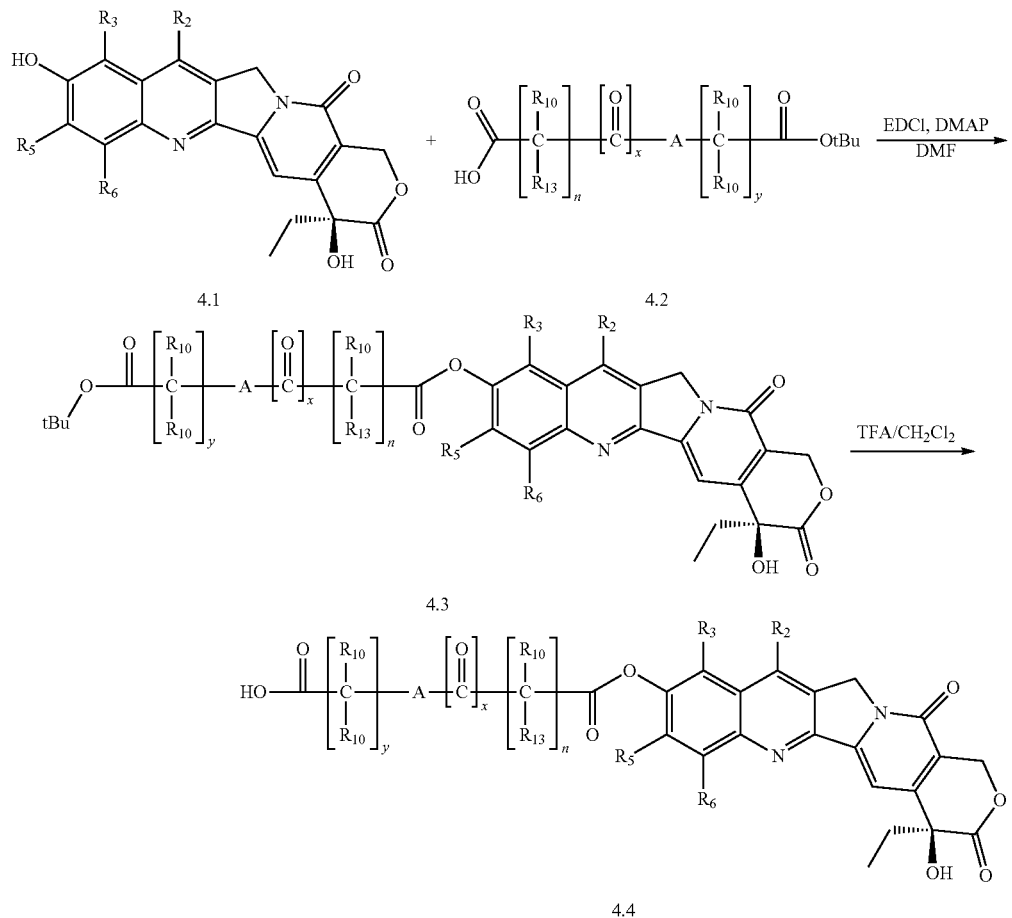

In a further aspect, the invention relates to pharmaceutical compositions containing a non-covalently bound complex of the invention together with pharmaceutically acceptable carriers and excipients. The pharmaceutical forms suitable to the oral or parenteral administration of the compounds of Formula I can be solid, preferably capsules, tablets and granules, or liquid, preferably injectable or infusion solutions.

The suitably formulated non-covalently bound complexes of camptothecin-analog and serum albumin of the invention can be used for the treatment of diseases responding to inhibition of Topoisomerase I, such as for example tumors, HIV infections and parasitic infections. In particular, the suitably formulated non-covalently bound complexes of camptothecin-analog and serum albumin of the invention can be used for the treatment of solid tumors and leukemias, including tumors of the lung, ovary, breast, stomach, liver, prostate, soft tissue sarcomas, head and neck, esophagus, pancreas, colon, rectum, glioblastoma, chronic and acute myelocytic leukemias. One of skill in the arts of pharmacology can prepare the non-covalently bound complexes of camptothecin-analog and serum albumin of the invention into suitable forms and dosages for desired routes of administration based on the abundant knowledge in the art of other camptothecin analogs that have been used pharmacologically and/or clinically. For instance, European Patent 2007386 BI by inventor Frederick H. Hausheer, entitled "CAMPTOTHECIN-ANALOG WITH A NOVEL, FLIPPED LACTONE-STABLE, E-RING AND METHODS FOR MAKING AND USING SAME", teaches the previous clinical and/or pharmacological use of more than a dozen camptothecin analogues, and is herein incorporated by reference.

EXAMPLES

Synthesis of FL-003

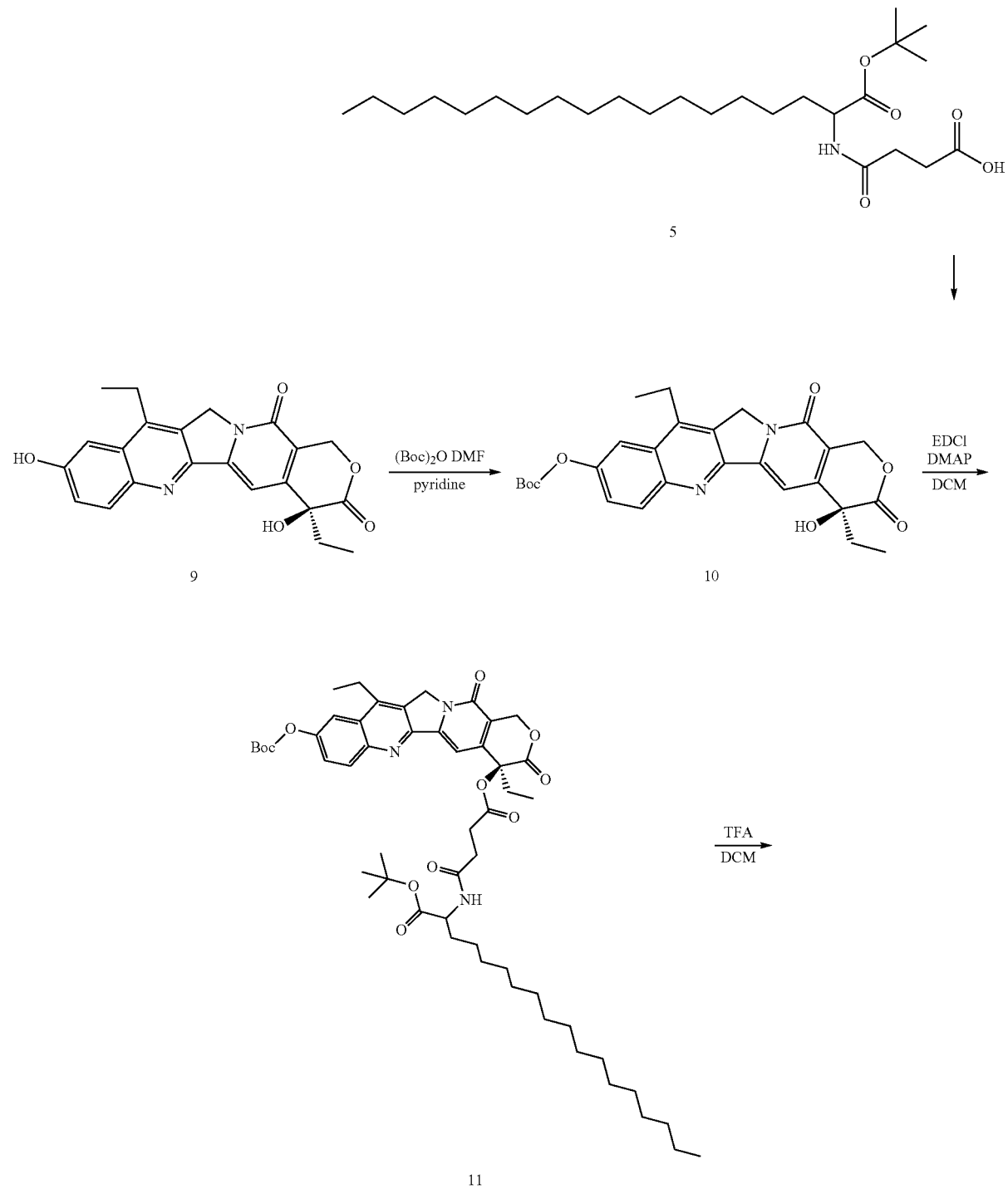

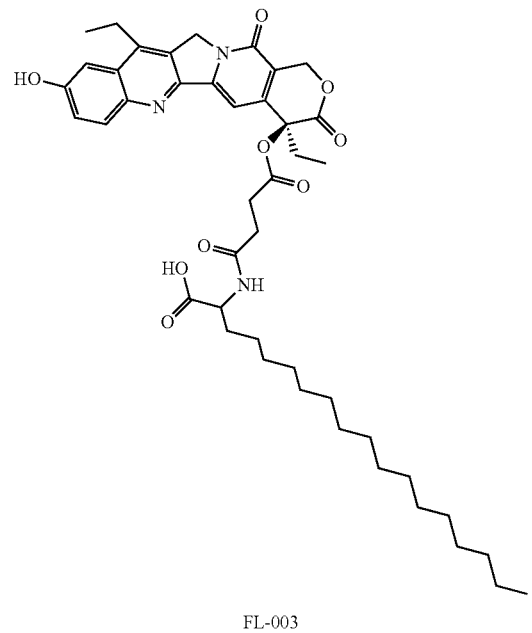 [SMILES: CCCCCCCCCCCCCCCCC(NC(=O)CCC(=O)O[C@]1(CC)C(=O)OCc2c1cc1n(c2=O)Cc2c-1nc1ccc(O)cc1c2CC)C(=O)O]

FL-003

1. Compound 9 (1.9 g) was dissolved into 15 ml pyridine and cooled down in an ice bath. (Boc)$_2$O (2.4 g) was added. The reaction was stirred at RT overnight. Volatiles were removed. The organic phase was separated and the aqueous phase was extracted with DCM, and washed with 0N HCl. The combined the organic phase was dried over Na$_2$SO$_4$ and concentrated to give compound 10 (2.0 g) as a white solid.
   1H NMR (300 MHz, CDCl$_3$) 8.4-8.5 (s, 1H), 8.2-8.3 (t, 1H), 7.9-8.0 (t, 1H), 7.8-7.9 (t, 1H), 7.6-7.7 (t, 1H), 7.3-7.4 (t, 1H), 3.1-3.2 (t, 2H), 1.4-1.5 (s, 9H), 0.8-0.9 (m, 3H).
2. Compound 5 (2.2 g) was dissolved into 30 ml DCM, and then EDCI (1.2 g), and DMAP (0.16 g) and compound 10 (1 g) were added. The reaction was maintained at 25° C. for 48 h, and TLC indicated reaction was completed. The organic phase was separated and the aqueous phase was extracted with DCM, and washed with NaHCO$_3$(aq). The combined the organic phase was dried over Na$_2$SO$_4$ and concentrated, and the residue was purified by flash chromatography using 2% MeOH/CHCl$_3$ to give compound 11 (0.6 g) as a white solid.
   1H NMR (300 MHz, CDCl$_3$) 8.4-8.5 (s, 1H), 8.2-8.3 (D, 1H), 7.9-8.0 (s, 1H), 7.6-7.7 (d, 1H), 7.2-7.3 (t, 1H), 6.0-6.2 (bs, 1H), 5.6-5.7 (d, 1H), 5.3-5.5 (d, 1H), 5.2-5.3 (s, 2H), 4.4-4.6 (m, 1H), 3.1-3.2 (t, 2H), 2.8-2.9 (t, 2H), 2.5-2.6 (t, 2H), 2.1-2.4 (m, 2H), 1.4-1.5 (s, 9H), 1.3-1.4 (s, 9H), 1.2-1.3 (m, 33H), 0.9-1.0 (t, 2H), 0.8-0.9 (m, 3H), 0.7-0.8 (m, 3H).
3. Compound 11 (0.2 g) was dissolved into 30 ml DCM, and TFA (2 ml) were added. The reaction was maintained at 25° C. for 12 h, and TLC indicated reaction was completed. The reaction was concentrated, and the residue was purified by flash chromatography using 5% MeOH/CHCl$_3$ to give FL-003 (0.11 g) as a solid.
   1H NMR (300 MHz, DMSO-d6) 10.2-10.6 (bs, 1H), 8.0-8.3 (m, 2H), 7.4-7.5 (t, 2H), 7.0-7.2 (d, 1H), 5.5-5.6 (s, 2H), 5.3-5.4 (s, 2H), 4.2-4.4 (m, 1H), 3.1-3.2 (t, 2H), 2.6-2.8 (m, 2H), 2.4-2.5 (t, 1H), 2.1-2.2 (m, 2H), 1.5-1.7 (m, 2H), 0.8-1.4 (m, 41H).
   LCMS: 774.4 (M+1)$^+$ Synthesis of FL-006

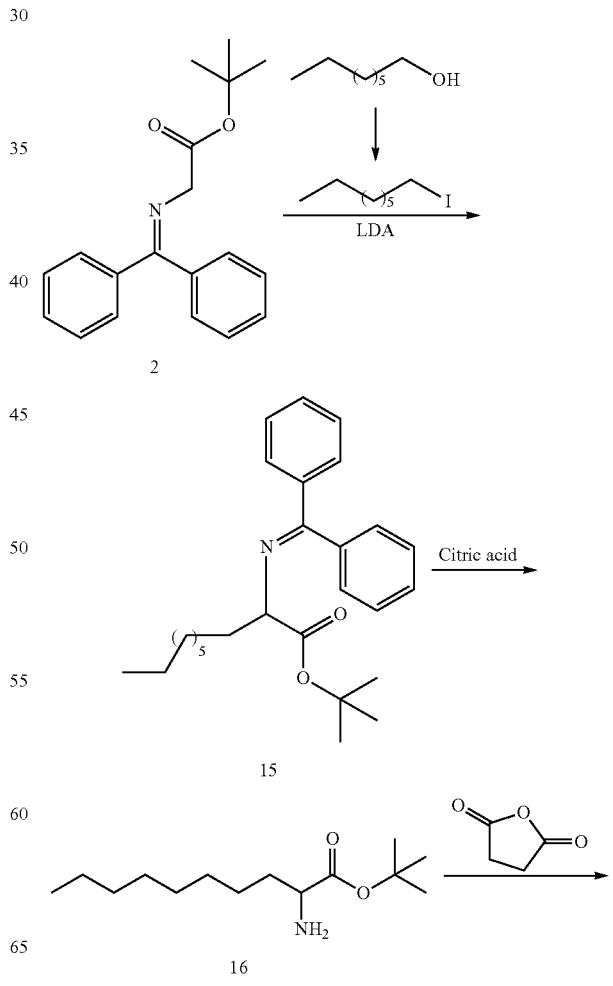

-continued

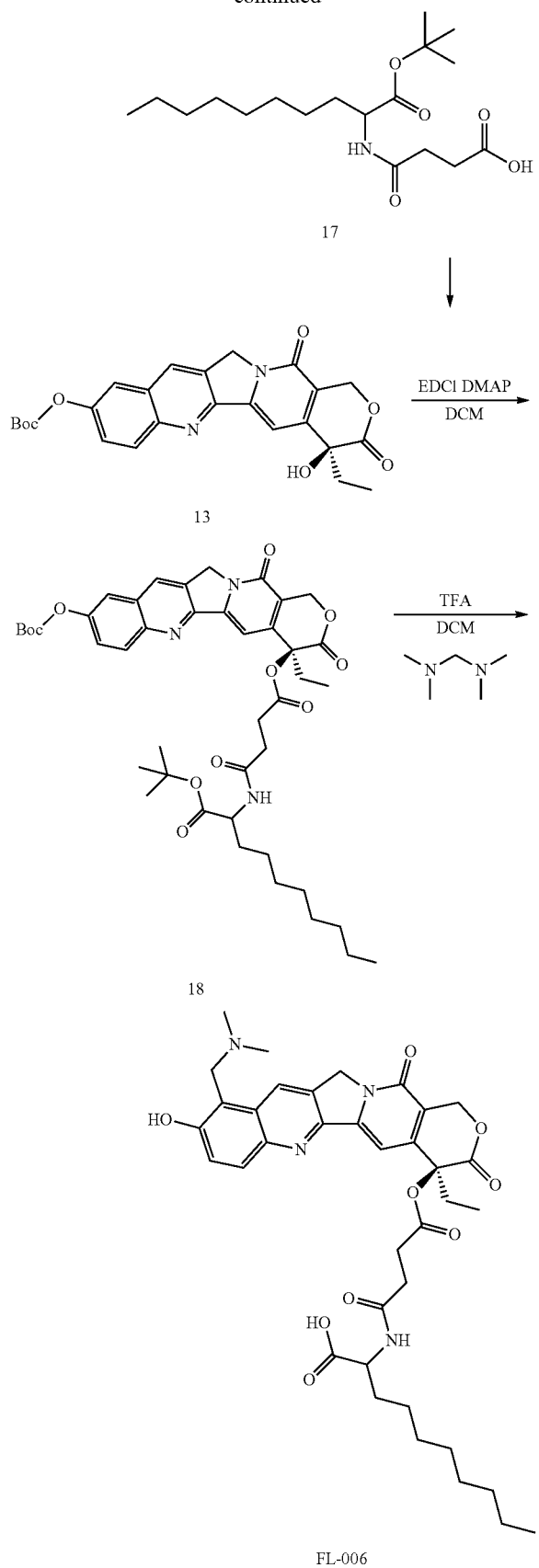

1. Compound 2 (32 g) in THF (150 m) was added to LDA (2.2 eq) and kept at −78° C. in dry THF (150 ml) under argon for 30 minutes. Then 1-iodoheptane (33 g) was added to the stirred mixture. After 2 h, the mixture was allowed to come slowly to room temperature and stirred overnight. The reaction was quenched by addition of water (100 ml) to the mixture at 0° C. The mixture was then extracted with $CH_2Cl_2$ (200 ml*3). The product was purified by column on silica gel and recrystallization by 5% EA/PE to give pure compound 15 (18 g) as a white solid.
   1HNMR (300 MHz, $CDCl_3$) 7.6-7.7 (m, 2H), 7.4-7.5 (m, 3H), 7.3-7.4 (m, 3H), 7.1-7.2 (m, 2H), 3.8- 4.0 (m, 1H), 1.4-1.5 (s, 9H), 1.2-1.4 (m, 30H), 0.8-1.0 (m, 3H).

2. To a solution of compound 15 (25 g) in 200 ml of THF at RT was added 210 ml of 10% aq. Citric acid. The mixture was stirred overnight. The reaction was quenched by addition of water (200 ml) to the mixture at 0° C. and adjust the pH value about 7 with $NaHCO_3$. The resultant mixture was extracted with $CH_2Cl_2$ (150 ml*3). Organic phase was washed with saturated solution of sodium chloride and dried over $Na_2SO_4$. The solvent was removed on vacuum to give a crude product, which was purified by column on silica gel and recrystallized by 50% EA/PE to give compound 16 (15 g) as a white solid.
   1H NMR (300 MHz, $CDCl_3$) 3.3-3.4 (1H), 1.4-1.5 (s, 9H), 1.2-1.4 (m, 30H), 0.8-1.0 (3H).

3. Compound 16 (2.8 g) was dissolved into 15 ml pyridine and cooled down in an ice bath. Dihydrofuran-2,5-dione (1.5 g) was added. The reaction was stirred at RT overnight. Volatiles were removed. The organic phase was separated and the aqueous phase was extracted with DCM, and washed with 2N HCl. The combined the organic phase was dried over $Na_2SO_4$ and concentrated to give compound 17 (2.7 g) as a white solid.
   1H NMR (300 MHz, $CDCl_3$) 6.2-6.3 (bs, 1H), 4.4-4.5 (m, 1H), 2.7-2.8 (t, 2H), 2.5-2.6 (t, 2H), 1.8-1.9 (m, 1H), 1.4-1.5 (s, 9H), 1.2-1.4 (m, 29H), 0.8-0.9 (t, 3H).

4. Compound 17 (2.7 g) was dissolved into 35 ml DCM, and then EDCI (1.4 g), and DMAP (0.13 g) and compound 13 (1.1 g) were added. The reaction was maintained at 25° C. for 48 h, and TLC indicated reaction was completed. The organic phase was separated and the aqueous phase was extracted with DCM, and washed with $NaHCO_3$(aq). The combined the organic phase was dried over $Na_2SO_4$ and concentrated, and the residue was purified by flash chromatography using 2% $MeOH/CHCl_3$ to give compound 18 (1.25 g) as a white solid.
   1H NMR (300 MHz, $CDCl_3$) 8.4-8.5 (s, 1H), 8.2-8.3 (d, 1H), 7.9-8.0 (s, 1H), 7.6-7.7 (d, 1H), 7.2-7.3 (t, 1H), 6.0-6.2 (bs, 1H), 5.6-5.7 (d, 1H), 5.3-5.5 (d, 1H), 5.2-5.3 (s, 2H), 4.4-4.6 (m, 1H), 3.1-3.2 (t, 2H), 2.8-2.9 (t, 2H), 2.5-2.6 (t, 2H), 2.1-2.4 (m, 2H), 1.4-1.5 (s, 9H), 1.3-1.4 (s, 9H), 1.2-1.3 (m, 14H), 0.9-1.0 (t, 2H), 0.8-0.9 (m, 3H), 0.7-0.8 (m, 3H).

5. Compound 18 (0.4 g) was dissolved into 10 ml DCM, and TFA (1.6 ml) was added. The reaction was maintained at 25° C. for 12 h, and TLC indicated reaction was completed. Bis-(dimethylamino)-methane (0.6 ml) was added slowly. The reaction was maintained at 25° C. for 12 h and concentrated, and the residue was purified by reverse phase preparative HPLC using a gradient of water and MeOH with 0.1% trifluoroacetic acid to afford 110 mg of FL-006.
   1H NMR (300 MHz, DMSO-d6) 11.5-11.6 (bs, 1H), 9.7-9.9 (bs, 1H), 8.9-9.0 (s, 1H), 8.1-8.3 (m, 2H), 7.6-7.7 (d, 1H), 7.0-7.1 (d, 1H), 5.5-5.6 (s, 2H), 5.3-5.4 (s, 2H), 4.7-4.9 (s, 2H), 4.2-4.4 (m, 1H)

2.8-2.9 (s, 6H), 2.6-2.8 (m, 2H), 2.1-2.2 (m, 2H), 1.5-1.7 (m, 2H), 0.8-1.4 (m, 20H).

LCMS: 691.4 (M+1)$^+$

Synthesis of FL-007

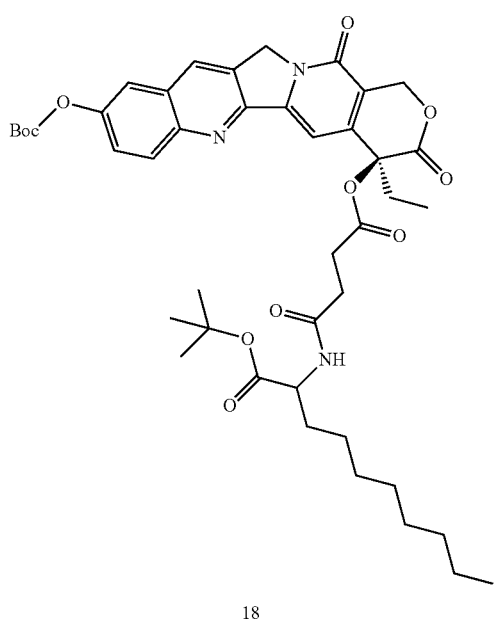

18

TFA / DCM →

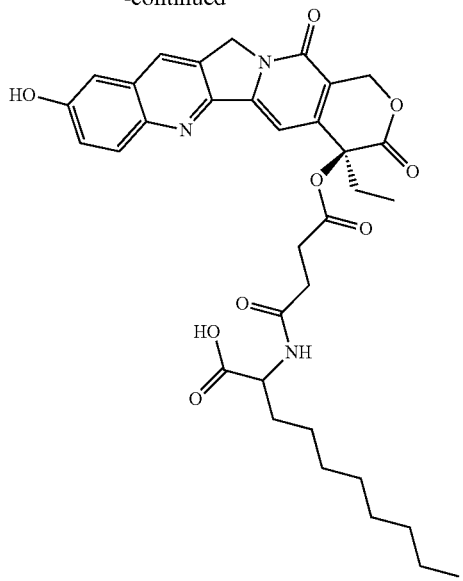

FL-007

1. Compound 18 (110 mg) was dissolved into 10 ml DCM, and TFA (0.9 ml) was added. The reaction was maintained at 25° C. for 12 h, and TLC indicated reaction was completed. The mixture was concentrated, and the residue was purified by flash chromatography using 5% MeOH/CHCl$_3$ to give FL-007 (50 mg) as a solid.

1H NMR (300 MHz, DMSO-d6) 10.2-10.3 (bs, 1H), 8.3-8.4 (s, 1H), 8.0-8.3 (m, 2H), 7.3-7.5 (m, 2H), 7.0-7.1 (d, 1H), 5.5-5.6 (s, 2H), 5.3-5.4 (s, 2H), 4.2-4.4 (m, 1H), 2.7-2.8 (m, 2H), 2.1-2.2 (m, 2H), 1.5-1.7 (m, 2H), 0.8-1.4 (m, 25H).

LCMS: 634.3 (M+1)$^+$

Synthesis of FL-036

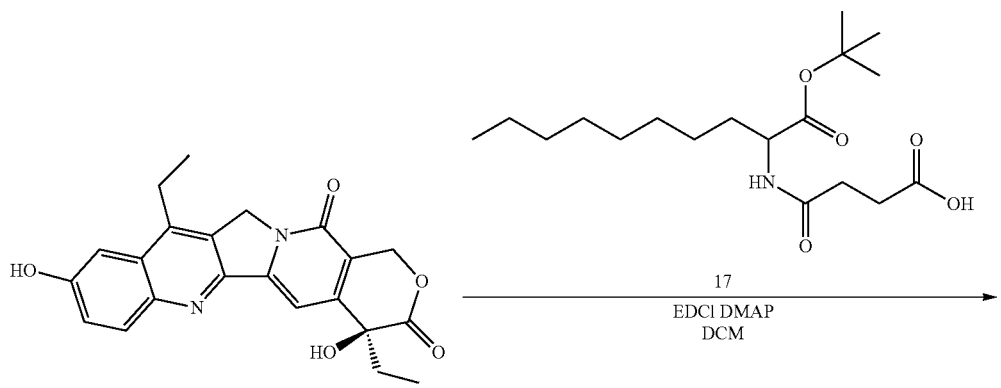

9      17
EDCl DMAP
DCM →

-continued

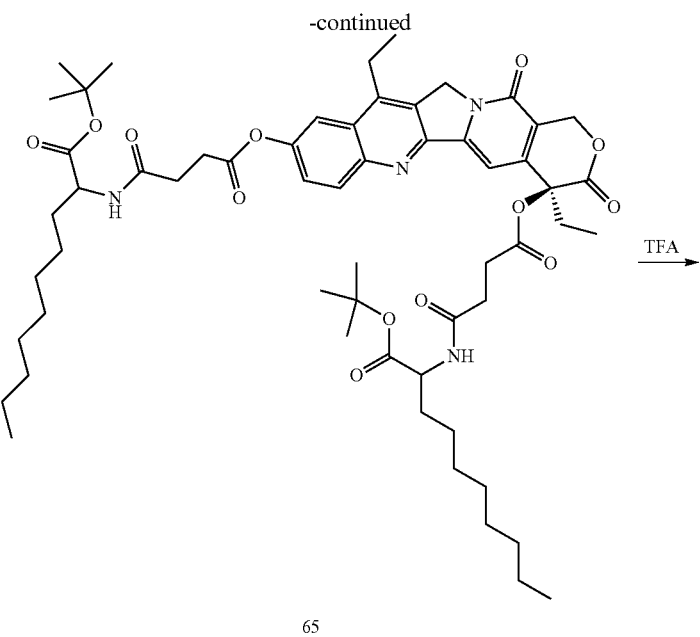

65

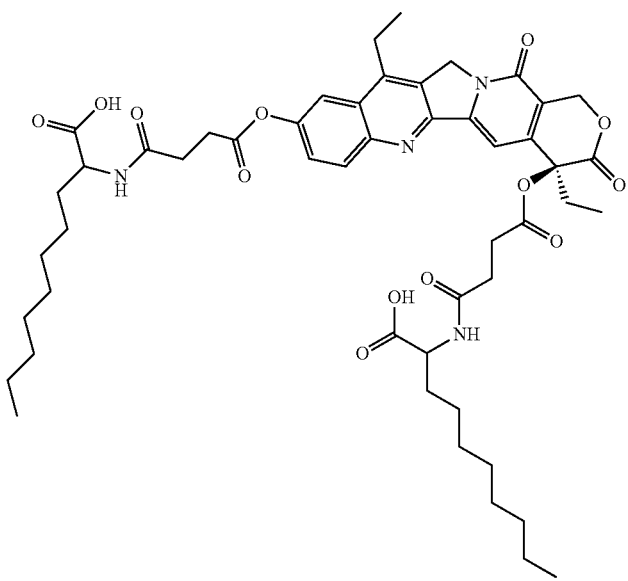

FL-036

1. Compound 17 (0.7 g) was dissolved into 10 ml DCM, and EDCI (0.488 g), DMAP (63 mg) and compound 9 (0.2 g) were added. The reaction was maintained at 25° C. for 48 h, and TLC indicated reaction was completed. The organic phase was separated and the aqueous phase was extracted with DCM, and washed with NaHCO₃ (aq). The combined organic phase was dried over Na₂SO₄ and concentrated and the residue was purified by flash chromatography using 2% MeOH/CHCl₃ to give compound 65 (150 mg).

1H NMR (300 MHz, CDCl₃) 8.3-8.4 (t, 1H), 7.8-7.9 (s, 1H), 7.6-7.7 (d, 1H), 7.3-7.4 (d, 1H), 6.1-6.2 (t, 2H), 6.0-6.2 (bs, 1H), 5.6-5.7 (d, 1H), 5.3-5.5 (d, 1H), 5.2-5.3 (s, 2H), 4.4-4.6 (m, 2H), 3.1-3.2 (t, 2H), 3.0-3.1 (t, 2H), 2.8-2.9 (t, 2H), 2.5-2.6 (t, 2H), 2.1-2.4 (m, 2H), 1.4-1.5 (s, 18H), 0.8-1.5 (m, 38H)

2. Compound 65 (150 mg) was dissolved into 10 ml DCM, and TFA (1.5 ml) were added. The reaction was maintained at 25° C. for 12 h, and TLC indicated reaction was completed. The solvent was removed and the residue was purified by flash chromatography using 5% MeOH/CHCl₃ to give FL-036 (120 mg).

1H NMR (300 MHz, DMSO-d6) 8.3-8.4 (t, 1H), 7.8-7.9 (s, 1H), 7.6-7.7 (d, 1H), 7.3-7.4 (d, 1H), 6.1-6.2 (t, 2H), 6.0-6.2 (bs, 1H), 5.3-5.5 (s, 2H), 5.2-5.3 (s, 2H), 4.4-4.6 (m, 2H), 3.1-3.2 (t, 2H), 3.0-3.1 (t, 2H), 2.8-2.9 (t, 2H), 2.5-2.6 (t, 2H), 2.1-2.4 (m, 2H), 0.8-1.5 (m, 38H)

LCMS: 931.7 (M+1)⁺

Synthesis of FL-037
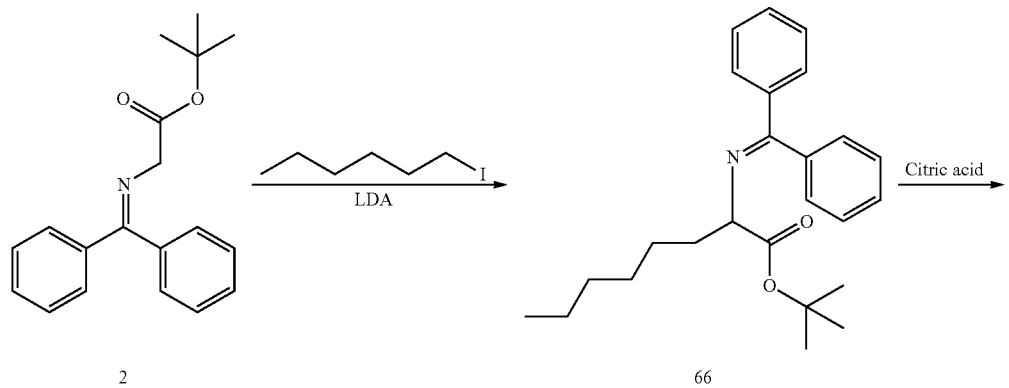
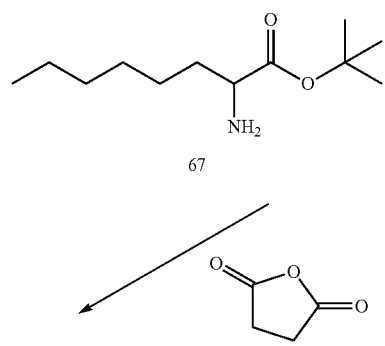
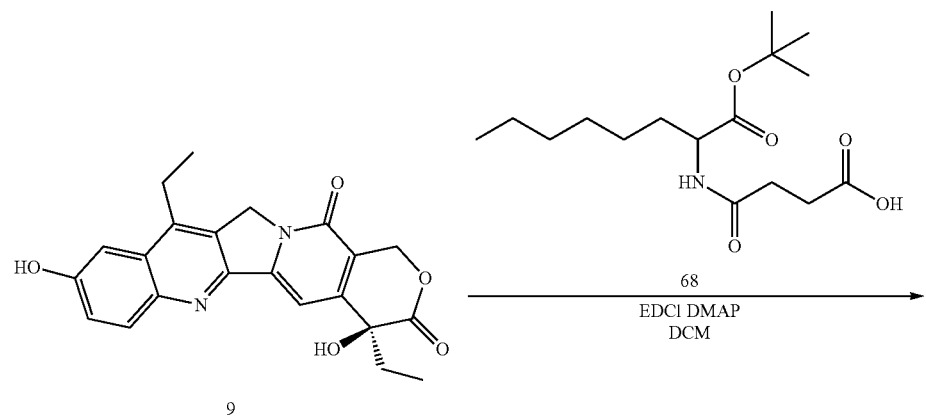

-continued

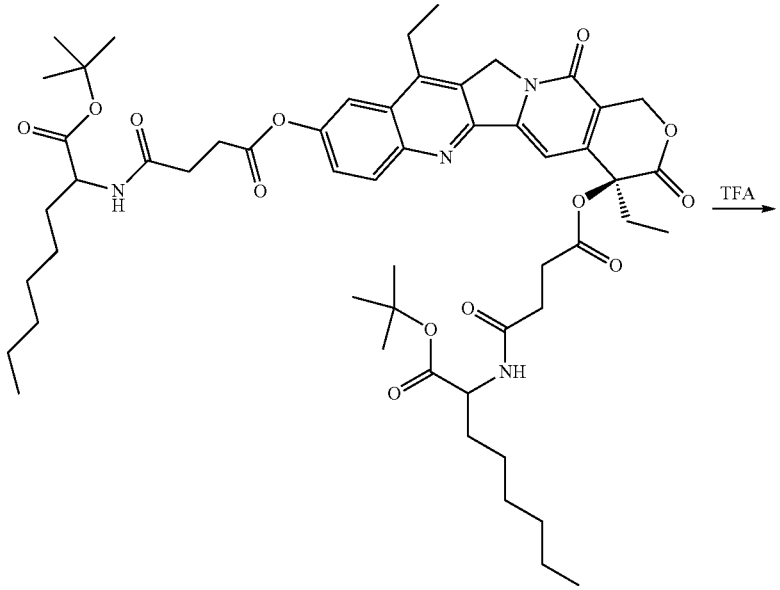

69

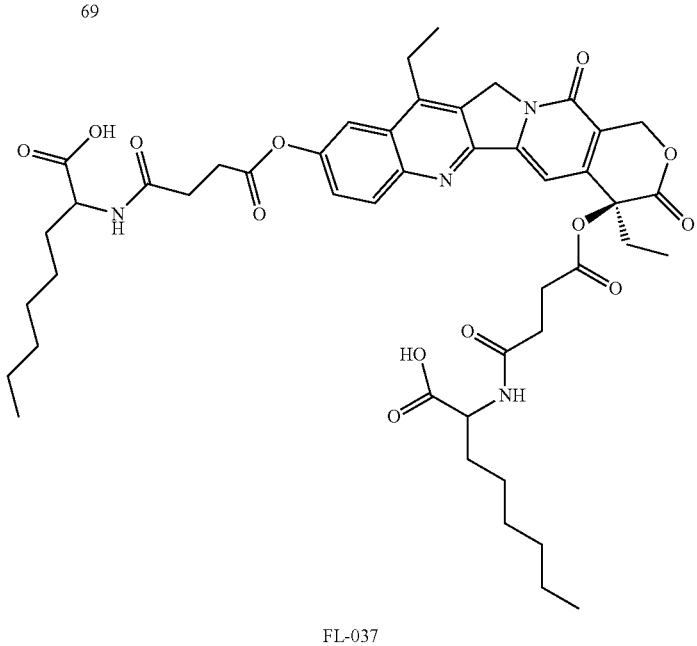

FL-037

1. Compound 2 (28.5 g) in THF (150 ml) was added to LDA (2.2 eq) and kept at −78° C. in dry THF (150 ml) under nitrogen. After 30 min, 1-iodohexane (14.1 g) was added to the reaction mixture. After 2 h, the mixture was allowed to warm slowly to room temperature and stirred overnight. The reaction was quenched by addition of water (100 ml) to the mixture at 0° C. The mixture was then extracted with $CH_2Cl_2$ (200 ml*3), the product was purified by silica gel column and recrystallized by 5% EA/PE to give compound 66 (16 g) as a white solid.

1H NMR (300 MHz, $CDCl_3$) 7.6-7.7 (m, 2H), 7.4-7.5 (m, 3H), 7.3-7.4 (m, 3H), 7.1-7.2 (m, 2H), 3.8-4.0 (m, 1H), 1.4-1.5 (s, 9H), 1.2-1.4 (m, 10H), 0.8-1.0 (m, 3H).

2. To a solution of compound 66 (16 g) in 100 ml of THF at RT was added 110 ml of 10% aq. Citric acid. The mixture was stirred overnight. The reaction was quenched by addition of water (200 ml) to the mixture at 0° C. The pH value is adjusted to about 7 using $NaHCO_3$. The resulting mixture was extracted with $CH_2Cl_2$ (150 ml*3). The organic phase was washed with saturated solution of sodium chloride and dried over $Na_2SO_4$. The solvent was removed on vacuum to give a crude product, which was purity by the silica gel column and recrystallized by 50% EA/PE to give compound 67 (8.5 g) as a white solid.

1H NMR (300 MHz, $CDCl_3$): 3.3-3.4 (1H), 1.4-1.5 (s, 9H), 1.2-1.4 (m, 6H), 0.8-1.0 (3H).

3. Compound 67 (2.66 g) was dissolved into 15 ml pyridine and cooled down in an ice bath. Dihydrofuran-2,5-dione (1.75 g) was added. The reaction was stirred at RT overnight. Volatiles were removed. The organic phase was separated and the aqueous phase was extracted with DCM, and washed with 2N HCl. The combined the organic phase was dried over $Na_2SO_4$ and concentrated to give compound 68 (2.35 g) as a white solid.

1H NMR (300 MHz, $CDCl_3$): 6.2-6.3 (bs, 1H), 4.4-4.5 (m, 1H), 2.7-2.8 (t, 2H), 2.5-2.6 (t, 2H), 1.8-1.9 (m, 1H), 1.4-1.5 (s, 9H), 1.2-1.4 (m, 10H), 0.8-0.9 (t, 3H).

4. Compound 68 (0.641 g) was dissolved into 10 ml DCM, and EDCI (0.5 g), DMAP (60 mg) and compound 9 (0.2 g) were added. The reaction was maintained at 25° C. for 12 h, and TLC indicated reaction was completed. The organic phase was separated and the aqueous phase was extracted with DCM, and washed with $NaHCO_3$(aq). The combined organic phase was dried over $Na_2SO_4$ and concentrated, and the residue was purified by flash chromatography using 2% $MeOH/CHCl_3$ to give compound 69 (210 mg).

1H NMR (300 MHz, $CDCl_3$): 8.3-8.4 (t, 1H), 7.8-7.9 (s, 1H), 7.5-7.6 (d, 1H), 7.2-7.3 (d, 1H), 6.0-6.2 (bs, 2H), 5.6-5.7 (d, 1H), 5.3-5.4 (d, 1H), 5.2-5.3 (s, 2H), 4.4-4.6 (m, 2H), 3.1-3.2 (t, 2H), 2.9-3.0 (t, 2H), 2.7-2.8 (t, 2H), 2.6-2.7 (t, 2H), 2.4-2.5 (m, 2H), 2.0-2.2 (m, 2H), 1.1-1.5 (m, 44H), 0.8-0.9 (t, 3H), 0.7-0.8 (t, 3H), 0.6-0.7 (m, 2H).

5. Compound 69 (210 mg) was dissolved into 10 ml DCM, and TFA (1.9 ml) were added. The reaction was maintained at 25° C. for 12 h, and TLC indicated reaction was completed. The solvent was removed and the residue was purified by flash chromatography using 5% $MeOH/CHCl_3$ to give FL-037 (180 mg).

1H NMR (300 MHz, DMSO-d6): 8.3-8.4 (bs, 2H), 8.2-8.3 (d, 1H), 7.8-7.9 (s, 1H), 7.5-7.6 (d, 1H), 7.2-7.3 (d, 1H), 5.5-5.6 (s, 2H), 5.2-5.3 (s, 2H), 4.2-4.3 (m, 2H), 3.2-3.3 (t, 2H), 2.9-3.0 (t, 2H), 2.7-2.8 (t, 2H), 2.5-2.6 (t, 2H), 2.4-2.5 (m, 2H), 2.0-2.2 (m, 2H), 1.1-1.5 (m, 26H), 0.8-0.9 (t, 3H), 0.7-0.8 (t, 3H), 0.6-0.7 (m, 2H).

LCMS: 876.6 $(M+1)^+$

Synthesis of FL-038

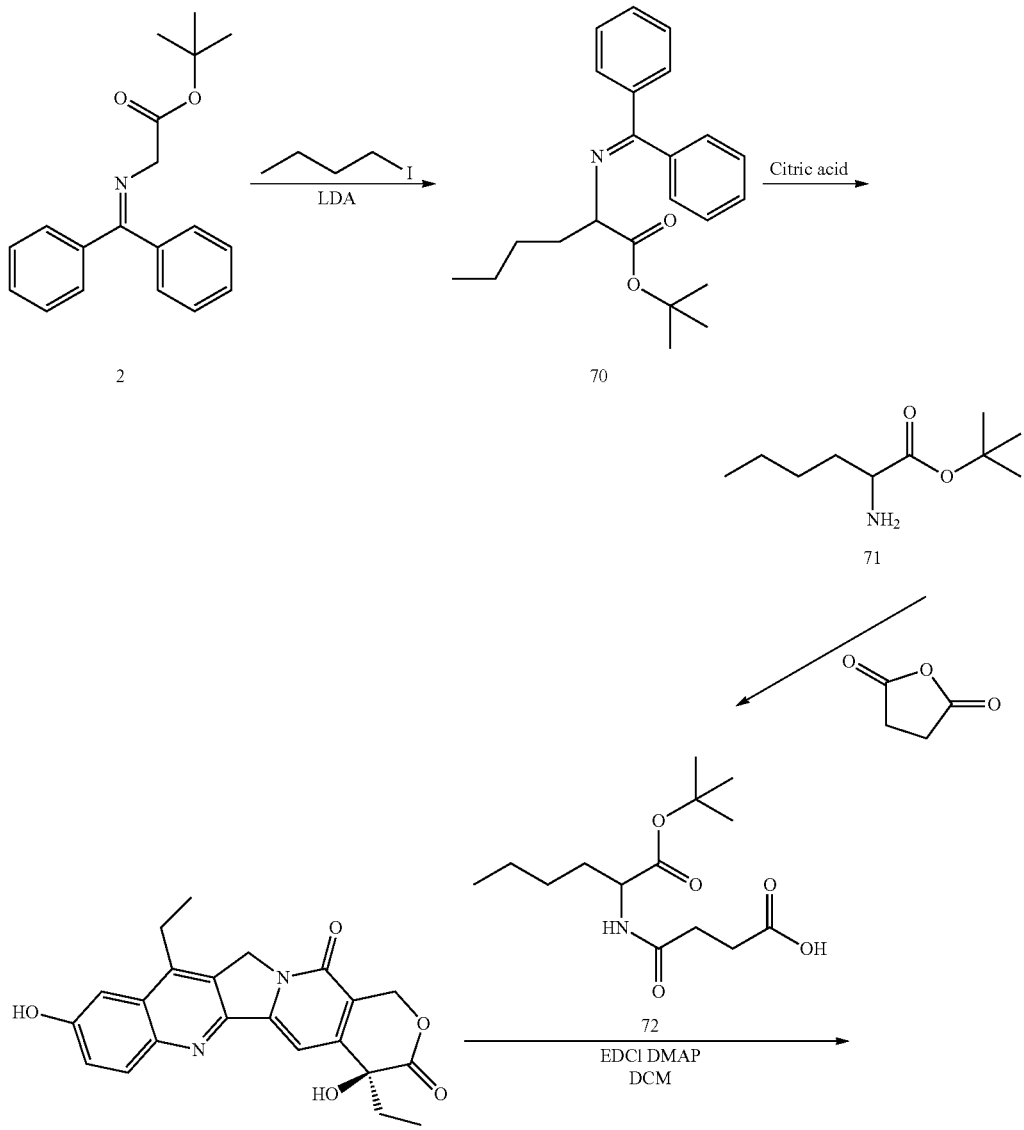

-continued

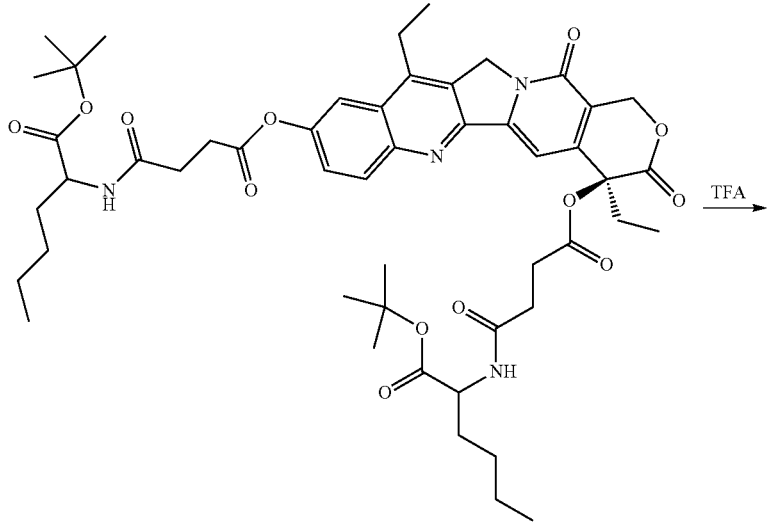

73

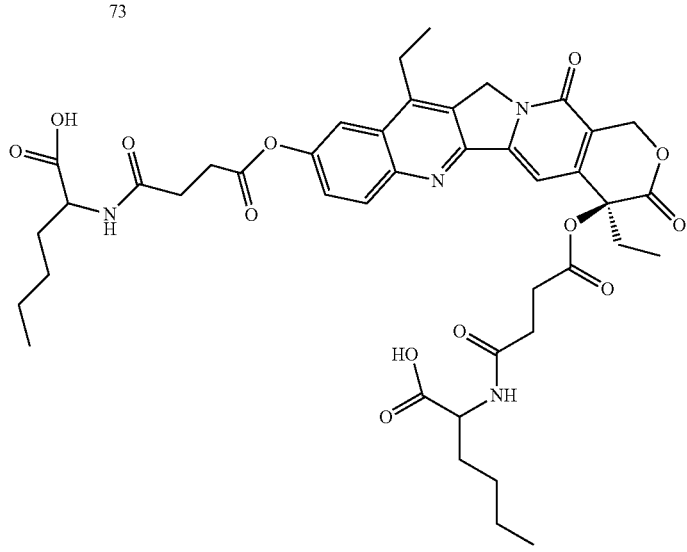

FL-038

1. Compound 2 (28.5 g) in THF (150 ml) was added to LDA (2.2 eq) and kept at −78° C. in dry THF (150 ml) under nitrogen. After 30 min, 1-iodobutane (13 g) was added to the reaction mixture. After 2 h, the mixture was allowed to warm slowly to room temperature and stirred overnight. The reaction was quenched by addition of water (100 ml) to the mixture at 0° C. The mixture was then extracted with $CH_2Cl_2$ (200 ml*3), the product was purified by silica gel column and recrystallized by 5% EA/PE to give compound 70 (15 g) as a white solid.
   1H NMR (300 MHz, $CDCl_3$) 7.6-7.7 (m, 2H), 7.4-7.5 (m, 3H), 7.3-7.4 (m, 3H), 7.1-7.2 (m, 2H), 3.8-4.0 (m, 1H), 1.4-1.5 (s, 9H), 1.2-1.4 (m, 6H), 0.8-1.0 (m, 3H).
2. To a solution of compound 70 (15 g) in 100 ml of THF at RT was added 110 ml of 10% aq. citric acid. The mixture was stirred overnight. The reaction was quenched by addition of water (200 ml) to the mixture at 0° C. The pH value is adjusted to about 7 using $NaHCO_3$. The resulting mixture was extracted with $CH_2Cl_2$ (150 ml*3). The organic phase was washed with saturated solution of sodium chloride and dried over $Na_2SO_4$. The solvent was removed on vacuum to give a crude product, which was purity by the silica gel column and recrystallized by 50% EA/PE to give compound 71 (8.2 g) as a white solid.
   1H NMR (300 MHz, $CDCl_3$) 3.3-3.4 (1H), 1.4-1.5 (s, 9H), 1.2-1.4 (m, 6H), 0.8-1.0 (3H).
3. Compound 71 (2.6 g) was dissolved into 15 ml pyridine and cooled down in an ice bath. Dihydrofuran-2,5-dione (1.8 g) was added. The reaction was stirred at RT overnight. Volatiles were removed. The organic phase was separated and the aqueous phase was extracted with DCM, and washed with 2N HCl. The combined the organic phase was dried over $Na_2SO_4$ and concentrated to give compound 72 (2.3 g) as a white solid.
   1H NMR (300 MHz, $CDCl_3$) 6.2-6.3 (bs, 1H), 4.4-4.5 (m, 1H), 2.7-2.8 (t, 2H), 2.5-2.6 (t, 2H), 1.8-1.9 (m, 1H), 1.4-1.5 (s, 9H), 1.2-1.4 (m, 6H), 0.8-0.9 (t, 3H).
4. Compound 72 (0.585 g) was dissolved into 10 ml DCM, and EDCI (0.5 g), DMAP (60 mg) and compound 9 (0.2 g) were added. The reaction was maintained at 25° C. for 12 h, and TLC indicated reaction was completed. The organic phase was separated and the aqueous phase was extracted with DCM, and washed with NaHCO$_3$(aq). The combined organic phase was dried over Na$_2$SO$_4$ and concentrated, and the residue was purified by flash chromatography using 2% MeOH/CHCl$_3$ to give compound 73 (200 mg).

1H NMR (300 MHz, CDCl$_3$) 8.3-8.4 (t, 1H), 7.8-7.9 (s, 1H), 7.5-7.6 (d, 1H), 7.2-7.3 (d, 1H), 6.0-6.2 (bs, 2H), 5.6-5.7 (d, 1H), 5.3-5.4 (d, 1H), 5.2-5.3 (s, 2H), 4.4-4.6 (m, 2H), 3.1-3.2 (t, 2H), 2.9-3.0 (t, 2H), 2.7-2.8 (t, 2H), 2.6-2.7 (t, 2H), 2.4-2.5 (m, 2H), 2.0-2.2 (m, 2H) 1.1-1.5 (m, 36H), 0.8-0.9 (t, 3H), 0.7-0.8 (t, 3H), 0.6-0.7 (m, 2H).

5. Compound 73 (200 mg) was dissolved into 10 ml DCM, and TFA (1.8 ml) were added. The reaction was maintained at 25° C. for 12 h, and TLC indicated reaction was completed. The solvent was removed and the residue was purified by flash chromatography using 5% MeOH/CHCl$_3$ to give FL-038 (140 mg).

1H NMR (300 MHz, DMSO-d6): 8.3-8.4 (bs, 1H), 8.2-8.3 (d, 1H), 7.9-8.0 (s, 1H), 7.6-7.7 (d, 1H), 7.2-7.3 (d, 1H), 5.5-5.6 (s, 2H), 5.2-5.43 (s, 2H), 4.4-4.6 (m, 2H), 3.1-3.2 (t, 2H), 2.9-3.0 (t, 2H), 2.7-2.8 (t, 2H), 2.6-2.7 (t, 2H), 2.4-2.5 (m, 2H), 2.0-2.2 (m, 2H), 1.1-1.5 (m, 18H), 0.8-0.9 (t, 3H), 0.7-0.8 (t, 3H), 0.6-0.7 (m, 2H).

LCMS: 819.4 (M+1)$^+$

Synthesis of FL-039

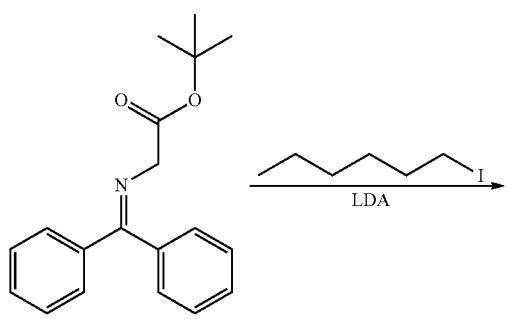

2

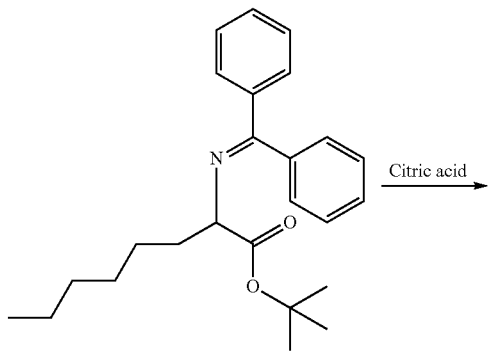

66

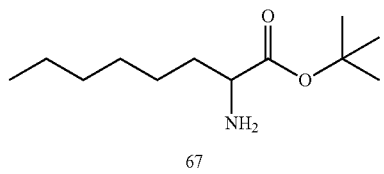

67

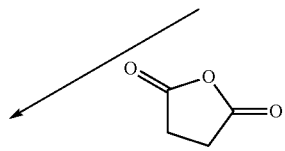

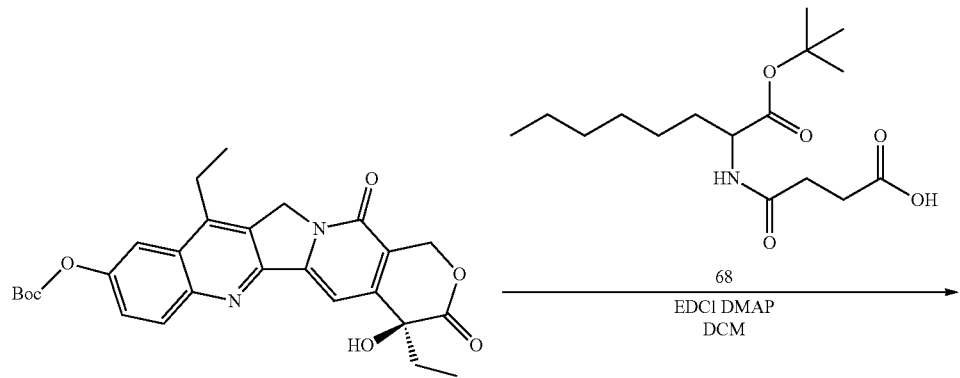

10

68
EDCl DMAP
DCM

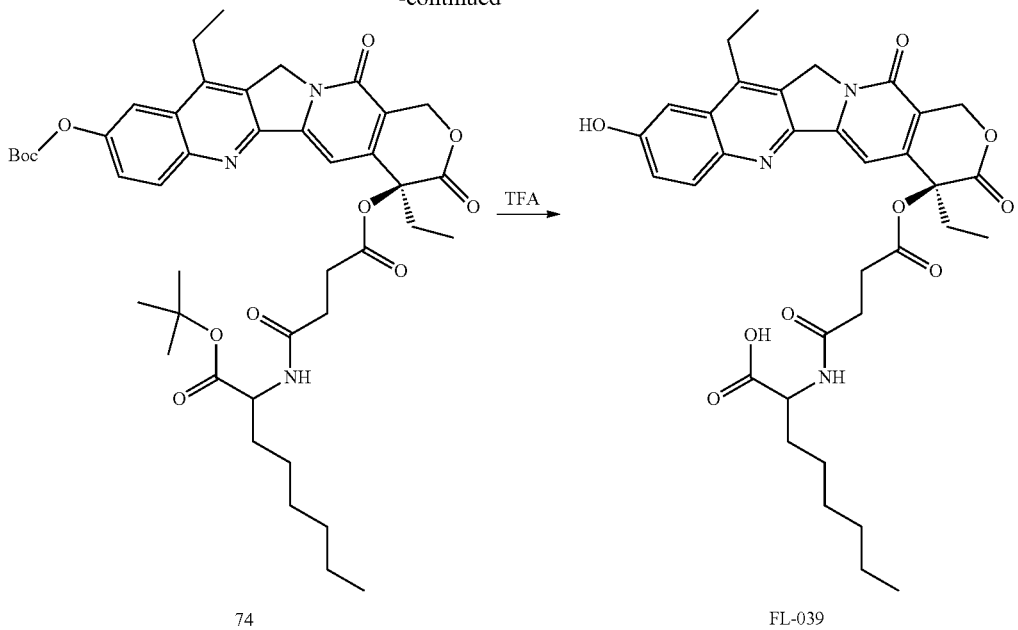

1. Compound 2 (28.5 g) in THF (150 ml) was added to LDA (2.2 eq) and kept at −78° C. in dry THF (150 ml) under nitrogen. After 30 min, 1-iodohexane (14.1 g) was added to the reaction mixture. After 2 h, the mixture was allowed to warm slowly to room temperature and stirred overnight. The reaction was quenched by addition of water (100 ml) to the mixture at 0° C. The mixture was then extracted with $CH_2Cl_2$ (200 ml*3), the product was purified by silica gel column and recrystallized by 5% EA/PE to give compound 66 (16 g) as a white solid.
   1H NMR (300 MHz, $CDCl_3$) 7.6-7.7 (m, 2H), 7.4-7.5 (m, 3H), 7.3-7.4 (m, 3H), 7.1-7.2 (m, 2H), 3.8-4.0 (m, 1H), 1.4-1.5 (s, 9H), 1.2-1.4 (m, 10H), 0.8-1.0 (m, 3H).
2. To a solution of compound 66 (16 g) in 100 ml of THF at RT was added 110 ml of 10% aq. Citric acid. The mixture was stirred overnight. The reaction was quenched by addition of water (200 ml) to the mixture at 0° C. The pH value is adjusted to about 7 using $NaHCO_3$. The resulting mixture was extracted with $CH_2Cl_2$ (150 ml*3). The organic phase was washed with saturated solution of sodium chloride and dried over $Na_2SO_4$. The solvent was removed on vacuum to give a crude product, which was purity by the silica gel column and recrystallized by 50% EA/PE to give compound 67 (8.5 g) as a white solid.
   1H NMR (300 MHz, $CDCl_3$): 3.3-3.4 (1H), 1.4-1.5 (s, 9H), 1.2-1.4 (m, 6H), 0.8-1.0 (3H).
3. Compound 67 (2.66 g) was dissolved into 15 ml pyridine and cooled down in an ice bath. Dihydrofuran-2,5-dione (1.75 g) was added. The reaction was stirred at RT overnight. Volatiles were removed. The organic phase was separated and the aqueous phase was extracted with DCM, and washed with 2N HCl. The combined the organic phase was dried over $Na_2SO_4$ and concentrated to give compound 68 (2.35 g) as a white solid.
   1H NMR (300 MHz, $CDCl_3$): 6.2-6.3 (bs, 1H), 4.4-4.5 (m, 1H), 2.7-2.8 (t, 2H), 2.5-2.6 (t, 2H), 1.8-1.9 (m, 1H), 1.4-1.5 (s, 9H), 1.2-1.4 (m, 10H), 0.8-0.9 (t, 3H).
4. Compound 69 (0.192 g) was dissolved into 10 ml DCM, and EDCI (0.21 g), DMAP (20 mg) and compound 10 (0.15 g) were added. The reaction was maintained at 25 D for 12 h, and TLC indicated reaction was completed. The organic phase was separated and the aqueous phase was extracted with DCM, and washed with $NaHCO_3$(aq). The combined organic phase was dried over $Na_2SO_4$ and concentrated, and the residue was purified by flash chromatography using 2% MeOH/$CHCl_3$ to give compound 74 (65 mg).
   1H NMR (300 MHz, $CDCl_3$): 8.2-8.3 (d, 1H), 7.4-7.5 (s, 2H), 7.0-7.1 (d, 1H), 7.2-7.3 (d, 1H), 6.3-6.4 (bs, 1H), 5.5-5.6 (d, 1H), 5.4-5.5 (d, 1H), 5.2-5.3 (s, 2H), 4.2-4.3 (m, 1H), 3.1-3.2 (t, 2H), 2.4-2.5 (m, 2H), 2.0-2.2 (m, 2H), 1.1-1.5 (m, 1 OH), 0.8-0.9 (t, 3H), 0.7-0.8 (t, 3H), 0.6-0.7 (m, 2H).
5. Compound 74 (65 mg) was dissolved into 10 ml DCM, and TFA (1.1 ml) were added. The reaction was maintained at 25 □ for 12 h, and TLC indicated reaction was completed. The solvent was removed and the residue was purified by flash chromatography using 5% MeOH/$CHCl_3$ to give FL-039 (35 mg).
   1H NMR (300 MHz, DMSO-d6): 8.3-8.4 (bs, 1H), 8.2-8.3 (d, 1H), 7.4-7.5 (s, 2H), 7.0-7.1 (d, 1H), 7.2-7.3 (d, 1H), 5.5-5.6 (s, 2H), 5.2-5.4 (s, 2H), 4.2-4.3 (m, 1H), 3.1-3.2 (t, 2H), 2.4-2.5 (m, 2H), 2.0-2.2 (m, 2H), 1.1-1.5 (m, 10H), 0.8-0.9 (t, 3H), 0.7-0.8 (t, 3H), 0.6-0.7 (m, 2H).
   LCMS: 634.4 $(M+1)^+$ Synthesis of FL-040
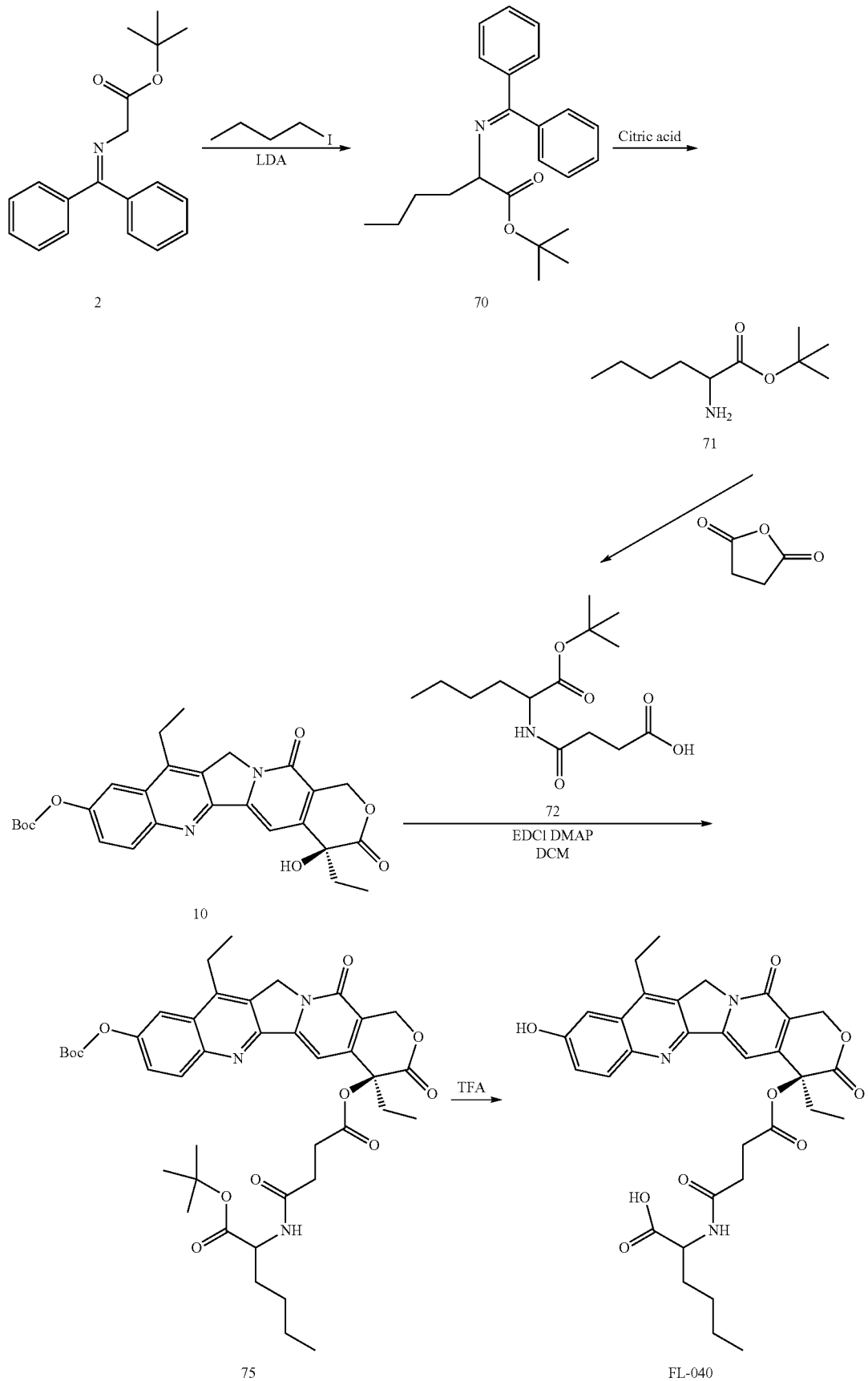

1. Compound 2 (28.5 g) in THF (150 ml) was added to LDA (2.2 eq) and kept at −78 □ in dry THF (150 ml) under nitrogen. After 30 min, 1-iodobutane (13 g) was added to the reaction mixture. After 2 h, the mixture was allowed to warm slowly to room temperature and stirred overnight. The reaction was quenched by addition of water (100 ml) to the mixture at 0□. The mixture was then extracted with $CH_2Cl_2$ (200 ml*3), the product was purified by silica gel column and recrystallized by 5% EA/PE to give compound 70 (15 g) as a white solid.
   1H NMR (300 MHz, $CDCl_3$): 7.6-7.7 (m, 2H), 7.4-7.5 (m, 3H), 7.3-7.4 (m, 3H), 7.1-7.2 (m, 2H), 3.8-4.0 (m, 1H), 1.4-1.5 (s, 9H), 1.2-1.4 (m, 6H), 0.8-1.0 (m, 3H).

2. To a solution of compound 70 (15 g) in 100 ml of THF at RT was added 110 ml of 10% aq. Citric acid. The mixture was stirred overnight. The reaction was quenched by addition of water (200 ml) to the mixture at 0□. The pH value is adjusted to about 7 using $NaHCO_3$. The resulting mixture was extracted with $CH_2Cl_2$ (150 ml*3). The organic phase was washed with saturated solution of sodium chloride and dried over $Na_2SO_4$. The solvent was removed on vacuum to give a crude product, which was purity by the silica gel column and recrystallized by 50 EA/PE to give compound 71 (8.2 g) as a white solid.
   1H NMR (300 MHz, $CDCl_3$): 3.3-3.4 (1H), 1.4-1.5 (s, 9H), 1.2-1.4 (m, 6H), 0.8-1.0 (3H).

3. Compound 71 (2.6 g) was dissolved into 15 ml pyridine and cooled down in an ice bath. Dihydrofuran-2,5-dione (1.8 g) was added. The reaction was stirred at RT overnight. Volatiles were removed. The organic phase was separated and the aqueous phase was extracted with DCM, and washed with 2N HCl. The combined the organic phase was dried over $Na_2SO_4$ and concentrated to give compound 72 (2.3 g) as a white solid.
   1H NMR (300 MHz, $CDCl_3$): 6.2-6.3 (bs, 1H), 4.4-4.5 (m, 1H), 2.7-2.8 (t, 2H), 2.5-2.6 (t, 2H), 1.8-1.9 (m, 1H), 1.4-1.5 (s, 9H), 1.2-1.4 (m, 6H), 0.8-0.9 (t, 3H).

4. Compound 72 (0.175 g) was dissolved into 10 ml DCM, and EDCI (0.2 g), DMAP (18 mg) and compound 10 (0.15 g) were added. The reaction was maintained at 25 for 12 h, and TLC indicated reaction was completed. The organic phase was separated and the aqueous phase was extracted with DCM, and washed with $NaHCO_3$(aq). The combined organic phase was dried over $Na_2SO_4$ and concentrated, and the residue was purified by flash chromatography using 2% MeOH/$CHCl_3$ to give compound 75 (120 mg).
   H NMR (300 MHz, $CDCl_3$): 8.3-8.4 (t, 1H), 7.8-7.9 (s, 1H), 7.5-7.6 (d, 1H), 7.2-7.3 (d, 1H), 6.0-6.2 (bs, 1H), 5.6-5.7 (d, 1H), 5.3-5.4 (d, 1H), 5.2-5.3 (s, 2H), 4.4-4.6 (m, 1H), 3.1-3.2 (t, 2H), 2.7-2.8 (t, 2H), 2.6-2.7 (t, 2H), 2.0-2.2 (m, 2H), 1.1-1.5 (m, 17H), 0.8-0.9 (t, 3H), 0.7-0.8 (t, 3H), 0.6-0.7 (m, 2H).

5. Compound 75 (120 mg) was dissolved into 10 ml DCM, and TFA (1.8 ml) were added. The reaction was maintained at 25 □ for 12 h, and TLC indicated reaction was completed. The solvent was removed and the residue was purified by flash chromatography using 5% MeOH/$CHCl_3$ to give FL-040 (90 mg).
   1H NMR (300 MHz, DMSO-d6): 12.3-12.6 (bs, 1H), 10.3-10.6 (bs, 1H), 8.3-8.4 (bs, 1H), 8.2-8.3 (d, 1H), 7.4-7.5 (d, 2H), 7.0-7.2 (d, 1H), 5.5-5.6 (s, 2H), 5.2-5.43 (s, 2H), 4.2-4.4 (m, 1H), 3.1-3.2 (t, 2H), 2.9-3.0 (t, 2H), 2.0-2.2 (m, 2H), 1.1-1.5 (m, 8H), 0.8-0.9 (t, 3H), 0.7-0.8 (t, 3H), 0.6-0.7 (m, 2H).
   LCMS: 606.4 $(M+1)^+$ Synthesis of FL-041

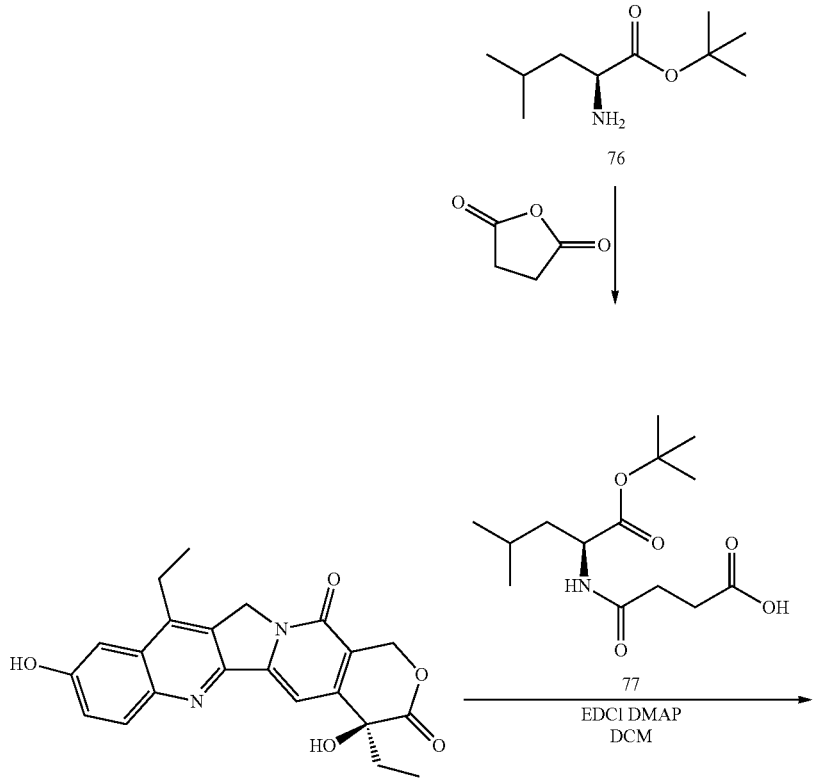

-continued

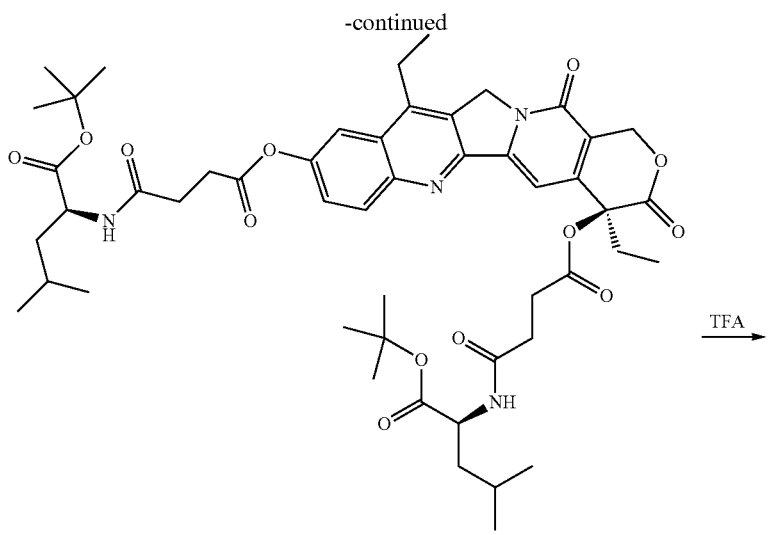

78

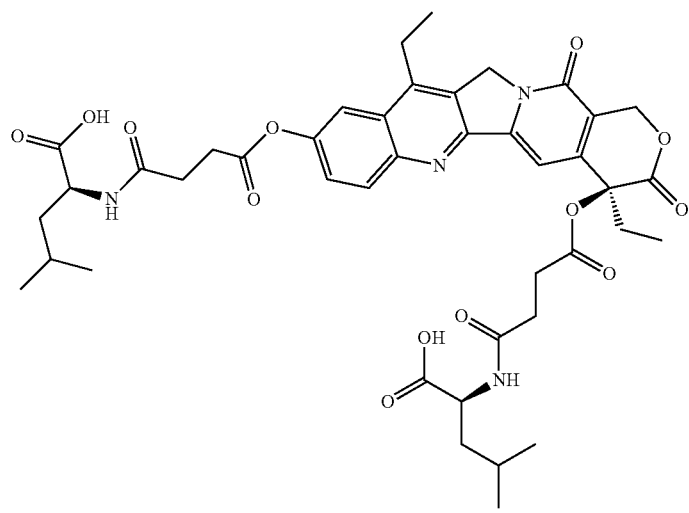

FL-041

1. Compound 76 (2.23 g) was dissolved into 15 ml pyridine and cooled down in an ice bath. Dihydrofuran-2,5-dione (1.5 g) was added. The reaction was stirred at RT overnight. Volatiles were removed. The organic phase was separated and the aqueous phase was extracted with DCM, and washed with 2N HCl. The combined the organic phase was dried over $Na_2SO_4$ and concentrated to give compound 77 (2.5 g) as a white solid.
   1H NMR (300 MHz, $CDCl_3$) 6.2-6.3 (bs, 1H), 4.1-4.2 (m, 1H), 2.7-2.8 (t, 2H), 2.5-2.6 (t, 2H), 1.8-1.9 (m, 2H), 1.4-1.5 (s, 9H), 1.0-1.1 (m, 6H).
2. Compound 77 (0.585 g) was dissolved into 10 ml DCM, and EDCI (0.5 g), DMAP (60 mg) and compound 9 (0.2 g) were added. The reaction was maintained at 25 C for 12 h, and TLC indicated reaction was completed. The organic phase was separated and the aqueous phase was extracted with DCM, and washed with $NaHCO_3$(aq). The combined organic phase was dried over $Na_2SO_4$ and concentrated, and the residue was purified by flash chromatography using 2% MeOH/$CHCl_3$ to give compound 78 (180 mg).
   1H NMR (300 MHz, $CDCl_3$): 8.3-8.4 (t, 1H), 7.8-7.9 (s, 1H), 7.5-7.6 (d, 1H), 7.2-7.3 (d, 1H), 6.0-6.2 (bs, 2H), 5.6-5.7 (d, 1H), 5.3-5.4 (d, 1H), 5.2-5.3 (s, 2H), 4.4-4.6 (m, 2H), 3.1-3.2 (t, 2H), 2.9-3.0 (t, 2H), 2.7-2.8 (t, 2H), 2.6-2.7 (t, 2H), 2.4-2.5 (m, 2H), 2.0-2.2 (m, 2H), 1.1-1.5 (m, 36H), 0.8-0.9 (t, 3H), 0.7-0.8 (t, 3H), 0.6-0.7 (m, 2H).
3. Compound 78 (180 mg) was dissolved into 10 ml DCM, and TFA (1.9 ml) were added. The reaction was maintained at 25 C for 12 h, and TLC indicated reaction was completed. The solvent was removed and the residue was purified by flash chromatography using 5% MeOH/$CHCl_3$ to give FL-041 (125 mg).
   1H NMR (300 MHz, DMSO-d6): 12.5-12.7 (bs, 1H), 8.3-8.4 (bs, 2H), 8.2-8.3 (d, 1H), 7.9-8.0 (s, 1H), 7.6-7.7 (d, 1H), 7.2-7.3 (d, 1H), 5.5-5.6 (s, 2H), 5.2-5.43 (s, 2H), 4.4-4.6 (m, 2H), 3.1-3.2 (t, 2H), 2.9-3.0 (t, 2H), 2.7-2.8 (t, 2H), 2.6-2.7 (t, 2H), 2.4-2.5 (m, 2H), 2.0-2.2 (m, 2H), 1.1-1.5 (m, 12H), 0.7-0.9 (t, 15H), 0.6-0.7 (m, 3H).
   LCMS: 819.4 $(M+1)^+$ Synthesis of FL-042
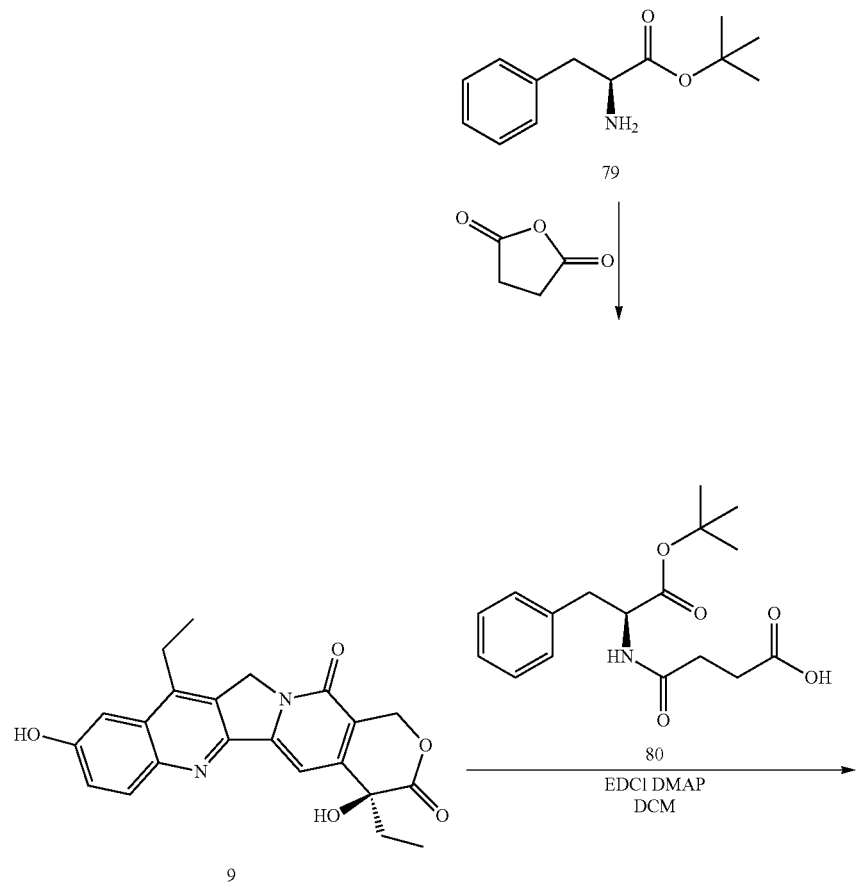
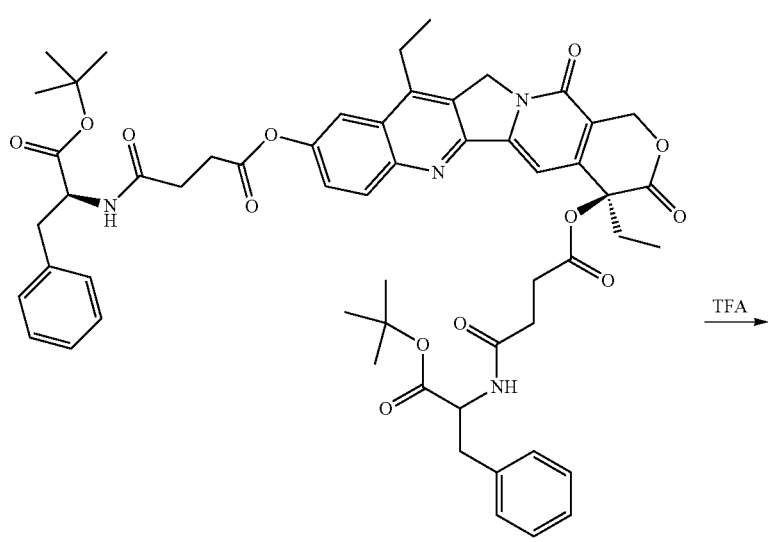

-continued

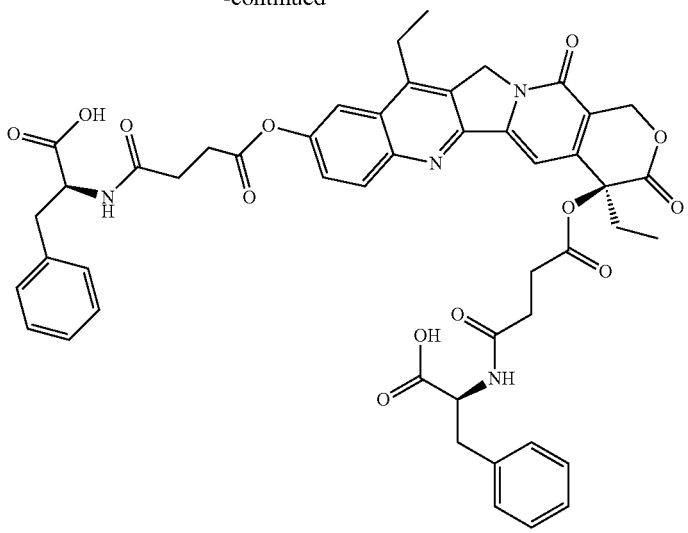

FL-042

1. Compound 79 (0.3 g) was dissolved into 10 ml pyridine and cooled down in an ice bath. Dihydrofuran-2,5-dione (0.76 g) was added. The reaction was stirred at RT overnight. Volatiles were removed. The organic phase was separated and the aqueous phase was extracted with DCM, and washed with 2N HCl. The combined the organic phase was dried over $Na_2SO_4$ and concentrated to give compound 80 (1.4 g) as a white solid.

1H NMR (300 MHz, $CDCl_3$): 7.2-7.4 (m, 5H), 6.2-6.3 (bs, 1H), 4.4-4.5 (m, 1H), 3.2-3.3 (t, 2H), 2.5-2.6 (t, 2H), 1.8-1.9 (m, 2H), 1.4-1.5 (s, 9H).

2. Compound 80 (0.655 g) was dissolved into 10 ml DCM, and EDCI (0.5 g), DMAP (60 mg) and compound 9 (0.2 g) were added. The reaction was maintained at 25□ for 12 h, and TLC indicated reaction was completed. The organic phase was separated and the aqueous phase was extracted with DCM, and washed with $NaHCO_3$(aq). The combined organic phase was dried over $Na_2SO_4$ and concentrated, and the residue was purified by flash chromatography using 2% $MeOH/CHCl_3$ to give compound 81 (186 mg).

1H NMR (300 MHz, $CDCl_3$): 8.3-8.4 (t, 1H), 7.8-7.9 (s, 1H), 7.5-7.6 (d, 1H), 7.2-7.3 (m, 6H), 6.0-6.2 (bs, 2H), 5.6-5.7 (d, 1H), 5.3-5.4 (d, 1H), 5.2-5.3 (s, 2H), 4.4-4.6 (m, 2H), 3.1-3.2 (t, 4H), 2.9-3.0 (t, 2H), 2.7-2.8 (t, 4H), 2.4-2.5 (m, 2H), 2.0-2.2 (m, 2H), 1.4-1.5 (m, 18H), 1.1-1.2 (t, 3H), 0.7-0.8 (t, 3H).

3. Compound 81 (186 mg) was dissolved into 10 ml DCM, and TFA (1.9 ml) were added. The reaction was maintained at 25□ for 12 h, and TLC indicated reaction was completed. The solvent was removed and the residue was purified by flash chromatography using 5% $MeOH/CHCl_3$ to give FL-043 (125 mg).

11H NMR (300 MHz, DMSO-d6): 12.7-12.9 (bs, 1H), 8.3-8.4 (bs, 2H), 8.2-8.3 (d, 1H), 7.9-8.0 (s, 1H), 7.6-7.7 (d, 1H), 7.2-7.3 (m, 6H), 5.5-5.6 (s, 2H), 5.2-5.43 (s, 2H), 4.4-4.6 (m, 2H), 3.1-3.2 (t, 4H), 2.9-3.0 (t, 4H), 2.7-2.8 (t, 2H), 2.6-2.7 (t, 2H), 2.4-2.5 (m, 2H), 1.1-1.3 (m, 3H), 0.7-0.9 (t, 3H).

LCMS: 887.4 (M+1)$^+$

Synthesis of FL-043

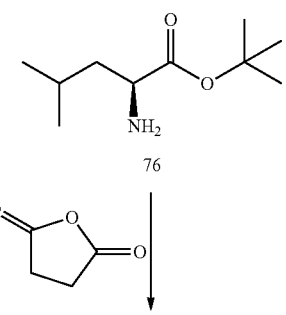

-continued
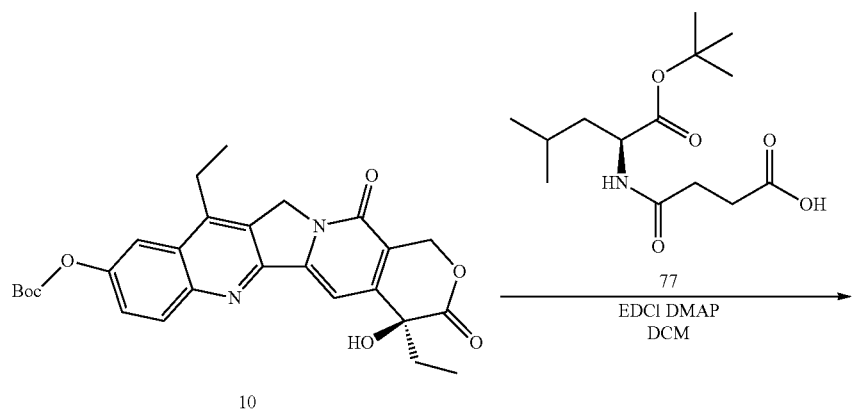
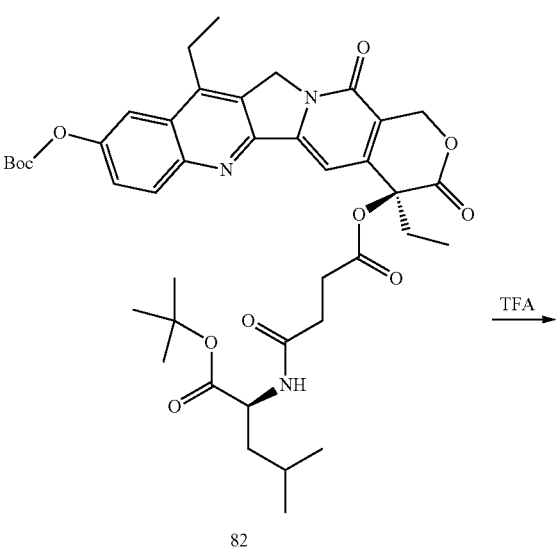
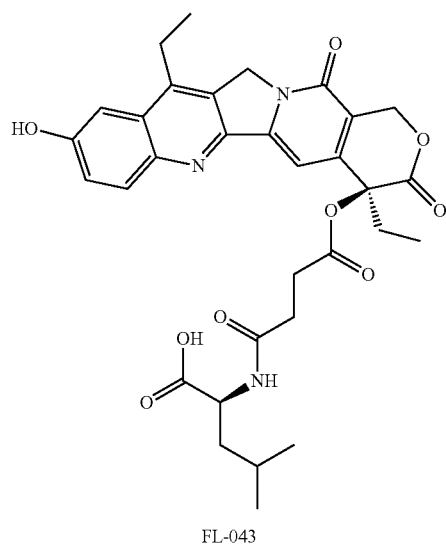 [SMILES: CCc1c2c(nc3ccc(O)cc13)-c1cc3c(c(=O)n1C2)COC(=O)[C@@]3(CC)OC(=O)CCC(=O)N[C@@H](CC(C)C)C(=O)O]

1. Compound 76 (2.33 g) was dissolved into 15 ml pyridine and cooled down in an ice bath. Dihydrofuran-2,5-dione (1.5 g) was added. The reaction was stirred at RT overnight. Volatiles were removed. The organic phase was separated and the aqueous phase was extracted with DCM, and washed with 2N HCl. The combined the organic phase was dried over $Na_2SO_4$ and concentrated to give compound 77 (2.4 g) as a white solid.
   1H NMR (300 MHz, $CDCl_3$): 6.2-6.3 (bs, 1H), 4.1-4.2 (m, 1H), 2.7-2.8 (t, 2H), 2.5-2.6 (t, 2H), 1.8-1.9 (m, 2H), 1.4-1.5 (s, 9H), 1.0-1.5 (m, 6H), 0.8-0.9 (t, 3H), 0.6-0.7 (m, 6H).
2. Compound 77 (0.28 g) was dissolved into 10 ml DCM, and EDCI (0.337 g), DMAP (30 mg) and compound 10 (0.24 g) were added. The reaction was maintained at 25□ for 12 h, and TLC indicated reaction was completed. The organic phase was separated and the aqueous phase was extracted with DCM, and washed with $NaHCO_3$(aq). The combined organic phase was dried over $Na_2SO_4$ and concentrated, and the residue was purified by flash chromatography using 2% MeOH/$CHCl_3$ to give compound 82 (205 mg).
   1H NMR (300 MHz, $CDCl_3$): 8.3-8.4 (t, 1H), 7.8-7.9 (s, 1H), 7.5-7.6 (d, 1H), 7.2-7.3 (d, 1H), 6.0-6.2 (bs, 1H), 5.6-5.7 (d, 1H), 5.3-5.4 (d, 1H), 5.2-5.3 (s, 2H), 4.4-4.6 (m, 1H), 3.1-3.2 (t, 2H), 2.9-3.0 (t, 2H), 2.4-2.5 (m, 2H), 2.0-2.2 (m, 2H), 1.1-1.5 (m, 21H), 0.8-0.9 (t, 3H), 0.6-0.7 (m, 6H).
3. Compound 82 (205 mg) was dissolved into 10 ml DCM, and TFA (1.8 ml) were added. The reaction was maintained at 25□ for 12 h, and TLC indicated reaction was completed. The solvent was removed and the residue was purified by flash chromatography using 5% MeOH/$CHCl_3$ to give FL-043 (150 mg).
   1H NMR (300 MHz, DMSO-d6): 12.5-12.7 (bs, 1H), 8.3-8.4 (bs, 1H), 8.2-8.3 (d, 1H), 7.3-7.4 (s, 2H), 7.0-7.1 (s, 1H), 5.5-5.6 (s, 2H), 5.2-5.43 (s, 2H), 4.4-4.6 (m, 1H), 3.1-3.2 (t, 2H), 2.7-2.8 (t, 2H), 2.4-2.5 (m, 2H), 2.0-2.2 (m, 2H), 1.1-1.4 (m, 6H), 0.6-0.9 (m, 9H).
   LCMS: 606.4 $(M+1)^+$ Synthesis of FL-044

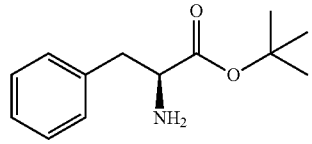

79

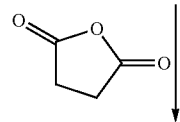

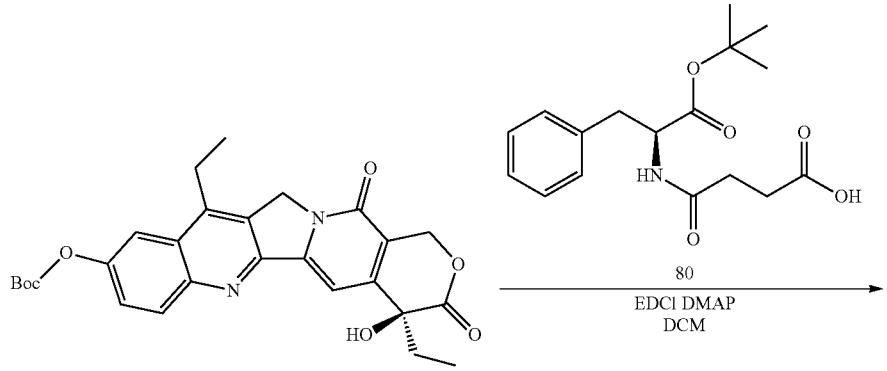

10

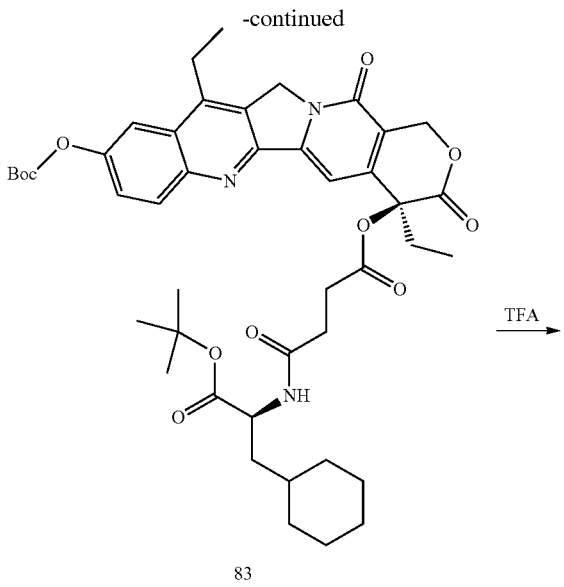

83

TFA →

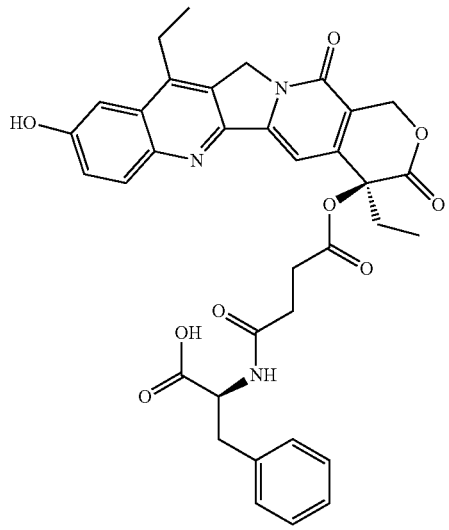

FL-044

1. Compound 79 (1.3 g) was dissolved into 15 ml pyridine and cooled down in an ice bath. Dihydrofuran-2,5-dione (0.76 g) was added. The reaction was stirred at RT overnight. Volatiles were removed. The organic phase was separated and the aqueous phase was extracted with DCM, and washed with 2N HCl. The combined the organic phase was dried over $Na_2SO_4$ and concentrated to give compound 80 (1.3 g) as a white solid.

1H NMR (300 MHz, $CDCl_3$): 7.2-7.4 (m, 5H), 6.2-6.3 (bs, 1H), 4.4-4.5 (m, 1H), 3.2-3.3 (t, 2H), 2.5-2.6 (t, 2H), 1.8-1.9 (m, 2H), 1.4-1.5 (s, 9H).

2. Compound 80 (0.2 g) was dissolved into 10 ml DCM, and EDCI (0.21 g), DMAP (20 mg) and compound 10 (0.15 g) were added. The reaction was maintained at 25□ for 12 h, and TLC indicated reaction was completed. The organic phase was separated and the aqueous phase was extracted with DCM, and washed with $NaHCO_3$(aq). The combined organic phase was dried over $Na_2SO_4$ and concentrated, and the residue was purified by flash chromatography using 2% MeOH/$CHCl_3$ to give compound 83 (120 mg).

1H NMR (300 MHz, $CDCl_3$): 8.3-8.4 (t, 1H), 7.8-7.9 (s, 1H), 7.5-7.6 (d, 1H), 7.2-7.3 (m, 6H), 6.0-6.2 (bs, 1H), 5.6-5.7 (d, 1H), 5.3-5.4 (d, 1H), 5.2-5.3 (s, 2H), 4.4-4.6 (m, 1H), 3.1-3.2 (t, 2H), 2.7-2.8 (t, 2H), 2.4-2.5 (m, 2H), 2.0-2.2 (m, 2H), 1.4-1.5 (m, 18H), 1.1-1.2 (t, 3H), 0.7-0.8 (t, 3H).

3. Compound 83 (120 mg) was dissolved into 10 ml DCM, and TFA (1.8 ml) were added. The reaction was maintained at 25□ for 12 h, and TLC indicated reaction was completed. The solvent was removed and the residue was purified by flash chromatography using 5% MeOH/$CHCl_3$ to give FL-044 (100 mg).

11H NMR (300 MHz, DMSO-d6): 12.7-12.9 (bs, 1H), 8.3-8.4 (bs, 1H), 8.2-8.3 (d, 1H), 7.9-8.0 (s, 1H), 7.6-7.7 (d, 1H), 7.2-7.3 (m, 6H), 5.5-5.6 (s, 1H), 5.2-5.43 (s, 2H), 4.4-4.6 (m, 1H), 3.1-3.2 (t, 2H), 2.6-2.7 (t, 2H), 2.0-2.1 (m, 2H), 1.1-1.3 (m, 3H), 0.7-0.9 (t, 3H).

LCMS: 640.4 $(M+1)^+$

Synthesis of TL-001A
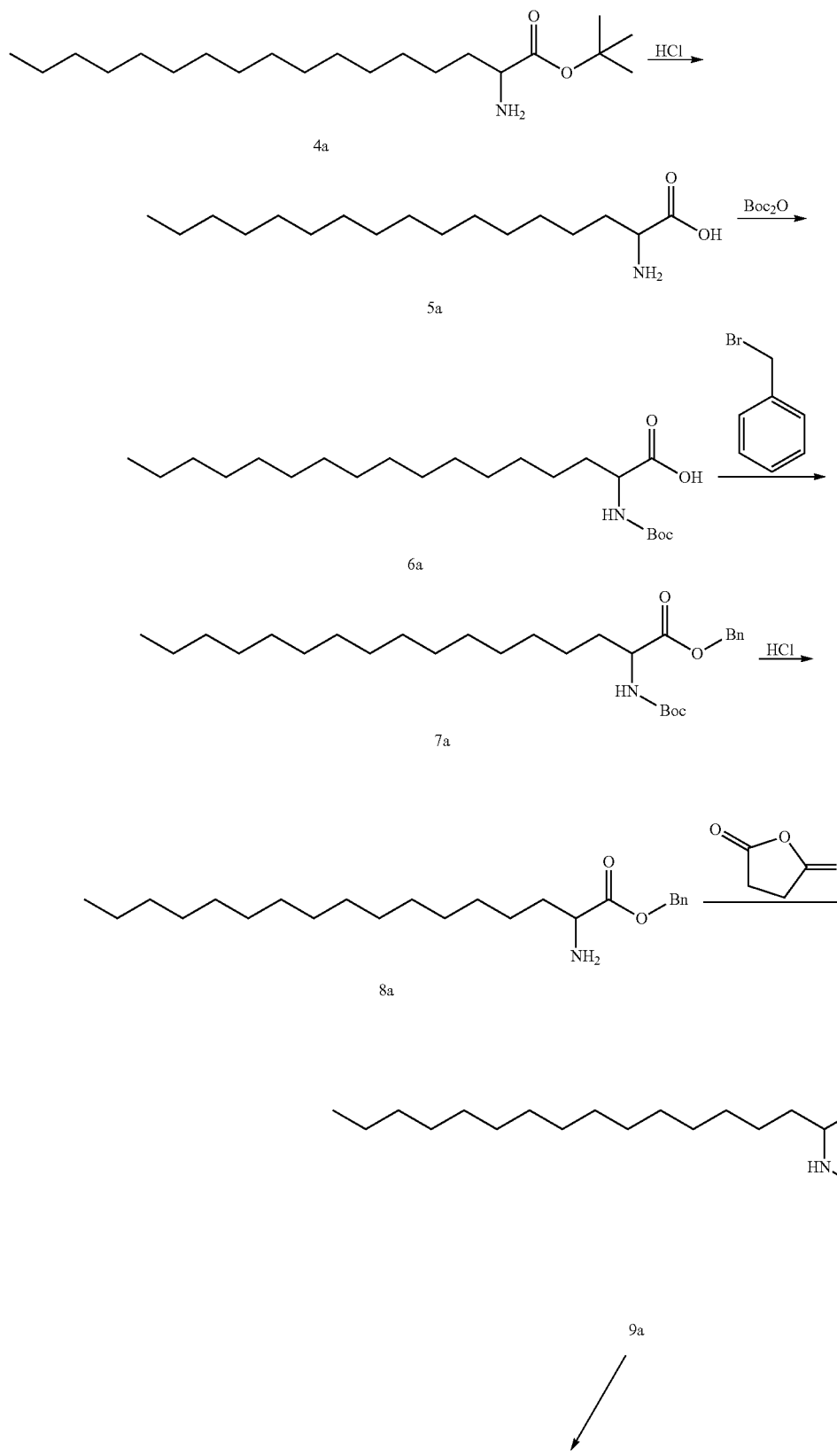

-continued
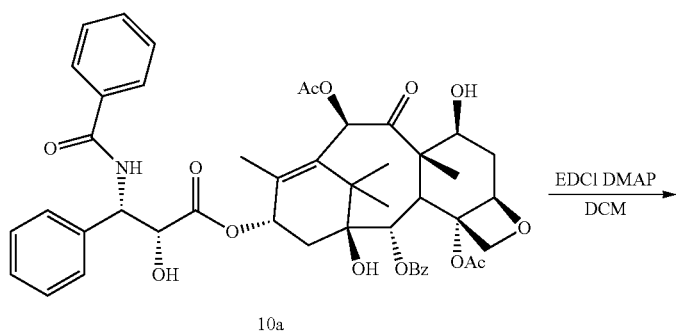
10a
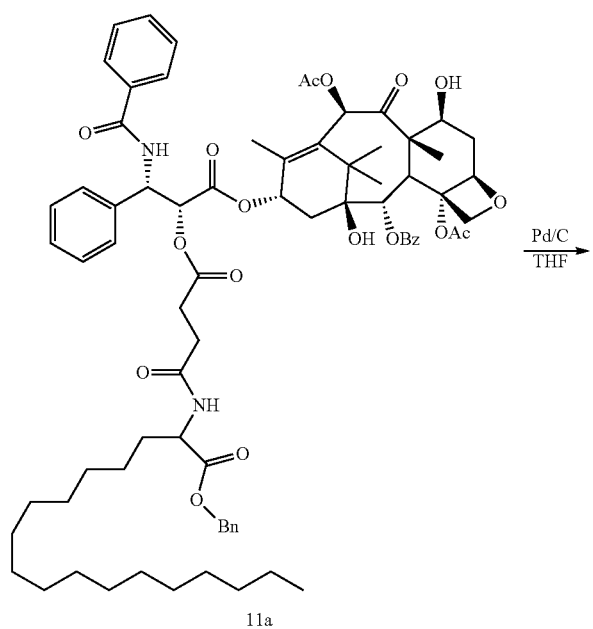
11a
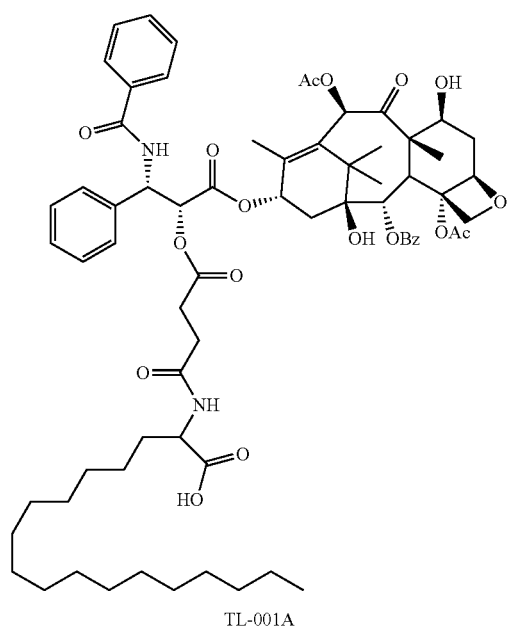
TL-001A

1. Compound 4a (3.9 g) was dissolved into 15 ml DCM and cooled down in an ice bath. HCl.Et$_2$O (5 ml, 4N) was added. The reaction was stirred at RT overnight. Volatiles were removed to give compound 5a (3.2 g yield about 92%) as a white solid.
2. Compound 5a (3.2 g) was dissolved into 20 ml 1,4-dioxane and 20 ml H$_2$O, and cooled down in an ice bath. NaOH (0.9 g, 0.023 mol) was added, followed by Boc$_2$O (3.6 g, 0.023 mol). The reaction was maintained at 25° C. for 48 h, and TLC indicated reaction was completed. The organic phase was separated and the aqueous phase was extracted with DCM The combined the organic phase was dried over Na$_2$SO$_4$ and concentrated to give compound 6a (2 g yield about 56%) as a white solid.
3. Compound 6a (2 g) was dissolved into 15 ml THF, and TEA (0.9 ml) and benzyl bromide (0.9 g) were added. The reaction was maintained at 25□ for 12 h, and TLC indicated reaction was completed. Water (50 ml) was added. The resultant mixture was extracted with CH$_2$Cl$_2$ (30 ml*3). Organic phase washed with saturated solution of sodium chloride and dried over anhydrous Na$_2$SO$_4$. The solvent was removed on vacuum to give a crude product, which was purified by a silica gel and recrystallized by 5 EA/PE to give compound 7a (2.3 g) as a white solid.
4. Compound 7a (2.3 g) was dissolved into 15 ml DCM and cooled down in an ice bath. HCl.Et$_2$O (5 ml, 4N) was added. The reaction was stirred at RT overnight. Volatiles were removed to give compound 8a (1.8 g) as a white solid.
5. Compound 8a (1.8 g) was dissolved into 10 ml pyridine and cooled down in an ice bath. Dihydrofuran-2,5-dione (0.84 g) was added. The reaction was stirred at RT overnight. Volatiles were removed. The organic phase was separated and the aqueous phase was extracted with DCM, and washed with 2N HCl. The combined the organic phase was dried over Na$_2$SO$_4$ and concentrated to give compound 9a (1.75 g yield about 85%) as a white solid.
6. Compound 9a (0.13 g) was dissolved into 10 ml DCM, and EDCI (0.1 g), and DMAP (0.015 g), and Compound 10a (Taxol) (0.2 g) were added. The reaction was maintained at 25 C for 48 h, and TLC indicated reaction was completed. The organic phase was separated and the aqueous phase was extracted with DCM, and washed with NaHCO$_3$(aq). The combined organic phase was dried over Na$_2$SO$_4$ and concentrated, and the residue was purified by flash chromatography using 2% MeOH/CHCl$_3$ to give concentrated to give compound 11a (0.11 g) as a white solid.
7. Compound 11a (0.11 g) was dissolved into 10mlTHF, and Pd/C (0.01 g) was added, followed with H$_2$ (0.01 mPa). The reaction was maintained at 25 C for 5 h, and TLC indicated reaction was completed. After the filtration, the mixture was concentrated, and the residue was purified by flash chromatography using 5% MeOH/CHCl$_3$ to give concentrated to give TL-001A (60 mg) as a solid. 1H NMR (300 MHz, CDCl$_3$) 8.1-8.2 (t, 2H), 7.8-7.9 (t, 2H), 7.3-7.6 (m, 11H), 6.3-6.4 (t, 1H), 6.1-6.2 (t, 1H), 5.8-5.9 (t, 1H), 5.6-5.7 (t, 1H), 5.5-5.6 (t, 1H), 4.9-5.0 (t, 1H), 4.1-4.4 (m, 4H), 3.8-3.9 (m, 2H), 2.7-2.8 (m, 3H), 2.3-2.4 (m, 8H), 2.1-2.3 (m, 6H), 1.8-1.9 (s, 3H), 1.5-1.6 (s, 3H). 1.1-1.4 (m, 38H).

LC/MS: 1235.5 (M+1)$^+$

Example 1: Non-Covalently Bound Complex of FL-003 and HSA

FL-003

In each of 4 vials, 1 mg of FL-003 was dissolved in 0.2 ml EtOH. Then 0.6 ml of water was added into each of 4 vials. A slightly cloudy solution was obtained for all 4 vials. 24.2 mg, 17 mg, 14 mg, and 12 mg of HSA were added into each vial. After shaken for 5 minutes and then EtOH was removed under vacuum, a clear water solution was obtained for all 4 vials. The water solutions of the 4 vials were lyophilized overnight to give the slightly yellow solids, which were reconstituted by adding 0.5 ml water into the vials with 24.2 mg and 17 mg HSA and adding 0.3 ml water into the vials with 14 mg and 12 mg HSA. All 4 vials gave a clear slightly yellow solution.

| HSA | 24.2 mg | 17 mg | 14 mg | 12 mg |
|---|---|---|---|---|
| Ratio of drug: HSA | 3.5 | 5.1 | 6.1 | 7.2 |

Example 2: Non-Covalently Bound Complex of FL-007 and HSA

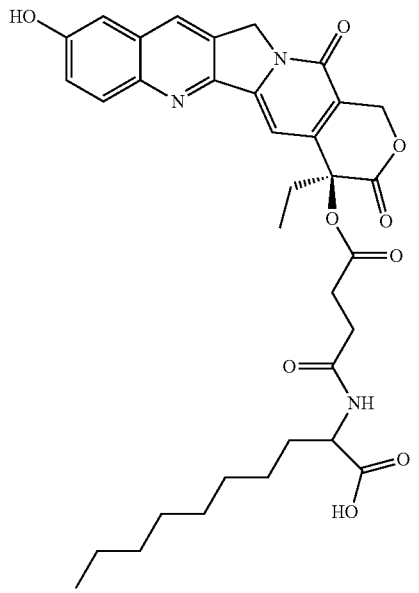

FL-007

In each of 5 vials, 1 mg of FL-007 was dissolved in 1.5 ml EtOH. Then 3 ml of water was added into each of 5 vials. A slightly cloudy solution was obtained for all 5 vials. 24.2 mg, 21 mg, 17 mg, 15 mg, and 13 mg of HSA were added into each vial. After shaken for 5 minutes and then EtOH was removed under vacuum, a clear or slightly cloudy water solution was obtained for all 5 vials. The water solutions of the 5 vials were lyophilized overnight to give the slightly yellow solids, which were reconstituted by adding 0.5 ml water into the vials with 24.2 mg, 17 mg and 15 mg HSA and adding 0.3 ml water into the vials with 15 mg and 13 mg HSA. All 5 vials gave a clear slightly yellow solution.

| HSA | 24.2 mg | 21 mg | 17 mg | 15 mg | 13 mg |
|---|---|---|---|---|---|
| Ratio of drug: HSA | 4.3 | 5 | 6.2 | 7 | 8.1 |

Example 3: Non-Covalently Bound Complex of FL-036 and HSA

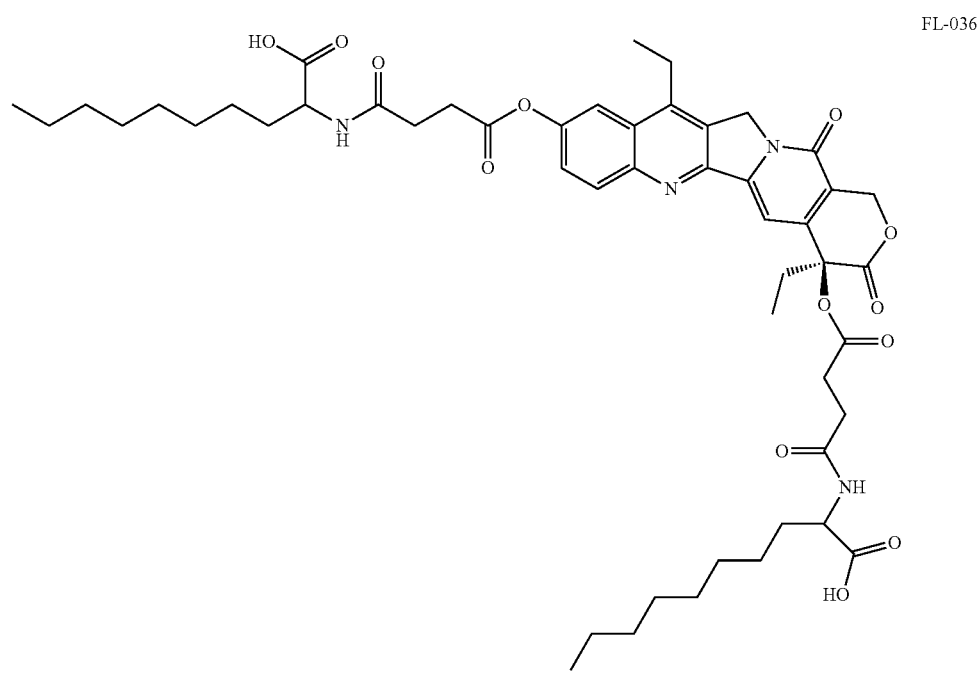 [SMILES: CCCCCCCCC(NC(=O)CCC(=O)Oc1ccc2nc3c(c(CC)c2c1)Cn1c-3cc2c(c1=O)COC(=O)[C@@]2(CC)OC(=O)CCC(=O)NC(CCCCCCCC)C(=O)O)C(=O)O]

FL-036

In each of 3 vials, 1 mg of FL-036 was dissolved in 0.5 ml EtOH. Then 1 ml of water was added into each of 3 vials. 10.5 mg, 9.5 mg, and 9 mg of HSA were added into each vial. After shaken for 5 minutes and then EtOH was removed under vacuum, a clear water solution was obtained for the vial with 10.5 mg HSA and a slightly cloudy solution was obtained for the vials with 9.5 mg and 9 mg HSA. The water solutions of the 3 vials were lyophilized overnight to give the slightly yellow solids, which were reconstituted by adding 0.3 ml water into each vial. A clear slightly yellow solution was obtained for the vial with 10.5 mg HSA and a slightly cloudy solution was obtained for the vials with 9.5 mg and 9 mg HSA.

| HSA | 10.5 mg | 9.5 mg | 9 mg |
| --- | --- | --- | --- |
| Ratio of drug: HSA | 6.8 | 7.5 | 7.9 |

Example 4: Non-Covalently Bound Complex of FL-037 and HSA

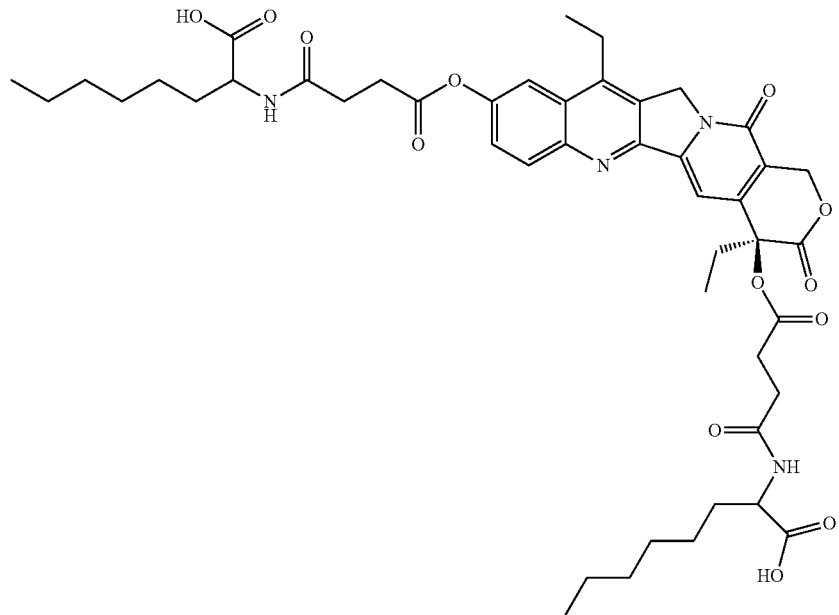

FL-037

In each of 3 vials, 1 mg of FL-037 was dissolved in 0.5 ml EtOH. Then 1 ml of water was added into each of 3 vials. 11 mg, 9.5 mg, and 8 mg of HSA were added into each vial. After shaken for 5 minutes and then EtOH was removed under vacuum, a clear water solution was obtained for the vial with 11 mg HSA and a slightly cloudy solution was obtained for the vials with 9.5 mg and 8 mg HSA. The water solutions of the 3 vials were lyophilized overnight to give the slightly yellow solids, which were reconstituted by adding 0.3 ml water into each vial. A clear slightly yellow solution was obtained for the vial with 11 mg HSA and a slightly cloudy solution was obtained for the vials with 9.5 mg and 8 mg HSA.

| HSA | 11 mg | 9.5 mg | 8 mg |
| --- | --- | --- | --- |
| Ratio of drug: HSA | 6.9 | 8 | 9.5 |

Example 5: Non-Covalently Bound Complex of FL-038 and HSA

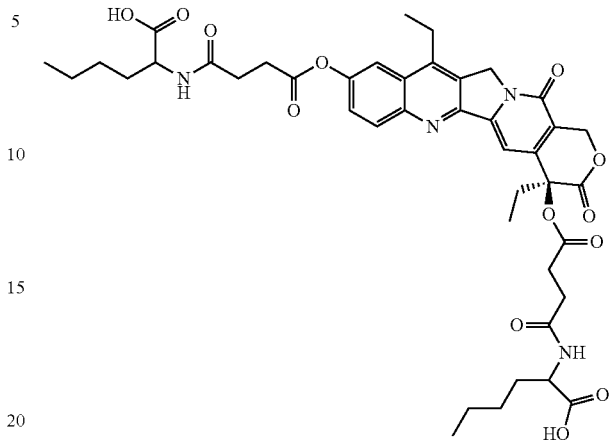

FL-038

In each of 7 vials, 1 mg of FL-038 was dissolved in 0.5 ml EtOH. Then 1.5 ml of water was added into each of 7 vials. 20 mg, 16 mg, 13.5 mg, 11.5 mg, 10 mg, 9 mg, and 8 mg of HSA were added into each vial. After shaken for 5 minutes and then EtOH was removed under vacuum, a clear water solution was obtained for all other 6 vials except for the vial with 8 mg HSA. The water solutions of the 7 vials were lyophilized overnight to give the slightly yellow solids, which were reconstituted by adding 0.4 ml water into the vials with 20 mg and 16 mg HSA, and adding 0.3 ml water into the other 5 vials. All other 6 vials gave a clear slightly yellow solution, except that the vial with 8 mg HSA gave a little cloudy solution.

| HSA | 20 mg | 16 mg | 13.5 mg | 11.5 mg | 10 mg | 9 mg | 8 mg |
|---|---|---|---|---|---|---|---|
| Ratio of drug:HSA | 4.1 | 5.1 | 6 | 7.1 | 8.1 | 9 | 10.2 |

Example 6: Non-Covalently Bound Complex of FL-040 and HSA

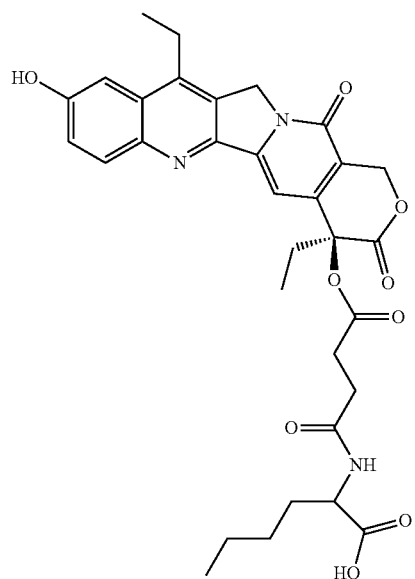

FL-040

In each of 7 vials, 1 mg of FL-040 was dissolved in 0.7 ml EtOH. Then 2.1 ml of water was added into each of 7 vials. A clear solution was obtained for all 7 vials. 22 mg, 18.3 mg, 15.7 mg, 13.7 mg, 12.2 mg, 1 mg, and 10 mg of HSA were added into each vial. After shaken for 5 minutes and then EtOH was removed under vacuum, a clear water solution was obtained for all other 6 vials except for the vial with 10 mg HSA. The water solutions of the 7 vials were lyophilized overnight to give the slightly yellow solids, which were reconstituted by adding 0.5 ml water into each vial. All other 6 vials gave a clear slightly yellow solution, except that the vial with 10 mg HSA gave a little cloudy solution.

| HSA | 22 mg | 18.3 mg | 15.7 mg | 13.7 mg | 12.2 mg | 11 mg | 10 mg |
|---|---|---|---|---|---|---|---|
| Ratio of drug:HSA | 5 | 6 | 7 | 8 | 9 | 10 | 11 |

Example 7: Non-Covalently Bound Complex of FL-041 and HSA

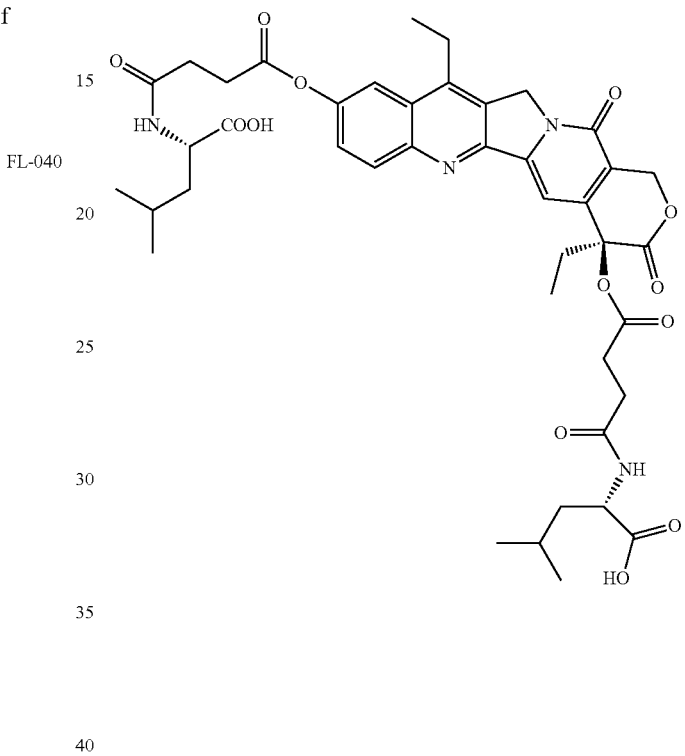

FL-041

In each of 3 vials, 1 mg of FL-041 was dissolved in 0.5 ml EtOH. Then 1.5 ml of water was added into each of 3 vials. 13.5 mg, 11.6 mg, and 10.2 mg of HSA were added into each vial. After shaken for 5 minutes and then EtOH was removed under vacuum, a clear or cloudy water solution was obtained for all 3 vials. The water solutions of the 3 vials were lyophilized overnight to give the slightly yellow solids, which were reconstituted by adding 0.3 ml water into each vial. All other 2 vials gave a clear slightly yellow solution, except that the vial with 10.2 mg HSA gave a little cloudy solution.

| HSA | 13.5 mg | 11.6 mg | 10.2 mg |
|---|---|---|---|
| Ratio of drug: HSA | 6 | 7 | 8 |

Example 8: Non-Covalently Bound Complex of FL-042 and HSA

Example 9: Non-Covalently Bound Complex of FL-043 and HSA

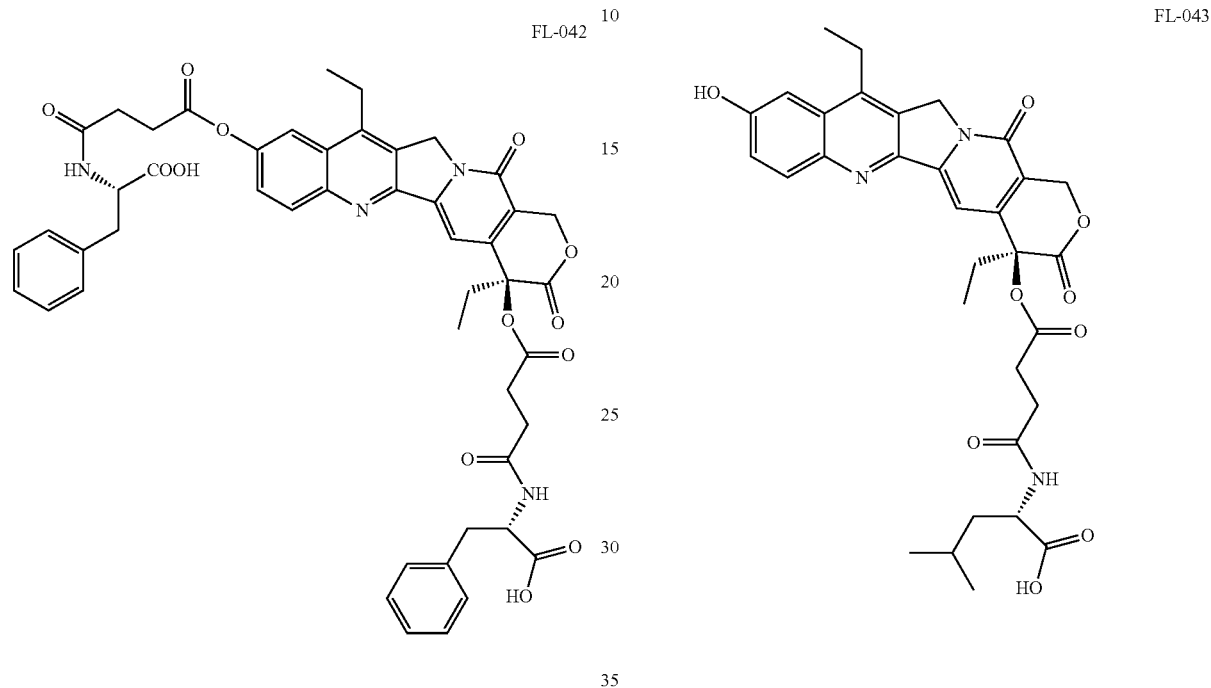

In each of 6 vials, 1 mg of FL-042 was dissolved in 0.5 ml CH$_3$OH. Then 1.5 ml of water was added into each of 6 vials. 12.5 mg, 10.7 mg, 9.4 mg, 8.3 mg, 7.5 mg, and 6.8 mg of HSA were added into each vial. After shaken for 5 minutes and then CH$_3$OH was removed under vacuum, a clear water solution was obtained for all 6 vials. The pH of the all 6 water solution is about 6.5. The water solutions of the 6 vials were lyophilized overnight to give the white solids, which were reconstituted by adding 0.3 ml water into each vial. All 6 vials gave a clear slightly yellow solution.

| HSA | 12.5 mg | 10.7 mg | 9.4 mg | 8.3 mg | 7.5 mg | 6.8 mg |
|---|---|---|---|---|---|---|
| Ratio of drug:HSA | 6 | 7 | 8 | 9 | 10 | 11 |

In each of 7 vials, 1 mg of FL-043 was dissolved in 0.7 ml EtOH. Then 2.1 ml of water was added into each of 7 vials. A clear solution was obtained for all 7 vials. 15.7 mg, 13.7 mg, 12.2 mg, 11 mg, 10 mg, 9.2 mg, and 8.5 mg of HSA were added into each vial. After shaken for 5 minutes and then EtOH was removed under vacuum, a clear water solution was obtained for all 7 vials. The pH of all 7 water solutions is about 6.5. The water solutions of the 7 vials were lyophilized overnight to give the slightly yellow solids, which were reconstituted by adding 0.3 ml water into each vial. All 7 vials gave a clear slightly yellow solution.

| HSA | 15.7 mg | 13.7 mg | 12.2 mg | 11 mg | 10 mg | 9.2 mg | 8.5 mg |
|---|---|---|---|---|---|---|---|
| Ratio of drug:HSA | 7 | 8 | 9 | 10 | 11 | 11.9 | 12.9 |

Example 10: Non-Covalently Bound Complex of FL-044 and HAS

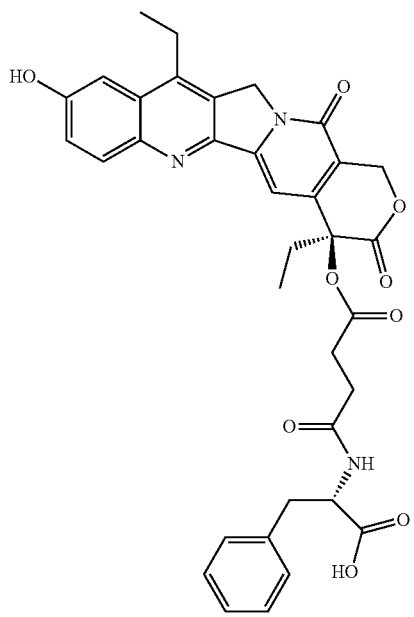

In each of 5 vials, 1 mg of FL-044 was dissolved in 0.5 ml EtOH. Then 1.5 ml of water was added into each of 7 vials. A clear solution was obtained for all 5 vials. 13 mg, 11.6 mg, 10.4 mg, 9.5 mg, and 8.7 mg of HSA were added into each vial. After shaken for 5 minutes and then EtOH was removed under vacuum, a clear water solution was obtained for all other 3 vials except for the vials with 9.5 mg and 8.7mgHSA. The pH of all vials is about 6.5. The water solutions of the 5 vials were lyophilized overnight to give the slightly yellow solids, which were reconstituted by adding 0.3 ml water into each vial. All other 3 vials gave a clear slightly yellow solution, except that the vials with 9.5 mg and 8.7 mg HSA gave a little cloudy solution.

| HSA | 13 mg | 11.6 mg | 10.4 mg | 9.5 mg | 8.7 mg |
|---|---|---|---|---|---|
| Ratio of drug: HSA | 8 | 9 | 10 | 10.9 | 12 |

Example 11: Non-Covalently Bound Complex of TL-001A and HSA

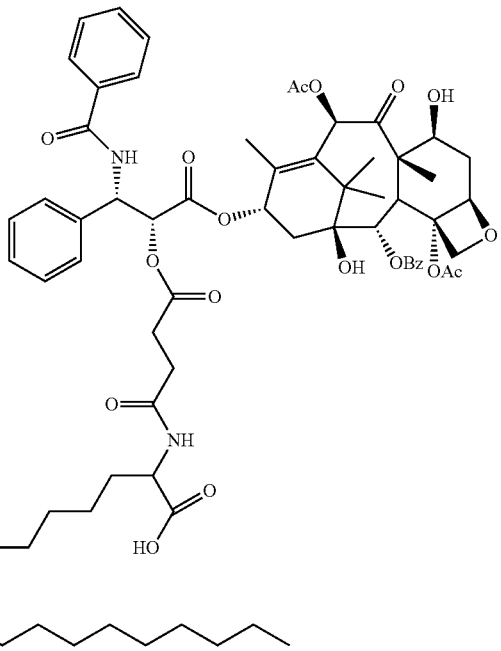

In each of 2 vials, 1 mg of TL-001A was dissolved in 0.5 ml EtOH. Then 1.5 ml of water was added into each of 2 vials. 53.8 mg and 26.9 mg of HSA were added into each vial. After shaken for 5 minutes and then EtOH was removed under vacuum, a clear water solution was obtained for the vial with 53.8 mg HAS, but not for the vial with 26.9 mg HSA. The water solutions of the 2 vials were lyophilized overnight to give the slightly yellow solids, which were reconstituted by adding 1 ml water into the vial with 53.8 mg HAS and 0.5 ml for the vial with 26.9 mg HSA. Both vials gave a clear slightly yellow solution.

| HSA | 53.8 mg | 26.9 mg |
|---|---|---|
| Ratio of drug: HSA | 1 | 2 |

Example 12: Non-Covalently Bound Complex of FL-044 and HSA (1:10)

In a round bottom flask, 50 mg of FL-044 was dissolved in 25 ml EtOH. Then 75 ml of water was added. A clear solution was obtained. 520 mg of HSA were added into the solution. After shaken for 5 minutes and then EtOH was removed under vacuum, a clear water solution was obtained. The pH of all vials is about 6.5. The water solution was lyophilized overnight to give the slightly yellow solids.

TESTS PERFORMED

HSA-Binding Assay

Equilibrium dialysis was performed in a 24-well BD Gentest Serum Binding System (BD Biosciences, Woburn, Mass.). Human serum albumin (HSA) at 0.6 mM was prepared by dissolving in phosphate buffered saline (PBS:

4.01 mL 1 M $K_2HPO_4$+0.99 mL 1 M $KH_2PO_4$+1.37 mL 5 M NaCl+43.63 mL water). After washing and soaking the 24-well BD Gentest Serum Binding System with water, 30% ethanol, and PBS, 750 µL of HSA and 250 µL of PBS were dispensed into each donor and receiver well, respectively. 3.75 µL of 1 mM test compound or wafarin (as control) was spiked into HSA in each donor well. The duplicate incubations were performed at 37° C. for 20 hrs.

After incubation, HSA and buffer samples collected from donor and receiver wells, together with calibration standard samples, were prepared in 96-well plates as shown in Table 2.

TABLE 2

|  | Cal. Std. | HSA Sample | Buffer Sample |
|---|---|---|---|
| Blank HSA (µL) | 50 | 0 | 50 |
| Blank Buffer (µL) | 100 | 100 | 0 |
| MeOH (µL) | 0 | 50 | 50 |
| HSA Sample (µL) | 0 | 50 | 0 |
| Buffer Sample (µL) | 0 | 0 | 100 |
| IS Soln. (µL) | 20 | 20 | 20 |
| Working Std. Soln. (µL) | 50 | 0 | 0 |
| Chilled ACN (µL) | 250 | 250 | 250 |
| Total Volume (µL) | 470 | 470 | 470 |

IS Soln: 20 µM tolbutamide in M:W 1:1 for warfarin; 25 µg/mL propranolol in M:W for test compounds Working Std. Soln.: 10, 20, 100, 200, 1000, 2000, and 10000 µM in methanol The plates were then capped, vortexed, and centrifuged at 3500 rpm for 10 minutes. The supernatant was injected into LC-MS/MS. Sample analysis was performed on an LC/MS/MS system composed of Shimadzu Prominence pumps, SIL-20ACHT autosampler, and Applied Biosystems/MDS Sciex API 3200.

Percent protein binding values were calculated from the concentration data and are listed in Table 3. The protein binding for warfarin in HSA, 99.7%, is consistent with literature values of protein binding of warfarin in human plasma in the range of 98-100%. The % protein binding values for all the test compounds in HSA are higher than 80%. The % protein binding values for all but one of the test compounds in HSA are higher than 97%.

TABLE 3

| | % Protein Binding of Warfarin, as Control, and Test Compounds in HSA | |
|---|---|---|
| Compound | Incubation Conc. (µM) | % Protein Binding in Human Serum Albumin |
| Warfarin | 5 | 99.7 |
| FL-003 | 5 | >99.9 |
| FL-037 | 5 | >97.7 |
| FL-038 | 5 | >83.2 |
| FL-040 | 5 | 98.4 |
| FL-041 | 5 | >97.8 |
| FL-043 | 5 | 97.0 |

In Vivo Test of Efficacy of Non-Covalently Bound Complex of FL-044 and HSA (1:10) in the Treatment of a Subcutaneous HT-29 Xenograft Model Protocol:

HT29 tumor fragment was implanted subcutaneously into female, athymic (Ncr:Nu) nude mice.
Tumors were allowed to reach a weight of 135 to 184 mg with HT29 tumor cells.
Mice bearing subcutaneously implanted HT29 tumors received either two doses of Non-covalently bound complex of FL-044 and HSA (1:10) or 30 mg/kg irinotecan.
Each treatment group (n=8) received a total of three intravenous doses administered every fourth day (q4dx3).
Animals were weighed and tumor volumes measured twice weekly after the first drug injection. Tumor volumes were converted to tumor weight assuming a tumor density of 1 mm3=1 mg.
Animals exhibiting poor condition due to tumor progression were euthanized accordingly. Any remaining animals were sacrificed on Days 60 for the HT29 study.
Anti-tumor activity was measured as changes in tumor weight, tumor growth inhibition, tumor regression and duration of regression.
Tolerability was measured as body weight loss and deaths due to drug toxicity.

Results:

The results of the body weight changes in the tumor bearing mice are shown in FIG. 1.

Figure 2:
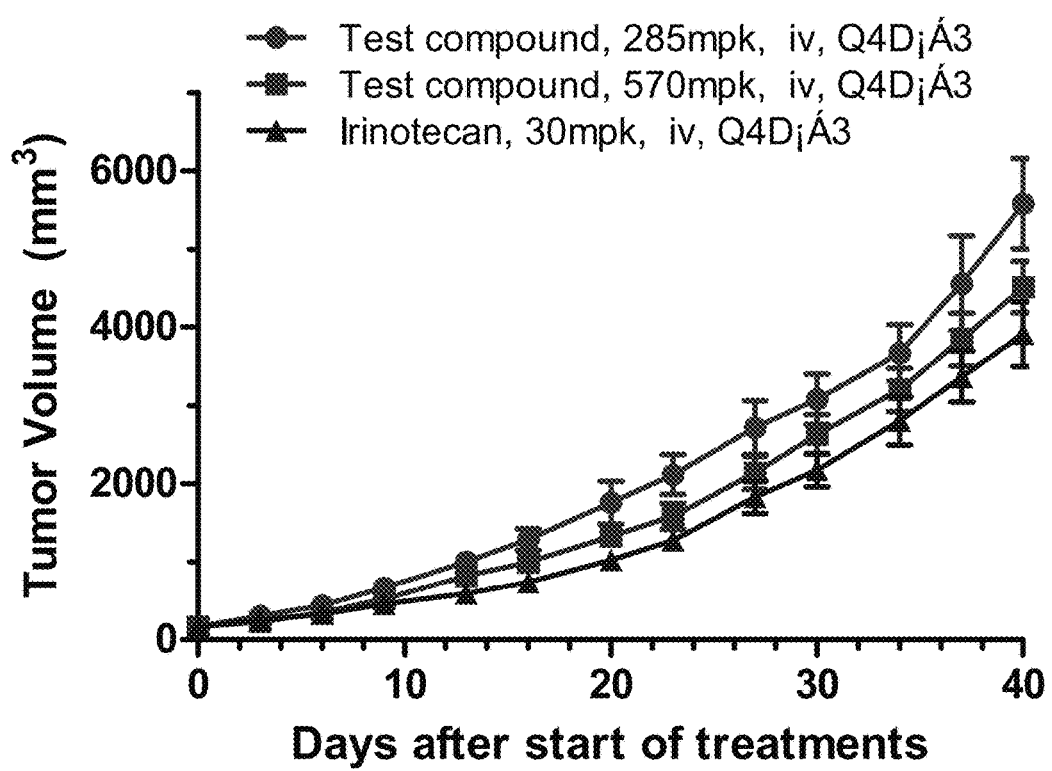
FIG. 2 is a line plot showing antitumor activity of compounds in the treatment of a HT-29 subcutaneous xenograft model.

The tumor growth curves of different treatment groups are shown in FIG. 2.

The invention claimed is:

1. A non-covalently bound complex, comprising:
serum albumin, and
a camptothecin analog of Formula I:

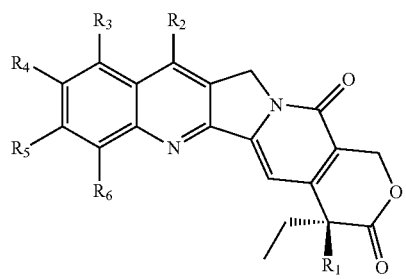

wherein
$R_1$ is OH or a linker-serum-albumin-binding-moiety wherein $R_{11}$ is O;
$R_{2-6}$ are each, independently, H, halo, OH, $NO_2$, $NH_2$, lower alkyl, O-lower alkyl, NH-lower alkyl, N(lower alkyl)$_2$, lower alkyl-N(lower alkyl)$_2$, lower alkyl-Si (lower alkyl)$_3$,

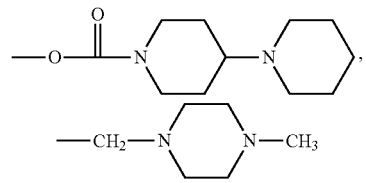

or
a linker-serum-albumin-binding-moiety;
wherein:
$R_4$ and $R_5$ optionally, together form —$OCH_2CH_2O$—,
$R_2$ and $R_3$ optionally, together form —C(NH$_2$)H—CH$_2$—CH$_2$—, and
at least one of $R_1$, $R_2$, $R_3$, $R_4$, $R_5$, and $R_6$ comprises a linker-serum-albumin-binding-moiety,
wherein the linker-serum-albumin-binding-moiety comprises:

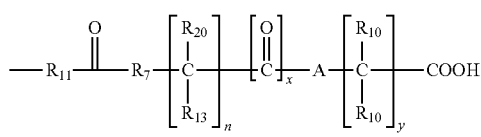

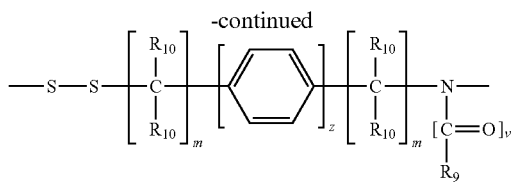
-continued wherein $R_{11}$ is:
- O, if the linker-serum-albumin-binding-moiety substitutes for an alcohol group on the camptothecin analog of Formula I,
- S, if the linker-serum-albumin-binding-moiety substitutes for a thiol group on the camptothecin analog of Formula I,
- NH, if the linker-serum-albumin-binding-moiety substitutes for a primary amine group on the camptothecin analog of Formula I, or
- —N-lower alkyl, if the linker-serum-albumin-binding-moiety substitutes for a secondary amine group on the camptothecin analog of Formula I;

$R_7$ is a covalent bond, if $R_{11}$ is S; otherwise, $R_7$ is selected from the group consisting of O, NH and a covalent bond;

A is

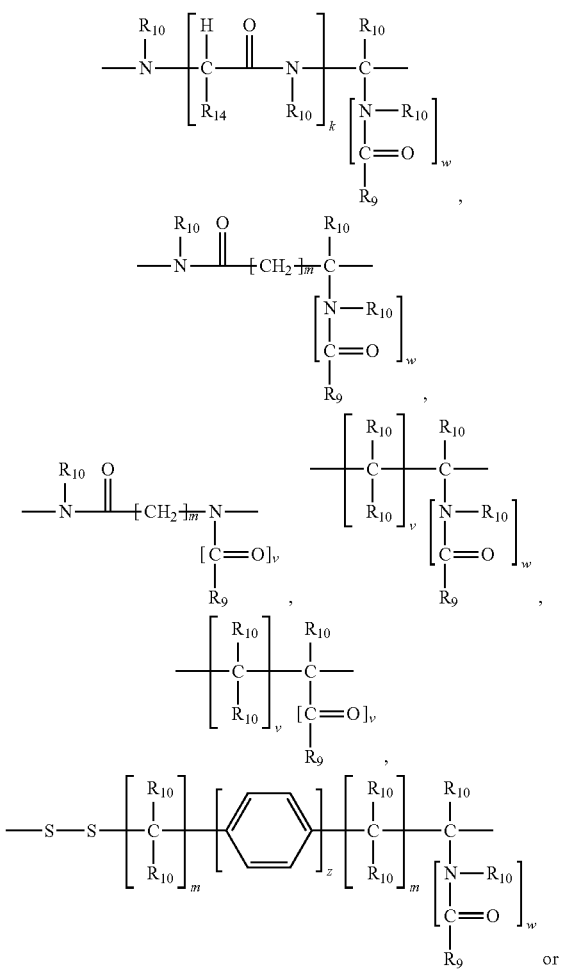

$R_9$ is an unbranched or branched alkyl, alkylene or alkyne of 2 to 30 carbon atoms optionally including one or more ring structures of 3 to 6 atoms when $R_9$ has at least 7 carbon atoms, including heteroatoms of oxygen in an integer number from 0 to one fifth the total number of carbon atoms in $R_9$, and optionally substituted with up to three groups selected from the groups consisting of halo, nitro, amine, amide, hydroxyl, O-lower alkyl and carboxy; with the proviso that there be no covalent bonds between oxygen atoms in $R_9$;

$R_{10}$ is, independently in each instance, H or lower alkyl;

$R_{13}$ is, independently in each instance, H, OH, $NO_2$, $NH_2$, $NH_3^+$, SH or a branched or unbranched alkyl, alkylene or alkyne of 1 to 8 carbon atoms, wherein the alkyl, alkylene or alkyne is optionally substituted with one or two substituents selected from the group consisting of halo, OH, $NO_2$, $NH_2$, $NH_3^+$, SH and =O, and optionally includes up to two heteroatoms independently selected from O, S and N, with the proviso that no O, S or N atom in the alkyl, alkylene or alkyne is covalently bonded to any other O, S or N atom;

$R_{14}$ is, independently in each instance, H, OH, $NO_2$, $NH_2$, $NH_3^+$, SH or a branched or unbranched alkyl, alkylene or alkyne of 1 to 10 carbon atoms, wherein the alkyl, alkylene or alkyne optionally includes one or more ring structures of 3 to 9 atoms, is optionally substituted with one or two substituents selected from the group consisting of halo, OH, $NO_2$, $NH_2$, $NH_3^+$, SH and =O, and optionally includes up to two heteroatoms independently selected from O, S and N, with the proviso that no O, S or N atom in the alkyl, alkylene or alkyne is covalently bonded to any other O, S or N atom;

$R_{20}$ is, independently in each instance, H or lower alkyl, and two $R_{20}$ may optionally together form a ring structure of up to 8 carbon atoms;

k is 0, 1 or 2;

m, independently in each instance, is 0, 1, 2 or 3;

n is an integer from 1 to 8;

v is 0 or 1;

w is 0 or 1;

x is 0 or 1, with the proviso that x is 0 when a di-sulfide bond is present in A;

y is 0, 1, 2 or 3; and z is 0 or 1, wherein the non-covalently bound complex has a molar ratio of the camptothecin analog of Formula I to serum albumin from about 1:1 to about 16:1 and has a solubility in aqueous solution of at least 5 mg/ml.

2. The non-covalently bound complex of claim 1, wherein the serum albumin is human serum albumin.

3. The non-covalently bound complex of claim 1, in a solid formulation.

4. The non-covalently bound complex of claim 2, in an aqueous formulation.

5. The non-covalently bound complex of claim 2, wherein the aqueous formulation is substantially free of solvents other than water.

6. The non-covalently bound complex of claim 1, wherein the camptothecin analog of Formula I is selected from the group consisting of camptothecin, topotecan, irinotecan, 7-ethyl-10-hydroxy-camptothecin, 9-aminocamptothecin, 9-nitrocamptothecin, (S)-ethyl-8-hydroxy-15-(4-methylpiperazin-1-ylmethyl)-2,3,8,9,11,12-hexahydro-14H-1,4-dioxino[2,3-g]pyrano[3',4':6,7]indolizino[1,2-b]quinoline-9,12-dione, (1S,9S)-1-amino-9-ethyl-5-fluoro-1,2,3,9,12,15-hexahydro-9-hydroxy-4-methyl-10H,13H-benzo(de)pyrano(3',4':6,7) indolizino(1,2-b)quinoline-10,13-dione, and (4S)-4-ethyl-4-hydroxy-11-(2-trimethylsilyl)ethyl)-1H-pyrano[3',4': 6,7]indolizino[1,2-b]quinoline-3,14(4H, 12H)-dione, wherein at least one alcohol or a primary amine group in the camptothecin analog is substituted with the linker-serum-albumin-binding-moiety.

7. The non-covalently bound complex of claim 6, wherein the serum albumin is human serum albumin.

8. The non-covalently bound complex of claim 7, in an aqueous formulation.

9. The non-covalently bound complex of claim 8, wherein the aqueous formulation is substantially free of solvents other than water.

10. The non-covalently bound complex of claim 1, wherein
$R_2$ is —CH$_2$CH$_3$;
$R_3$ is —H:
$R_4$ is

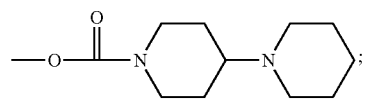 [SMILES: COC(=O)N1CCC(N2CCCCC2)CC1]

$R_5$ is H;
$R_6$ is H; and
$R_1$ is linker-HSA binding moiety, wherein $R_{11}$ is O.

11. The non-covalently bound complex of claim 1, wherein
$R_2$ is H;
$R_3$ is

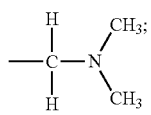

$R_4$ is —OH or linker-HSA binding moiety;
$R_5$ is H;
$R_6$ is H;
$R_1$ is —OH or linker-HSA binding moiety;
wherein at least one of $R_1$ and $R_4$ is linker-HSA binding moiety, wherein $R_{11}$ is O.

12. The non-covalently bound complex of claim 1, wherein $R_2$ is —CH$_2$CH$_3$; $R_3$ is H; $R_4$ is —OH or linker-HSA binding moiety; $R_5$ is H; $R_6$ is H; $R_1$ is —OH or linker-HSA binding moiety; wherein at least one of $R_1$ and $R_4$ is linker-HSA binding moiety, wherein $R_{11}$ is O.

13. The non-covalently bound complex of claim 10, wherein linker-HSA binding moiety is:

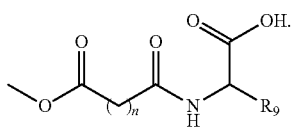

14. The non-covalently bound complex of claim 7, wherein the camptothecin analog of Formula I is:

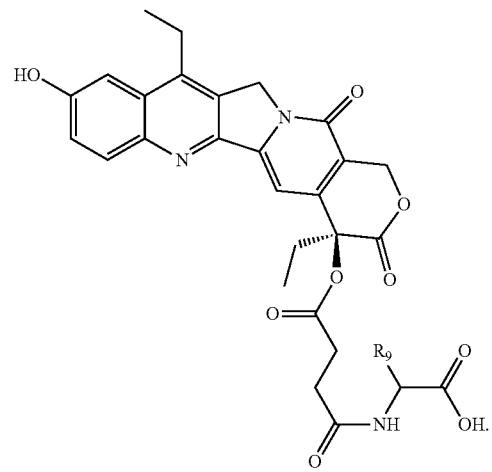

15. The non-covalently bound complex of claim 7, wherein the camptothecin analog of Formula I is:

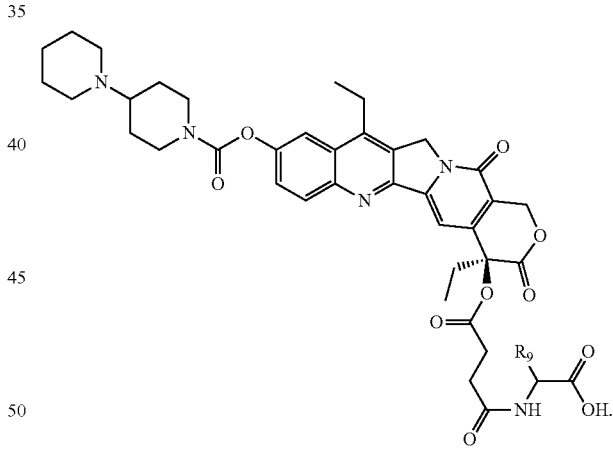

16. A method to treat cancer in a patient comprising administering a composition comprising a non-covalently bound complex of claim 7 to said patient in an effective amount to treat said cancer.

* * * * *

UNITED STATES PATENT AND TRADEMARK OFFICE
CERTIFICATE OF CORRECTION

PATENT NO. : 9,962,452 B2  
APPLICATION NO. : 14/765773  
DATED : May 8, 2018  
INVENTOR(S) : Qun Sun

Page 1 of 2

It is certified that error appears in the above-identified patent and that said Letters Patent is hereby corrected as shown below:

On the Title Page

Item (*) (Notice) In Column 1 Line 3 delete "days. days." and insert -- days. --, therefor.

In the Specification

In Column 1 Lines 7-10 delete "claims the benefit of U.S. Provisional Application Ser. No. 61/760,573, filed Feb. 4, 2013. The disclosure of the prior application is considered part of and is" and insert -- is a National Stage application under 35 U.S.C. §371 of International Application No. PCT/US2014/014079, having an International Filing Date of January 31, 2014, which claims the benefit of U.S. Provisional Application Serial No. 61/760,573, filed February 4, 2013. The disclosure of the prior applications are considered part of and are --, therefor.

Signed and Sealed this  
Fourth Day of August, 2020

Andrei Iancu  
*Director of the United States Patent and Trademark Office*

CERTIFICATE OF CORRECTION (continued)
U.S. Pat. No. 9,962,452 B2

In the Claims

In Column 87 Line 52-58 In Claim 1, delete

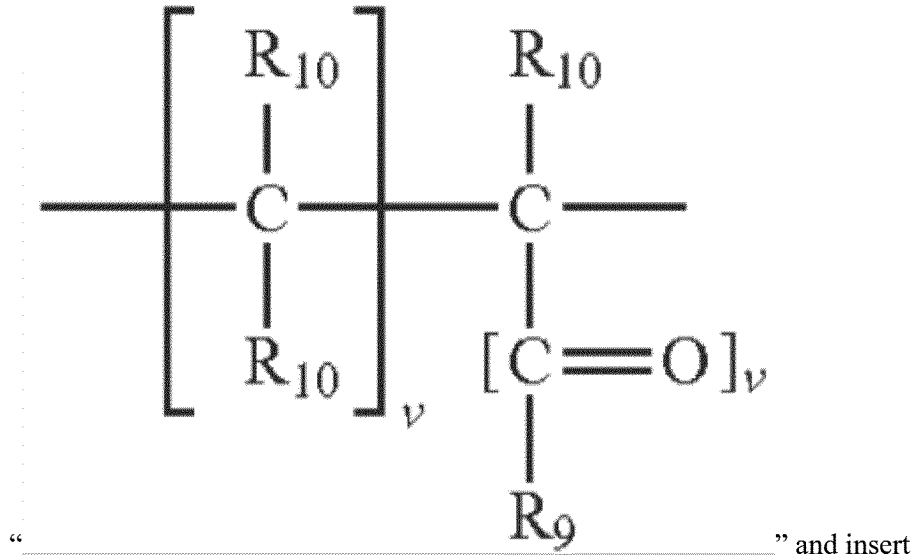

" and insert

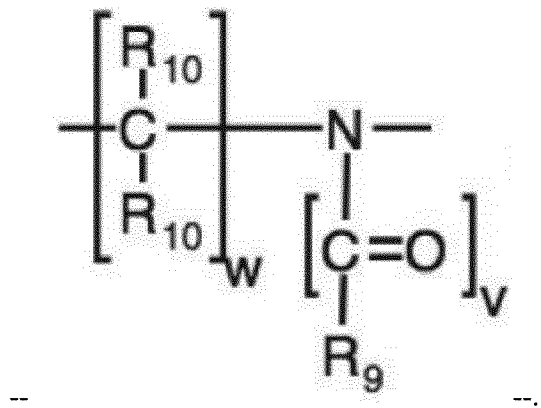

--.

In Column 88 Line 62 In Claim 3, delete "1," and insert -- 2, --, therefor.

In Column 88 Line 65 In Claim 5, delete "2," and insert -- 4, --, therefor.

In Column 89 Line 11 In Claim 6, delete "ethyl)" and insert -- ethyl --, therefor.

In Column 89 Line 12 In Claim 6, delete "[3',4': 6,7]" and insert -- [3',4':6,7] --, therefor.

In Column 89 Line 12 In Claim 6, delete "(4H, 12H)" and insert -- (4H,12H) --, therefor.

In Column 89 Line 24 In Claim 10, delete "–H:" and insert -- –H; --, therefor.